(12) United States Patent
Cahoon et al.

(10) Patent No.: US 7,244,563 B2
(45) Date of Patent: Jul. 17, 2007

(54) GENES FOR PLANT FATTY ACID MODIFYING ENZYMES ASSOCIATED WITH CONJUGATED DOUBLE BOND FORMATION

(75) Inventors: Edgar Benjamin Cahoon, Greenville, DE (US); Thomas J. Carlson, Ardentown, DE (US); William Dean Hitz, Wilmington, DE (US); Kevin G. Ripp, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 551 days.

(21) Appl. No.: 10/287,401

(22) Filed: Nov. 4, 2002

(65) Prior Publication Data

US 2003/0126640 A1    Jul. 3, 2003

(51) Int. Cl.
*C12Q 1/68* (2006.01)
(52) U.S. Cl. .......................................... 435/6
(58) Field of Classification Search .................. None
See application file for complete search history.

(56) References Cited

U.S. PATENT DOCUMENTS

| | | | |
|---|---|---|---|
| 5,428,072 A | 6/1995 | Cook et al. | 514/560 |
| 5,554,646 A | 9/1996 | Cook et al. | 514/560 |
| 5,668,292 A | 9/1997 | Somerville et al. | 800/205 |
| 5,851,572 A | 12/1998 | Cook et al. | 426/2 |
| 5,919,451 A | 7/1999 | Cook et al. | 424/130.1 |

FOREIGN PATENT DOCUMENTS

| | | |
|---|---|---|
| EP | 0 794 250 A1 | 9/1997 |
| WO | WO 97/21340 | 6/1997 |

OTHER PUBLICATIONS

Broun et al, Science 282: 1315-1317, Nov. 13, 1998.*
DeLuca, V. AgBiotech News and Information 5(6): 225N-229N, 1993.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
van de Loo, PNAS, USA 92:6743-6747, Jul. 1995.*
Bagby, M.O. et al., Stereochemistry of α-Parinaric Acid from *Impatiens edgeworthii* Seed Oil, *Lipids*, 1(4), 263-267, 1966.
Ghisholm, Mary J. et al., Fatty Acid Composition of Some Cucurbitaceae Seed Oils, *Canadian Journal of Chemistry*, 42, 560-564, 1964.
Liu, Linsen et al., In Vivo Studies of the Biosynthesis of α-Eleostearic Acid in the Seed of *Momordica charantia* L., *Plant Physiol.*, 113, 1343-1349, 1997.
Crombie, Leslie et al., The Biosynthesis of Calendic Acid, Octadeca-(8E,10E,12Z)-trienoic Acid, by Developing Marigold Seeds: Origins of (E,E,Z) and (Z,E,Z) Conjugated Triene Acids in Higher Plants, *J. Chem. Soc. Perkin Trans. I*, 2425-2434, 1985.
Hitz, William D. et al., Cloning of a Higher-Plant Plastid ω-6 Fatty Acid Desaturase cDNA and Its Expression in a Cyanobacterium, *Plant Physiol.*, 105, 635-641, 1994.
van de Loo, Frank J. et al., An oleate 12-hydroxylase from *Ricinus communis* L. is a fatty acyl desaturase homolog, *Proc. Natl. Acad. Sci. USA*, 92, 6743-6747, Jul. 1995.
Shanklin, John et al., Eight Histidine Residues Are Catalytically Essential in a Membrane-Associated Iron Enzyme, Stearoyl-CoA Desaturase, and Are Conserved in Alkane Hydroxylase and Xylene Monooxygenase, *Biochemistry*, 33(43), 12787-12794, 1994.
Badami, R.C. et al., Structure and Occurrence of Unusual Fatty Acids in Minor Seed Oils, *Prog. Lipid Res.*, 19, 119-153, 1981.
Okuley, John et al., Arabidopsis FAD2 Gene Encodes the Enzyme That Is Essential for Polyunsaturated Lipid Synthesis, *The Plant Cell*, 6, 147-158, Jan. 1994.
Shure, M. et al., Molecular Identification and Isolation of the Waxy Locus in Maize, *Cell*, 35, 225-233, Nov. 1983.
Lee, Michael et al., Identification of Non-Heme Diiron Proteins That Catalyze Triple Bond and Epoxy Group Formation, *Science*, 280, 915-918, May 8, 1998.
Ohlrogge, John B., Design of New Plant Products: Engineering of Fatty Acid Metabolism, *Plant Physiol.*, 104, 821-826, 1994.
Eggert, J.M. et al., Effects of conjugated linoleic acid (CLA) on the growth and composition of lean gilts, *Journal of Animal Science*, 77, Supplement 1, 53, 1999.
Thiel, R.L. et al., Conjugated linoleic acid improves performance and body composition in swine, *Journal of Animal Science*, 76, Supplement 2, 57, 1998.
Wiegand, B.R. et al., Effects of length of feeding conjugated linoleic acid (CLA) on growth and body composition of pigs, *Journal of Animal Science*, 77, Supplement 1, 178, 1999.
Harwood, J.L., In The Biochemistry of Plants, Plant Acyl Lipids: Structure, Distribution, and Analysis, vol. 4, 1-55, 1980.
Okuley, J. et al., Omega-6 Fatty Acid Desaturase, Endoplasmic Reticulum (EC 1.14.99.-) (Delta-12 Desaturase), *EMBL Sequence Database Ac. P46313*, Nov. 1, 1995.

* cited by examiner

*Primary Examiner*—Elizabeth F. McElwain

(57) ABSTRACT

The preparation and use of nucleic acid fragments encoding plant fatty acid modifying enzymes associated with conjugated double bond formation or functionally equivalent subfragments thereof are disclosed. Chimeric genes incorporating such nucleic acid fragments or functionally equivalent subfragments thereof or complement thereof and suitable regulatory sequences can be used to create transgenic plants having altered lipid profiles.

5 Claims, 6 Drawing Sheets

Figure 2:
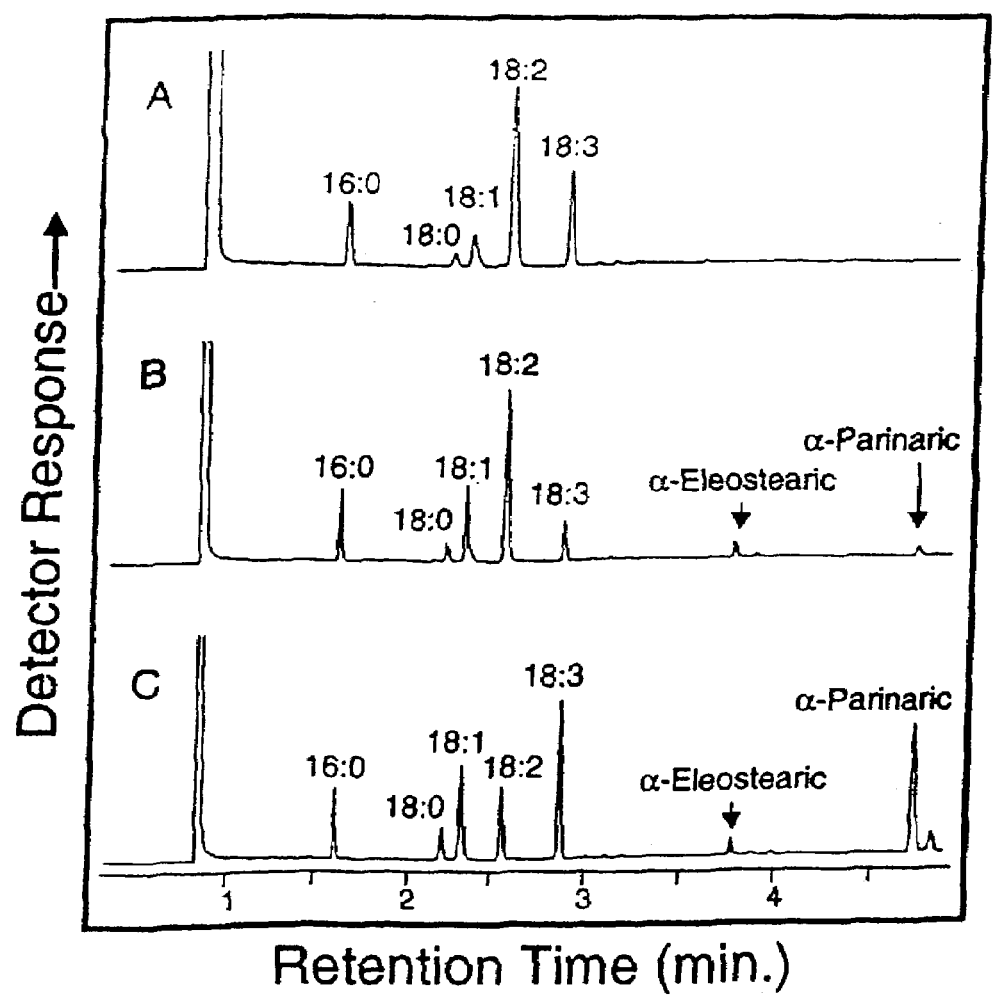

```
                        :                                                    60
Hydroxylase    MGGGGRMSTVITSNNSEKKG--GSS--HLKRAPHTKPPFTLGDLKRAIPPHCFERSFVRS
ImpFad2H8      MGEVGPTNR--TKTKLDKQQESEN------RVPHEPPPFTLSDLKKAIPPHCFERSLVKS
MomFad2        MGGRGAIGVLRNGGGPKKKMGPGQGLGPGERITHARPPFSISQIKKAIPPHCFQRSLRRS
ChrFad2        MGAGGQKTFPRLEEEEKQQQAAAAGF---KRIPTTKPPFTLSDLKKAIPPHCFQRSLLRS
LinFad2        MGAGGQKTCPRLVEEEKQQQAAAAGF---KRIPTTKPPFTLSDLKKAIPPHCFQRSLLRS
AleC1                                     KAIPPHCFQRSVLRS
AleC2                                     KAIPPHCFKRSLLRS
soy omega-6    MGLA-KETTMGGRGRVAKVEVQGKK--PLSRVPNTKPPFTVGQLKKAIPPHCFQRSLLTS 61                                       *             120
Hydroxylase    FSYVAYDVCLSFLFYSIATNFFPYISSPL-SYVAWLVYWLFQGCILTGLWVIG H ECG H HA
ImpFad2H8      FYHVIHDIIILSFFYYVAANYIPMLPQNL-RYVAWPIYWAIQGCVQLGILVLG H ECG H HA
MomFad2        FSYLLSDIALVSAFYYVADTYFHRLPHPLLHYLAWPVYWFCQGAVLTGMWGIA H DCG H HA
ChrFad2        FSYVFIDLTIISILGYIGATYICLLPPPS-KYLAWLLYWAVQGCFFTGAWALA H DCG H HA
LinFad2        FSYVFIDLTIISILGYIAATYIYLLPPPS-KYLAWLLYWAVQGCFFTGAWALA H DCG H HA
AleC1          FSYVVYDLTVAFIFYYIATNYFHLLPQPL-SYVAWPIYWALQGCVLTGVWVIA H ECG H HA
AleC2          FSYVVYDLSLSFIFYSIATTYFHLLPSPI-TYIAWPVYWAFQGCILTSVWVLG H ECG H HA
soy omega-6    FSYVVYDLSFAFIFY-IATTYFHLLPQPF-SLIAWPIYWVLQGCLLTGVWVIA H ECG H HA 121                                                    180
Hydroxylase    FSEYQLADDIVGLIVHSALLVPYFSWKYS H RR HH SNIGSLERDEVFVPKSKSKISWY-SKY
ImpFad2H8      FSDYQWVDDMVGFVLHSSQLIPYFSWKHS H RR HH SNTASIERDEVYPPAYKNDLPWF-AKY
MomFad2        FSDYQLVDDVVGFLIHSLVFVPYFSFKIS H RR HH SNTSSVDRDEVFVPKPKAKMPWY-FKY
ChrFad2        FSDYQWIDDAVGMVLHSTLMVPYFSFKYS H RR HH SNINSLERDEVFVPRPKSKIKWYCSKY
LinFad2        FSDYQWVDDAVGMVLHSALMVPYFSFKYS H RR HH SNINSLERDEVFVPRPKFKIKWYCSKY
AleC1          FSDYQLLDDIVGLVLHSCLLVPYFSWKHS H RR HH SNTASLERDEVFVPKKKSSIRWF-SKY
AleC2          FSEYNWLDDTIGLILHSSLLVPYFSFKIS H RR HH SNIASLERDEVFVPRLKSAIPWY-SKY
soy omega-6    FSKYQWVDDVVGLTLHSTLLVPYFSWKIS H RR HH SNTGSLDRDEVFVPKPKSKVAWF-SKY 181                                                    240
Hydroxylase    SNNPPGRVLTLAATLLLGWPLYLAFNVSGRPYDRFACHYDPYGPIFSERERLQIYIADLG
ImpFad2H8      LRNPVGRFLMIFGALLFGWPSYLLFNANGRLYDRFASHYDPQSPIFNNRERLQVIASDVG
MomFad2        LTNPPARVFIIFITLTLGWPMYLTFNISGRYYGRFTSHFDPNSPIFSPKERVLVHISNAG
ChrFad2        LNNPLGRVLTLAVTLILGWPMYLALNASGRDYDRFVSHFYPYGPIYNDRERLQIYISDAG
LinFad2        LNNPLGRVLTLAVTLILGWPMYLAFNASGRDYDRFVSHFYPYGPIYNDRERLQIYISDAG
AleC1          LNNPPGRLFTLTITLTLGWPLYLAFNVSGRPYDRFACHYDPYGPIYTDRERTEIYISDAG
AleC2          LNNPPGRALTLVATLFIGWPLYLAFNVSGRYYDRFACHYDPYSPIYSDRERLQIYISDAM
soy omega-6    LNNPLGRAVSLLVTLTIGWPMYLAFNVSGRPYDSFASHYHPYAPIYSNRERLLIYVSDVA 241                                                    300
Hydroxylase    IFATTFVLYQATMAKGLAWVMRIYGVPLLIVNCFLVMITYLQHTHPAIPRYGSSEWDWLR
ImpFad2H8      LVFAYFVLYKIALAKGFVWLICVYGVPYVILNGLIVLITFLQHTHPNLPRYDLSEWDWLR
MomFad2        LVATGYLLYRIAMAKGVGWLIRLYGVPLIVLNACVVLITALQHTHPSFPYYDSTEWDWLR
ChrFad2        IFIVSYVLYQVALAKGLPWLICIYGVPLFVNNALVVTITYLQHTHPELPRYGNSEWDWFK
LinFad2        IFIVSYVLYQVALAKGLPWLICIYGVPLFVNNALVVTITYLQHTHPELPRYGNSEWDWFK
AleC1          VLAVTFGLYRLAAAKGLAWVICVYGVPLLIVNALVVMITYLQHTHPSIPHYDSSEWDWLR
AleC2          IFVAAYVLYKIAMAKGLAWLVCIYGVPLLIVNALVVTITSLQHTHVALPHYDSSEWDWLR
soy omega-6    LFSVTYSLYRVATLKGLVWLLCVYGVPLLIVNGFLVTITYLQHTHFALPHYDSSEWDWLK
```

FIGURE 1

```
              301                                                       360
Hydroxylase   GAMVTVDRDYG-VLNKVFHNIADT H VA HH LFATVPHYHAMEATKAIKPIMGEYYRYDGTP
ImpFad2H8     GALSTVDRDYG-MLNKVFHNVTDT H LV HH LFTTMPHYRAKEATEVIKPILGDYYKFDDTP
MomFad2       GNLVTVDRDYGPIMNRVFHHITDT H VV HH LFPSMPHYNGKEATVAAKRILGEYYQFDGTP
ChrFad2       GTLATVDRDMGPLLNWATHHVSDT H YV HH LFSTMPHYHGVEATKAVKPMLGEYYRFDPTP
LinFad2       GTLATVDRDMGPLLNWVTHHVSDT H YV HH LFSTMPHYHGVEATKAVKPMLGEYYRFDPTP
AleC1         G
AleC2         G
soy omega-6   GALATMDRDYG-ILNKVFHHITDT H VA HH LFSTMPHYHAMEATNAIKPILGEYYQFDDTP 361                                     400
Hydroxylase   FYKALWREAKECLFVEPDE------GAPTQGVFWYRNK-Y
ImpFad2H8     FLKALWKDMGKCIYVESDV------PGKNKGVYWYNNDI
MomFad2       IWKAAWREFRECVYVEPDEDDGATSGSSSKGVFWYHNKL
ChrFad2       LYKALWREAKECLFVEPDS-------KSPGVFWFDKF
LinFad2       VYKALWREAKECLFVEPDS-------KSPGVFWFDKF
soy omega-6   FYKALWREARECLYVEPDE------GTSEKGVYWYRNK-Y
```

FIGURE 1 (CONTINUED)

SEQUENCE LISTING

<160> NUMBER OF SEQ ID NOS: 34

<210> SEQ ID NO 1
<211> LENGTH: 1456
<212> TYPE: DNA
<213> ORGANISM: Impatiens balsamina
<220> FEATURE:
<221> NAME/KEY: CDS
<222> LOCATION: (19)..(1170)

<400> SEQUENCE: 1

```
catttggata gaggaatc atg gga gaa gtg gga ccc aca aac cga acc aaa        51
                    Met Gly Glu Val Gly Pro Thr Asn Arg Thr Lys
                     1               5                  10 acc aag ttg gac aag caa caa gaa tcc gaa aac agg gtt cct cac gag       99
Thr Lys Leu Asp Lys Gln Gln Glu Ser Glu Asn Arg Val Pro His Glu
             15                  20                  25 cca cct cca ttc aca cta agt gac ctt aag aaa gcc atc cca ccc cat     147
Pro Pro Pro Phe Thr Leu Ser Asp Leu Lys Lys Ala Ile Pro Pro His
         30                  35                  40 tgc ttc gag cgc tcc ctc gtg aaa tca ttc tac cac gtg att cac gac     195
Cys Phe Glu Arg Ser Leu Val Lys Ser Phe Tyr His Val Ile His Asp
     45                  50                  55 att atc atc ctg tcc ttt ttc tac tat gtc gcc gcc aat tac atc ccc     243
Ile Ile Ile Leu Ser Phe Phe Tyr Tyr Val Ala Ala Asn Tyr Ile Pro
 60                  65                  70                  75 atg cta ccc caa aac ctc cgt tac gtt gca tgg cca att tat tgg gcc     291
Met Leu Pro Gln Asn Leu Arg Tyr Val Ala Trp Pro Ile Tyr Trp Ala
                 80                  85                  90
```

| | |
|---|---|
| atc caa ggc tgt gtc caa ctt ggt ata ttg gtc tta ggc cat gaa tgc<br>Ile Gln Gly Cys Val Gln Leu Gly Ile Leu Val Leu Gly His Glu Cys<br>              95                    100                    105 | 339 |
| ggc cac cac gcc ttc agc gac tac caa tgg gta gac gac atg gtc ggg<br>Gly His His Ala Phe Ser Asp Tyr Gln Trp Val Asp Asp Met Val Gly<br>        110                    115                    120 | 387 |
| ttc gtc ctc cac tcg tcc caa ttg att ccc tac ttc tca tgg aaa cat<br>Phe Val Leu His Ser Ser Gln Leu Ile Pro Tyr Phe Ser Trp Lys His<br>        125                    130                    135 | 435 |
| agc cac cgt cgc cac cac tcc aac acg gcc tcc atc gag cgc gac gag<br>Ser His Arg Arg His His Ser Asn Thr Ala Ser Ile Glu Arg Asp Glu<br>140                    145                    150                    155 | 483 |
| gtc tac ccg ccc gcg tac aaa aac gac ctg ccg tgg ttc gcc aaa tac<br>Val Tyr Pro Pro Ala Tyr Lys Asn Asp Leu Pro Trp Phe Ala Lys Tyr<br>                    160                    165                    170 | 531 |
| cta cgc aac ccc gtc ggt cgt ttc ctc atg att ttc ggg gcg cta ctg<br>Leu Arg Asn Pro Val Gly Arg Phe Leu Met Ile Phe Gly Ala Leu Leu<br>        175                    180                    185 | 579 |
| ttc ggc tgg ccg tcg tac ctt ctg ttc aac gcg aac ggc cgt ctc tac<br>Phe Gly Trp Pro Ser Tyr Leu Leu Phe Asn Ala Asn Gly Arg Leu Tyr<br>            190                    195                    200 | 627 |
| gac cgc ttc gct tcc cac tac gac ccg caa tcc ccg atc ttc aac aac<br>Asp Arg Phe Ala Ser His Tyr Asp Pro Gln Ser Pro Ile Phe Asn Asn<br>205                    210                    215 | 675 |
| cgc gag agg ctg caa gtg atc gcg tcc gac gtc ggg ctc gtc ttc gcg<br>Arg Glu Arg Leu Gln Val Ile Ala Ser Asp Val Gly Leu Val Phe Ala<br>220                    225                    230                    235 | 723 |
| tac ttt gtc ctg tac aag atc gcg ctg gcc aag gga ttt gtg tgg tta<br>Tyr Phe Val Leu Tyr Lys Ile Ala Leu Ala Lys Gly Phe Val Trp Leu<br>                    240                    245                    250 | 771 |
| att tgt gtg tat ggc gtc ccg tac gtg atc ctc aac ggg ctt atc gtc<br>Ile Cys Val Tyr Gly Val Pro Tyr Val Ile Leu Asn Gly Leu Ile Val<br>              255                    260                    265 | 819 |
| ttg atc acg ttc cta cag cac acg cac ccg aat ctg ccc cgt tac gac<br>Leu Ile Thr Phe Leu Gln His Thr His Pro Asn Leu Pro Arg Tyr Asp<br>            270                    275                    280 | 867 |
| ctt tcc gag tgg gac tgg ctt agg gga gcc ctg tcg act gtg gac cgc<br>Leu Ser Glu Trp Asp Trp Leu Arg Gly Ala Leu Ser Thr Val Asp Arg<br>        285                    290                    295 | 915 |
| gat tac ggg atg ttg aat aag gtg ttc cat aac gtg acg gac acg cac<br>Asp Tyr Gly Met Leu Asn Lys Val Phe His Asn Val Thr Asp Thr His<br>300                    305                    310                    315 | 963 |
| ttg gtg cat cat ttg ttc acg acc atg cca cat tat cgc gcc aag gag<br>Leu Val His His Leu Phe Thr Thr Met Pro His Tyr Arg Ala Lys Glu<br>                  320                    325                    330 | 1011 |
| gcg acc gag gtg att aaa ccg ata ttg gga gac tac tat aag ttt gac<br>Ala Thr Glu Val Ile Lys Pro Ile Leu Gly Asp Tyr Tyr Lys Phe Asp<br>        335                    340                    345 | 1059 |
| gac act ccg ttt ctc aaa gcg ttg tgg aag gac atg gga aag tgt att<br>Asp Thr Pro Phe Leu Lys Ala Leu Trp Lys Asp Met Gly Lys Cys Ile<br>            350                    355                    360 | 1107 |
| tat gtg gag tcg gac gtg cct ggc aag aac aag gga gtt tat tgg tac<br>Tyr Val Glu Ser Asp Val Pro Gly Lys Asn Lys Gly Val Tyr Trp Tyr<br>365                    370                    375 | 1155 |
| aat aac gac att tga agaggaaatg gttgccggtg tctttaatgt tttgtttagt<br>Asn Asn Asp Ile<br>380 | 1210 |
| ttgtgttgtt tcgttcaatg ttatattgtg tcatgttcaa ataaaataaa acggtccatg | 1270 |
| tattttgtgg ttgtattgtc tattgtaatt ttacaattat tctaagaaat atgtctaaaa | 1330 |

```
gaatttgggt cggcccaata ctagtcgggt caatccaacc ccatgtcatc caacccgaat    1390
ctgtgttgta atttggccag ggtggatcct ctgtcccgaa tcctcctgtg tcctctgtcc    1450
gctatc                                                               1456
```

<210> SEQ ID NO 2
<211> LENGTH: 383
<212> TYPE: PRT
<213> ORGANISM: Impatiens balsamina

<400> SEQUENCE: 2

```
Met Gly Glu Val Gly Pro Thr Asn Arg Thr Lys Thr Lys Leu Asp Lys
 1               5                  10                  15

Gln Gln Glu Ser Glu Asn Arg Val Pro His Glu Pro Pro Phe Thr
            20                  25                  30

Leu Ser Asp Leu Lys Lys Ala Ile Pro Pro His Cys Phe Glu Arg Ser
        35                  40                  45

Leu Val Lys Ser Phe Tyr His Val Ile His Asp Ile Ile Ile Leu Ser
    50                  55                  60

Phe Phe Tyr Tyr Val Ala Ala Asn Tyr Ile Pro Met Leu Pro Gln Asn
65                  70                  75                  80

Leu Arg Tyr Val Ala Trp Pro Ile Tyr Trp Ala Ile Gln Gly Cys Val
                85                  90                  95

Gln Leu Gly Ile Leu Val Leu Gly His Glu Cys Gly His His Ala Phe
            100                 105                 110

Ser Asp Tyr Gln Trp Val Asp Asp Met Val Gly Phe Val Leu His Ser
        115                 120                 125

Ser Gln Leu Ile Pro Tyr Phe Ser Trp Lys His Ser His Arg Arg His
    130                 135                 140

His Ser Asn Thr Ala Ser Ile Glu Arg Asp Glu Val Tyr Pro Pro Ala
145                 150                 155                 160

Tyr Lys Asn Asp Leu Pro Trp Phe Ala Lys Tyr Leu Arg Asn Pro Val
                165                 170                 175

Gly Arg Phe Leu Met Ile Phe Gly Ala Leu Leu Phe Gly Trp Pro Ser
            180                 185                 190

Tyr Leu Leu Phe Asn Ala Asn Gly Arg Leu Tyr Asp Arg Phe Ala Ser
        195                 200                 205

His Tyr Asp Pro Gln Ser Pro Ile Phe Asn Asn Arg Glu Arg Leu Gln
    210                 215                 220

Val Ile Ala Ser Asp Val Gly Leu Val Phe Ala Tyr Phe Val Leu Tyr
225                 230                 235                 240

Lys Ile Ala Leu Ala Lys Gly Phe Val Trp Leu Ile Cys Val Tyr Gly
                245                 250                 255

Val Pro Tyr Val Ile Leu Asn Gly Leu Ile Val Leu Ile Thr Phe Leu
            260                 265                 270

Gln His Thr His Pro Asn Leu Pro Arg Tyr Asp Leu Ser Glu Trp Asp
        275                 280                 285

Trp Leu Arg Gly Ala Leu Ser Thr Val Asp Arg Asp Tyr Gly Met Leu
    290                 295                 300

Asn Lys Val Phe His Asn Val Thr Asp Thr His Leu Val His His Leu
305                 310                 315                 320

Phe Thr Thr Met Pro His Tyr Arg Ala Lys Glu Ala Thr Glu Val Ile
                325                 330                 335

Lys Pro Ile Leu Gly Asp Tyr Tyr Lys Phe Asp Asp Thr Pro Phe Leu
```

```
                    340                 345                 350
Lys Ala Leu Trp Lys Asp Met Gly Lys Cys Ile Tyr Val Glu Ser Asp
            355                 360                 365
Val Pro Gly Lys Asn Lys Gly Val Tyr Trp Tyr Asn Asn Asp Ile
        370                 375                 380

<210> SEQ ID NO 3
<211> LENGTH: 1308
<212> TYPE: DNA
<213> ORGANISM: Momordica charantia
<220> FEATURE:
<221> NAME/KEY: CDS
<222> LOCATION: (74)..(1273)

<400> SEQUENCE: 3
ccgggctgca ggaattcggc acgagaataa attagcttct tttttttaagt gagtgaaggg      60 agatctggag gca atg ggg ggc aga gga gct att gga gta ctg agg aac         109
            Met Gly Gly Arg Gly Ala Ile Gly Val Leu Arg Asn
              1               5                  10 ggt ggc ggc cca aaa aag aaa atg ggg ccg ggg cag ggg ctg ggg ccg        157
Gly Gly Gly Pro Lys Lys Lys Met Gly Pro Gly Gln Gly Leu Gly Pro
         15                  20                  25 ggg gag cgc att aca cat gcc agg cct ccc ttc agc atc agc cag atc        205
Gly Glu Arg Ile Thr His Ala Arg Pro Pro Phe Ser Ile Ser Gln Ile
     30                  35                  40 aag aag gcc att ccc ccc cac tgc ttt cag cga tcc ctc cgc cgc tct        253
Lys Lys Ala Ile Pro Pro His Cys Phe Gln Arg Ser Leu Arg Arg Ser
 45                  50                  55                  60 ttt tcc tac ctt ctt tcc gac att gcc ctc gtc tct gcc ttt tat tac        301
Phe Ser Tyr Leu Leu Ser Asp Ile Ala Leu Val Ser Ala Phe Tyr Tyr
                 65                  70                  75 gtt gcc gac acc tac ttc cac cgc ctg ccc cac ccc cta ctc cac tac        349
Val Ala Asp Thr Tyr Phe His Arg Leu Pro His Pro Leu Leu His Tyr
             80                  85                  90 ctg gcc tgg ccc gtt tac tgg ttc tgt cag ggc gcc gta ctc acc ggc        397
Leu Ala Trp Pro Val Tyr Trp Phe Cys Gln Gly Ala Val Leu Thr Gly
         95                 100                 105 atg tgg ggc atc gct cac gac tgc ggc cac cac gcc ttc agc gac tac        445
Met Trp Gly Ile Ala His Asp Cys Gly His His Ala Phe Ser Asp Tyr
    110                 115                 120 caa ttg gta gac gac gtg gtt ggg ttc ctc atc cac tct ttg gtt ttt        493
Gln Leu Val Asp Asp Val Val Gly Phe Leu Ile His Ser Leu Val Phe
125                 130                 135                 140 gtc cct tac ttc tcc ttc aag atc agc cac cgc cgc cac cac tcc aac        541
Val Pro Tyr Phe Ser Phe Lys Ile Ser His Arg Arg His His Ser Asn
                145                 150                 155 acc tca tcc gtg gac cgg gac gag gtg ttc gtc ccc aag ccg aag gcc        589
Thr Ser Ser Val Asp Arg Asp Glu Val Phe Val Pro Lys Pro Lys Ala
            160                 165                 170 aaa atg ccc tgg tac ttc aag tac ttg aca aac ccg ccc gcc agg gtc        637
Lys Met Pro Trp Tyr Phe Lys Tyr Leu Thr Asn Pro Pro Ala Arg Val
        175                 180                 185 ttc att att ttt atc acg ctc act ctc ggg tgg cca atg tac ctg acc        685
Phe Ile Ile Phe Ile Thr Leu Thr Leu Gly Trp Pro Met Tyr Leu Thr
    190                 195                 200 ttc aac atc tcc ggc cgg tac tac ggc cgg ttc acc agc cac ttc gac        733
Phe Asn Ile Ser Gly Arg Tyr Tyr Gly Arg Phe Thr Ser His Phe Asp
205                 210                 215                 220 ccg aac agc ccc ata ttc agc cca aag gag cgc gtt ctc gtt cat atc        781
Pro Asn Ser Pro Ile Phe Ser Pro Lys Glu Arg Val Leu Val His Ile
```

```
                    225                 230                 235
tcc aac gct ggg ctt gtg gcg acc ggg tat ttg ctg tac agg atc gca      829
Ser Asn Ala Gly Leu Val Ala Thr Gly Tyr Leu Leu Tyr Arg Ile Ala
        240                 245                 250 atg gcg aag ggg gtg ggg tgg ttg atc cgc ttg tac gga gtg ccg ctg      877
Met Ala Lys Gly Val Gly Trp Leu Ile Arg Leu Tyr Gly Val Pro Leu
            255                 260                 265 atc gtt tta aac gcg tgc gta gtt ctg atc aca gcg ctg cag cac acc      925
Ile Val Leu Asn Ala Cys Val Val Leu Ile Thr Ala Leu Gln His Thr
                270                 275                 280 cac cct tcg ttc ccg tat tac gac tcg acg gaa tgg gat tgg ctg aga      973
His Pro Ser Phe Pro Tyr Tyr Asp Ser Thr Glu Trp Asp Trp Leu Arg
285                 290                 295                 300 ggg aat ctg gtg acg gtg gac aga gat tac ggg cct ata atg aat aga     1021
Gly Asn Leu Val Thr Val Asp Arg Asp Tyr Gly Pro Ile Met Asn Arg
                305                 310                 315 gtg ttt cat cac ata acg gac acg cac gtg gtt cac cat ttg ttt cct     1069
Val Phe His His Ile Thr Asp Thr His Val Val His His Leu Phe Pro
            320                 325                 330 tcg atg ccg cac tac aac ggg aaa gag gcg acg gtt gca gca aag cga     1117
Ser Met Pro His Tyr Asn Gly Lys Glu Ala Thr Val Ala Ala Lys Arg
        335                 340                 345 ata ctg gga gag tac tac cag ttt gat ggg acc cca att tgg aag gcg     1165
Ile Leu Gly Glu Tyr Tyr Gln Phe Asp Gly Thr Pro Ile Trp Lys Ala
    350                 355                 360 gcc tgg agg gaa ttc aga gag tgc gtt tat gta gag cca gac gaa gac     1213
Ala Trp Arg Glu Phe Arg Glu Cys Val Tyr Val Glu Pro Asp Glu Asp
365                 370                 375                 380 gat ggg gcc act tcc ggc tcc agt agt aag ggt gtt ttc tgg tac cac     1261
Asp Gly Ala Thr Ser Gly Ser Ser Ser Lys Gly Val Phe Trp Tyr His
                385                 390                 395 aac aag ctc tga attcaataat atcctctttc acctctcttt ttcat             1308
Asn Lys Leu <210> SEQ ID NO 4
<211> LENGTH: 399
<212> TYPE: PRT
<213> ORGANISM: Momordica charantia

<400> SEQUENCE: 4

Met Gly Gly Arg Gly Ala Ile Gly Val Leu Arg Asn Gly Gly Pro
1               5                   10                  15

Lys Lys Lys Met Gly Pro Gly Gln Gly Leu Gly Pro Gly Glu Arg Ile
            20                  25                  30

Thr His Ala Arg Pro Pro Phe Ser Ile Ser Gln Ile Lys Lys Ala Ile
        35                  40                  45

Pro Pro His Cys Phe Gln Arg Ser Leu Arg Arg Ser Phe Ser Tyr Leu
    50                  55                  60

Leu Ser Asp Ile Ala Leu Val Ser Ala Phe Tyr Tyr Val Ala Asp Thr
65                  70                  75                  80

Tyr Phe His Arg Leu Pro His Pro Leu Leu His Tyr Leu Ala Trp Pro
                85                  90                  95

Val Tyr Trp Phe Cys Gln Gly Ala Val Leu Thr Gly Met Trp Gly Ile
            100                 105                 110

Ala His Asp Cys Gly His His Ala Phe Ser Asp Tyr Gln Leu Val Asp
        115                 120                 125

Asp Val Val Gly Phe Leu Ile His Ser Leu Val Phe Val Pro Tyr Phe
    130                 135                 140
```

```
Ser Phe Lys Ile Ser His Arg Arg His His Ser Asn Thr Ser Ser Val
145                 150                 155                 160

Asp Arg Asp Glu Val Phe Val Pro Lys Pro Lys Ala Lys Met Pro Trp
                165                 170                 175

Tyr Phe Lys Tyr Leu Thr Asn Pro Pro Ala Arg Val Phe Ile Ile Phe
            180                 185                 190

Ile Thr Leu Thr Leu Gly Trp Pro Met Tyr Leu Thr Phe Asn Ile Ser
        195                 200                 205

Gly Arg Tyr Tyr Gly Arg Phe Thr Ser His Phe Asp Pro Asn Ser Pro
    210                 215                 220

Ile Phe Ser Pro Lys Glu Arg Val Leu Val His Ile Ser Asn Ala Gly
225                 230                 235                 240

Leu Val Ala Thr Gly Tyr Leu Leu Tyr Arg Ile Ala Met Ala Lys Gly
                245                 250                 255

Val Gly Trp Leu Ile Arg Leu Tyr Gly Val Pro Leu Ile Val Leu Asn
            260                 265                 270

Ala Cys Val Val Leu Ile Thr Ala Leu Gln His Thr His Pro Ser Phe
        275                 280                 285

Pro Tyr Tyr Asp Ser Thr Glu Trp Asp Trp Leu Arg Gly Asn Leu Val
    290                 295                 300

Thr Val Asp Arg Asp Tyr Gly Pro Ile Met Asn Arg Val Phe His His
305                 310                 315                 320

Ile Thr Asp Thr His Val Val His His Leu Phe Pro Ser Met Pro His
                325                 330                 335

Tyr Asn Gly Lys Glu Ala Thr Val Ala Ala Lys Arg Ile Leu Gly Glu
            340                 345                 350

Tyr Tyr Gln Phe Asp Gly Thr Pro Ile Trp Lys Ala Ala Trp Arg Glu
        355                 360                 365

Phe Arg Glu Cys Val Tyr Val Glu Pro Asp Glu Asp Gly Ala Thr
    370                 375                 380

Ser Gly Ser Ser Ser Lys Gly Val Phe Trp Tyr His Asn Lys Leu
385                 390                 395

<210> SEQ ID NO 5
<211> LENGTH: 387
<212> TYPE: PRT
<213> ORGANISM: Glycine max

<400> SEQUENCE: 5

Met Gly Leu Ala Lys Glu Thr Thr Met Gly Gly Arg Gly Arg Val Ala
 1               5                  10                  15

Lys Val Glu Val Gln Gly Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
```

-continued

```
                  115                 120                 125
Thr Leu His Ser Thr Leu Leu Val Pro Tyr Phe Ser Trp Lys Ile Ser
            130                 135                 140
His Arg Arg His His Ser Asn Thr Gly Ser Leu Asp Arg Asp Glu Val
145                 150                 155                 160
Phe Val Pro Lys Pro Lys Ser Lys Val Ala Trp Phe Ser Lys Tyr Leu
                165                 170                 175
Asn Asn Pro Leu Gly Arg Ala Val Ser Leu Leu Val Thr Leu Thr Ile
            180                 185                 190
Gly Trp Pro Met Tyr Leu Ala Phe Asn Val Ser Gly Arg Pro Tyr Asp
                195                 200                 205
Ser Phe Ala Ser His Tyr His Pro Tyr Ala Pro Ile Tyr Ser Asn Arg
        210                 215                 220
Glu Arg Leu Leu Ile Tyr Val Ser Asp Val Ala Leu Phe Ser Val Thr
225                 230                 235                 240
Tyr Ser Leu Tyr Arg Val Ala Thr Leu Lys Gly Leu Val Trp Leu Leu
                245                 250                 255
Cys Val Tyr Gly Val Pro Leu Leu Ile Val Asn Gly Phe Leu Val Thr
            260                 265                 270
Ile Thr Tyr Leu Gln His Thr His Phe Ala Leu Pro His Tyr Asp Ser
        275                 280                 285
Ser Glu Trp Asp Trp Leu Lys Gly Ala Leu Ala Thr Met Asp Arg Asp
    290                 295                 300
Tyr Gly Ile Leu Asn Lys Val Phe His His Ile Thr Asp Thr His Val
305                 310                 315                 320
Ala His His Leu Phe Ser Thr Met Pro His Tyr His Ala Met Glu Ala
                325                 330                 335
Thr Asn Ala Ile Lys Pro Ile Leu Gly Glu Tyr Tyr Gln Phe Asp Asp
            340                 345                 350
Thr Pro Phe Tyr Lys Ala Leu Trp Arg Glu Ala Arg Glu Cys Leu Tyr
                355                 360                 365
Val Glu Pro Asp Glu Gly Thr Ser Glu Lys Gly Val Tyr Trp Tyr Arg
        370                 375                 380
Asn Lys Tyr
385

<210> SEQ ID NO 6
<211> LENGTH: 387
<212> TYPE: PRT
<213> ORGANISM: Ricinus communis

<400> SEQUENCE: 6

Met Gly Gly Gly Arg Met Ser Thr Val Ile Thr Ser Asn Asn Ser
  1               5                  10                  15
Glu Lys Lys Gly Gly Ser Ser His Leu Lys Arg Ala Pro His Thr Lys
                20                  25                  30
Pro Pro Phe Thr Leu Gly Asp Leu Lys Arg Ala Ile Pro Pro His Cys
            35                  40                  45
Phe Glu Arg Ser Phe Val Arg Ser Phe Ser Tyr Val Ala Tyr Asp Val
        50                  55                  60
Cys Leu Ser Phe Leu Phe Tyr Ser Ile Ala Thr Asn Phe Phe Pro Tyr
65                  70                  75                  80
Ile Ser Ser Pro Leu Ser Tyr Val Ala Trp Leu Val Tyr Trp Leu Phe
                85                  90                  95
```

```
Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 7
<211> LENGTH: 27
<212> TYPE: DNA
<213> ORGANISM: Artificial Sequence
<220> FEATURE:
<223> OTHER INFORMATION: Definition of Artificial Sequence: Impatiens
      balsamina PCR primer

<400> SEQUENCE: 7
aaaaaccatg ggagaagtgg gacccac                                              27

<210> SEQ ID NO 8
<211> LENGTH: 30
<212> TYPE: DNA
<213> ORGANISM: Artificial Sequence
<220> FEATURE:
<223> OTHER INFORMATION: Definition of Artificial Sequence: Impatiens
      balsamina PCR primer
```

-continued

```
<400> SEQUENCE: 8
taattgaatt ccatttcctc ttcaaatgtc                                          30

<210> SEQ ID NO 9
<211> LENGTH: 29
<212> TYPE: DNA
<213> ORGANISM: Artificial Sequence
<220> FEATURE:
<223> OTHER INFORMATION: Definition of Artificial Sequence: Momordica
      charantia PCR primer

<400> SEQUENCE: 9
tttttccatg gggggcagag gagctattg                                           29

<210> SEQ ID NO 10
<211> LENGTH: 30
<212> TYPE: DNA
<213> ORGANISM: Artificial Sequence
<220> FEATURE:
<223> OTHER INFORMATION: Definition of Artificial Sequence: Momordica
      charantia PCR primer

<400> SEQUENCE: 10
gcggccgctt gaattcagag cttgttgtgg                                          30

<210> SEQ ID NO 11
<211> LENGTH: 39
<212> TYPE: DNA
<213> ORGANISM: Artificial Sequence
<220> FEATURE:
<223> OTHER INFORMATION: Definition of Artificial Sequence: Impatiens
      balsamina PCR primer

<400> SEQUENCE: 11
aaggaaaaaa gcggccgcat gggagaagtg ggacccaca                                39

<210> SEQ ID NO 12
<211> LENGTH: 39
<212> TYPE: DNA
<213> ORGANISM: Artificial Sequence
<220> FEATURE:
<223> OTHER INFORMATION: Definition of Artificial Sequence: Impatiens
      balsamina PCR primer

<400> SEQUENCE: 12
aaggaaaaaa gcggccgctc aaatgtcgtt attgtacca                                39

<210> SEQ ID NO 13
<211> LENGTH: 39
<212> TYPE: DNA
<213> ORGANISM: Artificial Sequence
<220> FEATURE:
<223> OTHER INFORMATION: Definition of Artificial Sequence: Momordica
      charantia PCR primer

<400> SEQUENCE: 13
aaggaaaaaa gcggccgcat gggggggcaga ggagctatt                               39

<210> SEQ ID NO 14
<211> LENGTH: 39
<212> TYPE: DNA
<213> ORGANISM: Artificial Sequence
<220> FEATURE:
<223> OTHER INFORMATION: Definition of Artificial Sequence: Momordica
      charantia PCR primer

<400> SEQUENCE: 14
```

```
aaggaaaaaa gcggccgctc agagcttgtt gtggtacca                         39

<210> SEQ ID NO 15
<211> LENGTH: 29
<212> TYPE: DNA
<213> ORGANISM: Artificial Sequence
<220> FEATURE:
<223> OTHER INFORMATION: Definition of Artificial Sequence:
      Chrysobalanus icaco PCR primer

<400> SEQUENCE: 15
tttggatccg tggacgtaat gcgtatcag                                   29

<210> SEQ ID NO 16
<211> LENGTH: 29
<212> TYPE: DNA
<213> ORGANISM: Artificial Sequence
<220> FEATURE:
<223> OTHER INFORMATION: Definition of Artificial Sequence:
      Chrysobalanus icaco PCR primer

<400> SEQUENCE: 16
tttgaattcg ccaccacgcc tttagtgac                                   29

<210> SEQ ID NO 17
<211> LENGTH: 28
<212> TYPE: DNA
<213> ORGANISM: Artificial Sequence
<220> FEATURE:
<223> OTHER INFORMATION: Definition of Artificial Sequence:
      Chrysobalanus icaco PCR primer

<400> SEQUENCE: 17
tttggatccg aaatgggagc aggtggcc                                    28

<210> SEQ ID NO   18
<211> LENGTH: 29
<212> TYPE: DNA
<213> ORGANISM: Artificial Sequence
<220> FEATURE:
<223> OTHER INFORMATION: Definition of Artificial Sequence:
      Chrysobalanus icaco PCR primer

<400> SEQUENCE: 18
tttgagctcg cactcaaaac ttgtcgaac                                   29

<210> SEQ ID NO 19
<211> LENGTH: 1171
<212> TYPE: DNA
<213> ORGANISM: Chrysobalanus icaco
<220> FEATURE:
<221> NAME/KEY: CDS
<222> LOCATION: (4)..(1167)

<400> SEQUENCE: 19 gaa atg gga gca ggt ggc caa aag aca ttc ccc cgc ttg gaa gaa gaa   48
    Met Gly Ala Gly Gly Gln Lys Thr Phe Pro Arg Leu Glu Glu Glu
     1               5                  10                  15 gag aag cag cag cag gcg gca gct gct ggc ttc aag aga atc ccg acc   96
Glu Lys Gln Gln Gln Ala Ala Ala Ala Gly Phe Lys Arg Ile Pro Thr
                 20                  25                  30 acc aag cct cca ttc aca ctc agt gac ctc aag aaa gca atc cca ccc  144
Thr Lys Pro Pro Phe Thr Leu Ser Asp Leu Lys Lys Ala Ile Pro Pro
             35                  40                  45
```

-continued

| | |
|---|---|
| cat tgc ttc cag cgc tcc ctc ctc cgt tct ttc tcc tat gtc ttc att<br>His Cys Phe Gln Arg Ser Leu Leu Arg Ser Phe Ser Tyr Val Phe Ile<br>         50                     55                     60 | 192 |
| gac ctc acc atc atc tct atc ttg ggc tac att ggc gcc acc tat atc<br>Asp Leu Thr Ile Ile Ser Ile Leu Gly Tyr Ile Gly Ala Thr Tyr Ile<br>   65                     70                     75 | 240 |
| tgc ctc ctt cct cct ccg tcc aag tac ctt gct tgg ctt ctc tac tgg<br>Cys Leu Leu Pro Pro Pro Ser Lys Tyr Leu Ala Trp Leu Leu Tyr Trp<br>80                     85                     90                     95 | 288 |
| gct gtt cag ggc tgc ttt ttc acc ggt gct tgg gct ctt gct cat gac<br>Ala Val Gln Gly Cys Phe Phe Thr Gly Ala Trp Ala Leu Ala His Asp<br>                    100                    105                  110 | 336 |
| tgc ggc cac cac gcc ttt agt gac tac cag tgg atc gat gac gcc gtt<br>Cys Gly His His Ala Phe Ser Asp Tyr Gln Trp Ile Asp Asp Ala Val<br>         115                     120                    125 | 384 |
| gga atg gtc ctc cac tcc acg ctt atg gtc cct tac ttc tct ttc aaa<br>Gly Met Val Leu His Ser Thr Leu Met Val Pro Tyr Phe Ser Phe Lys<br>              130                     135                   140 | 432 |
| tac agc cac cgc cgc cat cac tcc aac atc aac tcc ctc gag cgt gac<br>Tyr Ser His Arg Arg His His Ser Asn Ile Asn Ser Leu Glu Arg Asp<br>145                     150                     155 | 480 |
| gaa gtg ttc gtg cca agg ccc aag tcc aag atc aaa tgg tat tgc tcc<br>Glu Val Phe Val Pro Arg Pro Lys Ser Lys Ile Lys Trp Tyr Cys Ser<br>160                     165                     170                   175 | 528 |
| aag tac cta aat aac cca tta ggt cga gtc cta acc ctt gct gtc acc<br>Lys Tyr Leu Asn Asn Pro Leu Gly Arg Val Leu Thr Leu Ala Val Thr<br>              180                     185                   190 | 576 |
| ctc atc ctt gga tgg ccc atg tac tta gcc ttg aat gct tcc ggc cga<br>Leu Ile Leu Gly Trp Pro Met Tyr Leu Ala Leu Asn Ala Ser Gly Arg<br>                   195                     200                  205 | 624 |
| gac tat gac cgc ttt gtg tcc cac ttc tac ccc tat ggc ccc ata tac<br>Asp Tyr Asp Arg Phe Val Ser His Phe Tyr Pro Tyr Gly Pro Ile Tyr<br>              210                     215                    220 | 672 |
| aat gac cgg gaa agg cta cag att tac atc tct gat gcc gga ata ttt<br>Asn Asp Arg Glu Arg Leu Gln Ile Tyr Ile Ser Asp Ala Gly Ile Phe<br>225                     230                     235 | 720 |
| atc gtt agt tat gtg ctc tat cag gtt gct ctg gct aaa ggg ttg ccc<br>Ile Val Ser Tyr Val Leu Tyr Gln Val Ala Leu Ala Lys Gly Leu Pro<br>240                     245                     250                   255 | 768 |
| tgg ctg ata tgc atc tac ggt gtg ccc ttg ttt gtt aac aat gcg ttg<br>Trp Leu Ile Cys Ile Tyr Gly Val Pro Leu Phe Val Asn Asn Ala Leu<br>              260                     265                    270 | 816 |
| gtg gtg acc atc acg tac ctg cag cac act cac ccc gaa ctg ccg cgc<br>Val Val Thr Ile Thr Tyr Leu Gln His Thr His Pro Glu Leu Pro Arg<br>                   275                     280                  285 | 864 |
| tat ggc aac tcc gaa tgg gac tgg ttc aag ggg aca ttg gca acc gtg<br>Tyr Gly Asn Ser Glu Trp Asp Trp Phe Lys Gly Thr Leu Ala Thr Val<br>              290                     295                  300 | 912 |
| gat aga gac atg ggg cct ctg ctc aac tgg gcg aca cat cac gtt tct<br>Asp Arg Asp Met Gly Pro Leu Leu Asn Trp Ala Thr His His Val Ser<br>305                     310                     315 | 960 |
| gat acg cat tac gtc cac cat ctc ttc tcg acc atg ccg cat tat cat<br>Asp Thr His Tyr Val His His Leu Phe Ser Thr Met Pro His Tyr His<br>320                     325                     330                   335 | 1008 |
| gga gtg gaa gct acc aaa gca gtg aag cct atg ctt ggt gag tac tat<br>Gly Val Glu Ala Thr Lys Ala Val Lys Pro Met Leu Gly Glu Tyr Tyr<br>              340                     345                  350 | 1056 |
| agg ttt gat cct act cca cta tac aag gcg cta tgg agg gag gct aag<br>Arg Phe Asp Pro Thr Pro Leu Tyr Lys Ala Leu Trp Arg Glu Ala Lys | 1104 |

-continued

```
                        355                 360                 365
gag tgc ttg ttt gtg gag cct gac tct aag agc cca ggt gtt ttc tgg    1152
Glu Cys Leu Phe Val Glu Pro Asp Ser Lys Ser Pro Gly Val Phe Trp
        370                 375                 380 ttc gac aag ttt tga gtgc                                            1171
Phe Asp Lys Phe
    385
```

<210> SEQ ID NO 20
<211> LENGTH: 387
<212> TYPE: PRT
<213> ORGANISM: Chrysobalanus icaco

<400> SEQUENCE: 20

```
Met Gly Ala Gly Gly Gln Lys Thr Phe Pro Arg Leu Glu Glu Glu
  1               5                  10                  15

Lys Gln Gln Gln Ala Ala Ala Gly Phe Lys Arg Ile Pro Thr Thr
             20                  25                  30

Lys Pro Pro Phe Thr Leu Ser Asp Leu Lys Lys Ala Ile Pro Pro His
         35                  40                  45

Cys Phe Gln Arg Ser Leu Leu Arg Ser Phe Ser Tyr Val Phe Ile Asp
     50                  55                  60

Leu Thr Ile Ile Ser Ile Leu Gly Tyr Ile Gly Ala Thr Tyr Ile Cys
 65                  70                  75                  80

Leu Leu Pro Pro Ser Lys Tyr Leu Ala Trp Leu Leu Tyr Trp Ala
                 85                  90                  95

Val Gln Gly Cys Phe Phe Thr Gly Ala Trp Ala Leu Ala His Asp Cys
                100                 105                 110

Gly His His Ala Phe Ser Asp Tyr Gln Trp Ile Asp Asp Ala Val Gly
            115                 120                 125

Met Val Leu His Ser Thr Leu Met Val Pro Tyr Phe Ser Phe Lys Tyr
    130                 135                 140

Ser His Arg Arg His Ser Asn Ile Asn Ser Leu Glu Arg Asp Glu
145                 150                 155                 160

Val Phe Val Pro Arg Pro Lys Ser Lys Ile Lys Trp Tyr Cys Ser Lys
                165                 170                 175

Tyr Leu Asn Asn Pro Leu Gly Arg Val Leu Thr Leu Ala Val Thr Leu
                180                 185                 190

Ile Leu Gly Trp Pro Met Tyr Leu Ala Leu Asn Ala Ser Gly Arg Asp
            195                 200                 205

Tyr Asp Arg Phe Val Ser His Phe Tyr Pro Tyr Gly Pro Ile Tyr Asn
    210                 215                 220

Asp Arg Glu Arg Leu Gln Ile Tyr Ile Ser Asp Ala Gly Ile Phe Ile
225                 230                 235                 240

Val Ser Tyr Val Leu Tyr Gln Val Ala Leu Ala Lys Gly Leu Pro Trp
                245                 250                 255

Leu Ile Cys Ile Tyr Gly Val Pro Leu Phe Val Asn Asn Ala Leu Val
            260                 265                 270

Val Thr Ile Thr Tyr Leu Gln His Thr His Pro Glu Leu Pro Arg Tyr
        275                 280                 285

Gly Asn Ser Glu Trp Asp Trp Phe Lys Gly Thr Leu Ala Thr Val Asp
    290                 295                 300

Arg Asp Met Gly Pro Leu Leu Asn Trp Ala Thr His His Val Ser Asp
305                 310                 315                 320

Thr His Tyr Val His His Leu Phe Ser Thr Met Pro His Tyr His Gly
```

```
                        325                 330                 335
Val Glu Ala Thr Lys Ala Val Lys Pro Met Leu Gly Glu Tyr Tyr Arg
            340                 345                 350

Phe Asp Pro Thr Pro Leu Tyr Lys Ala Leu Trp Arg Glu Ala Lys Glu
        355                 360                 365

Cys Leu Phe Val Glu Pro Asp Ser Lys Ser Pro Gly Val Phe Trp Phe
    370                 375                 380

Asp Lys Phe
385

<210> SEQ ID NO 21
<211> LENGTH: 31
<212> TYPE: DNA
<213> ORGANISM: Artificial Sequence
<220> FEATURE:
<223> OTHER INFORMATION: Definition of Artificial Sequence:
      Chrysobalanus icaco PCR primer

<400> SEQUENCE: 21
tatgcggccg cgaaatggga gcaggtggcc c                              31

<210> SEQ ID NO 22
<211> LENGTH: 31
<212> TYPE: DNA
<213> ORGANISM: Artificial Sequence
<220> FEATURE:
<223> OTHER INFORMATION: Definition of Artificial Sequence:
      Chrysobalanus icaco PCR primer

<400> SEQUENCE: 22
tatgcggccg cgcactcaaa acttgtcgaa c                              31

<210> SEQ ID NO 23
<211> LENGTH: 1164
<212> TYPE: DNA
<213> ORGANISM: Licania michauxii
<220> FEATURE:
<221> NAME/KEY: CDS
<222> LOCATION: (1)..(1164)

<400> SEQUENCE: 23 atg gga gca ggt ggc caa aag aca tgc ccc cgc ttg gtg gaa gaa gag    48
Met Gly Ala Gly Gly Gln Lys Thr Cys Pro Arg Leu Val Glu Glu Glu
 1               5                  10                  15 aag cag cag cag gcg gca gct gct ggc ttc aag aga atc ccg acc acc    96
Lys Gln Gln Gln Ala Ala Ala Ala Gly Phe Lys Arg Ile Pro Thr Thr
             20                  25                  30 aaa cct cca ttc aca ctc agc gac ctc aag aaa gca atc cca ccc cat   144
Lys Pro Pro Phe Thr Leu Ser Asp Leu Lys Lys Ala Ile Pro Pro His
         35                  40                  45 tgc ttc cag cgc tcc ctc ctc cgt tct ttc tcc tat gtc ttc att gac   192
Cys Phe Gln Arg Ser Leu Leu Arg Ser Phe Ser Tyr Val Phe Ile Asp
     50                  55                  60 ctc acc atc atc tct atc ttg ggc tac att gcc gcc acc tat atc tac   240
Leu Thr Ile Ile Ser Ile Leu Gly Tyr Ile Ala Ala Thr Tyr Ile Tyr
 65                  70                  75                  80 ctc ctt cct cct ccg tcc aag tac ctt gct tgg ctt ctg tac tgg gct   288
Leu Leu Pro Pro Pro Ser Lys Tyr Leu Ala Trp Leu Leu Tyr Trp Ala
                 85                  90                  95 gtt cag ggc tgc ttt ttc acc ggt gct tgg gct ctt gcc cat gac tgc   336
Val Gln Gly Cys Phe Phe Thr Gly Ala Trp Ala Leu Ala His Asp Cys
            100                 105                 110
```

| | | |
|---|---|---|
| ggc cac cac gcc ttt agt gac tac cag tgg gtc gat gac gcc gtt gga<br>Gly His His Ala Phe Ser Asp Tyr Gln Trp Val Asp Asp Ala Val Gly<br>     115                    120                   125 | | 384 |
| atg gtc ctc cac tcc gcg ctc atg gtc cct tac ttc tct ttc aaa tac<br>Met Val Leu His Ser Ala Leu Met Val Pro Tyr Phe Ser Phe Lys Tyr<br>130                    135                   140 | | 432 |
| agc cac cgc cgc cat cac tcc aac atc aac tct ctc gag cgt gac gaa<br>Ser His Arg Arg His His Ser Asn Ile Asn Ser Leu Glu Arg Asp Glu<br>145                    150                  155                 160 | | 480 |
| gtg ttc gtg cca agg ccc aag ttc aag atc aaa tgg tat tgc tcc aag<br>Val Phe Val Pro Arg Pro Lys Phe Lys Ile Lys Trp Tyr Cys Ser Lys<br>                165                  170                 175 | | 528 |
| tac cta aat aac cca tta ggt cga gtc cta acc ctt gcg gtc acc ctc<br>Tyr Leu Asn Asn Pro Leu Gly Arg Val Leu Thr Leu Ala Val Thr Leu<br>           180                    185                 190 | | 576 |
| atc ctt gga tgg ccc atg tac tta gcc ttc aat gct tct ggc cga gac<br>Ile Leu Gly Trp Pro Met Tyr Leu Ala Phe Asn Ala Ser Gly Arg Asp<br>                195                  200                 205 | | 624 |
| tat gac cgc ttt gtg tcc cac ttc tac ccc tat ggc ccc att tac aat<br>Tyr Asp Arg Phe Val Ser His Phe Tyr Pro Tyr Gly Pro Ile Tyr Asn<br>210                    215                  220 | | 672 |
| gac cgg gaa aga ctc cag att tac atc tct gat gcc gga ata ttt ata<br>Asp Arg Glu Arg Leu Gln Ile Tyr Ile Ser Asp Ala Gly Ile Phe Ile<br>225                    230                  235                 240 | | 720 |
| gtt agt tat gtg ctc tat cag gtt gct ctg gct aaa ggg ttg ccc tgg<br>Val Ser Tyr Val Leu Tyr Gln Val Ala Leu Ala Lys Gly Leu Pro Trp<br>                245                  250                 255 | | 768 |
| ctg ata tgc atc tac ggt gtg ccc ttg ttt gtt aac aat gcg ttg gtc<br>Leu Ile Cys Ile Tyr Gly Val Pro Leu Phe Val Asn Asn Ala Leu Val<br>           260                    265                 270 | | 816 |
| gtg acc atc acg tac ctg cag cac act cac cct gaa ctg ccg cgc tat<br>Val Thr Ile Thr Tyr Leu Gln His Thr His Pro Glu Leu Pro Arg Tyr<br>                275                  280                 285 | | 864 |
| ggc aac tcc gaa tgg gac tgg ttc aag ggg aca ttg gca acc gtg gat<br>Gly Asn Ser Glu Trp Asp Trp Phe Lys Gly Thr Leu Ala Thr Val Asp<br>           290                    295                 300 | | 912 |
| aga gac atg ggg cct ctg ctc aac tgg gtg aca cat cac gtt tct gat<br>Arg Asp Met Gly Pro Leu Leu Asn Trp Val Thr His His Val Ser Asp<br>305                    310                  315                 320 | | 960 |
| acg cat tac gtc cac cat ctc ttc tcg acc atg ccg cat tat cat gga<br>Thr His Tyr Val His His Leu Phe Ser Thr Met Pro His Tyr His Gly<br>                325                  330                 335 | | 1008 |
| gtg gaa gct acc aaa gct gtg aag ccg atg ctt ggt gag tac tac agg<br>Val Glu Ala Thr Lys Ala Val Lys Pro Met Leu Gly Glu Tyr Tyr Arg<br>           340                    345                 350 | | 1056 |
| ttt gat cct act cca gtg tac aag gca cta tgg agg gag gct aag gag<br>Phe Asp Pro Thr Pro Val Tyr Lys Ala Leu Trp Arg Glu Ala Lys Glu<br>                355                  360                 365 | | 1104 |
| tgc ttg ttt gtg gag cct gac tct aag agc cca ggt gtc ttc tgg ttc<br>Cys Leu Phe Val Glu Pro Asp Ser Lys Ser Pro Gly Val Phe Trp Phe<br>370                    375                  380 | | 1152 |
| gac aag ttt tga<br>Asp Lys Phe<br>385 | | 1164 |

<210> SEQ ID NO 24
<211> LENGTH: 387
<212> TYPE: PRT
<213> ORGANISM: Licania michauxii

<400> SEQUENCE: 24

```
Met Gly Ala Gly Gly Gln Lys Thr Cys Pro Arg Leu Val Glu Glu
 1               5                  10                 15

Lys Gln Gln Gln Ala Ala Ala Gly Phe Lys Arg Ile Pro Thr Thr
            20                  25                  30

Lys Pro Pro Phe Thr Leu Ser Asp Leu Lys Lys Ala Ile Pro Pro His
            35                  40                  45

Cys Phe Gln Arg Ser Leu Leu Arg Ser Phe Ser Tyr Val Phe Ile Asp
 50                  55                  60

Leu Thr Ile Ile Ser Ile Leu Gly Tyr Ile Ala Thr Tyr Ile Tyr
 65                  70                  75                  80

Leu Leu Pro Pro Ser Lys Tyr Leu Ala Trp Leu Tyr Trp Ala
                85                  90                  95

Val Gln Gly Cys Phe Phe Thr Gly Ala Trp Ala Leu Ala His Asp Cys
            100                 105                 110

Gly His His Ala Phe Ser Asp Tyr Gln Trp Val Asp Asp Ala Val Gly
            115                 120                 125

Met Val Leu His Ser Ala Leu Met Val Pro Tyr Phe Ser Phe Lys Tyr
 130                 135                 140

Ser His Arg Arg His His Ser Asn Ile Asn Ser Leu Glu Arg Asp Glu
145                 150                 155                 160

Val Phe Val Pro Arg Pro Lys Phe Lys Ile Lys Trp Tyr Cys Ser Lys
                165                 170                 175

Tyr Leu Asn Asn Pro Leu Gly Arg Val Leu Thr Leu Ala Val Thr Leu
                180                 185                 190

Ile Leu Gly Trp Pro Met Tyr Leu Ala Phe Asn Ala Ser Gly Arg Asp
            195                 200                 205

Tyr Asp Arg Phe Val Ser His Phe Tyr Pro Tyr Gly Pro Ile Tyr Asn
 210                 215                 220

Asp Arg Glu Arg Leu Gln Ile Tyr Ile Ser Asp Ala Gly Ile Phe Ile
225                 230                 235                 240

Val Ser Tyr Val Leu Tyr Gln Val Ala Leu Ala Lys Gly Leu Pro Trp
            245                 250                 255

Leu Ile Cys Ile Tyr Gly Val Pro Leu Phe Val Asn Asn Ala Leu Val
            260                 265                 270

Val Thr Ile Thr Tyr Leu Gln His Thr His Pro Glu Leu Pro Arg Tyr
 275                 280                 285

Gly Asn Ser Glu Trp Asp Trp Phe Lys Gly Thr Leu Ala Thr Val Asp
 290                 295                 300

Arg Asp Met Gly Pro Leu Leu Asn Trp Val Thr His His Val Ser Asp
305                 310                 315                 320

Thr His Tyr Val His His Leu Phe Ser Thr Met Pro His Tyr His Gly
                325                 330                 335

Val Glu Ala Thr Lys Ala Val Lys Pro Met Leu Gly Glu Tyr Tyr Arg
            340                 345                 350

Phe Asp Pro Thr Pro Val Tyr Lys Ala Leu Trp Arg Glu Ala Lys Glu
            355                 360                 365

Cys Leu Phe Val Glu Pro Asp Ser Lys Ser Pro Gly Val Phe Trp Phe
 370                 375                 380

Asp Lys Phe
385

<210> SEQ ID NO 25
<211> LENGTH: 31
```

```
<212> TYPE: DNA
<213> ORGANISM: Artificial Sequence
<220> FEATURE:
<223> OTHER INFORMATION: Definition of Artificial Sequence: PCR primer
      for KAIPPHCF

<400> SEQUENCE: 25
ttgaattcaa rgcnathccn ccncaytgyt t                              31

<210> SEQ ID NO 26
<211> LENGTH: 27
<212> TYPE: DNA
<213> ORGANISM: Artificial Sequence
<220> FEATURE:
<223> OTHER INFORMATION: Definition of Sequence: antisense PCR primer
      for EWDW(L/F)RG

<400> SEQUENCE: 26
ttgaattccn cknarccart cccaytc                                   27

<210> SEQ ID NO 27
<211> LENGTH: 765
<212> TYPE: DNA
<213> ORGANISM: Aleurites fordii
<220> FEATURE:
<221> NAME/KEY: CDS
<222> LOCATION: (1)..(765)

<400> SEQUENCE: 27
```

| | | | | | | | | | | | | | | | | |
|---|---|---|---|---|---|---|---|---|---|---|---|---|---|---|---|---|
| aag | gcg | ata | cca | ccg | cat | tgc | ttc | cag | cgt | tct | gtc | ctc | cgt | tca | ttc | 48 |
| Lys | Ala | Ile | Pro | Pro | His | Cys | Phe | Gln | Arg | Ser | Val | Leu | Arg | Ser | Phe | |
| 1 | | | | 5 | | | | | 10 | | | | | 15 | | |
| tca | tat | gtt | gtt | tat | gac | ctg | acc | gtg | gcc | ttt | atc | ttc | tat | tat | att | 96 |
| Ser | Tyr | Val | Val | Tyr | Asp | Leu | Thr | Val | Ala | Phe | Ile | Phe | Tyr | Tyr | Ile | |
| | | | 20 | | | | | 25 | | | | | 30 | | | |
| gcc | acc | aat | tac | ttc | cac | ctc | ctt | cct | caa | cct | ctc | tct | tat | gtg | gcc | 144 |
| Ala | Thr | Asn | Tyr | Phe | His | Leu | Leu | Pro | Gln | Pro | Leu | Ser | Tyr | Val | Ala | |
| | | 35 | | | | | 40 | | | | | 45 | | | | |
| tgg | cca | att | tac | tgg | gcc | ctt | cag | ggc | tgt | gtc | ctc | act | ggc | gtt | tgg | 192 |
| Trp | Pro | Ile | Tyr | Trp | Ala | Leu | Gln | Gly | Cys | Val | Leu | Thr | Gly | Val | Trp | |
| | 50 | | | | | 55 | | | | | 60 | | | | | |
| gtt | ata | gca | cat | gag | tgt | gga | cat | cat | gcc | ttc | agt | gac | tat | caa | ttg | 240 |
| Val | Ile | Ala | His | Glu | Cys | Gly | His | His | Ala | Phe | Ser | Asp | Tyr | Gln | Leu | |
| 65 | | | | | 70 | | | | | 75 | | | | | 80 | |
| ctt | gat | gac | att | gtt | ggc | ctt | gtc | ctc | cat | tcc | tgt | ctt | ctt | gtc | cct | 288 |
| Leu | Asp | Asp | Ile | Val | Gly | Leu | Val | Leu | His | Ser | Cys | Leu | Leu | Val | Pro | |
| | | | | 85 | | | | | 90 | | | | | 95 | | |
| tac | ttt | tca | tgg | aaa | cat | agc | cac | cgc | gtt | cac | cac | tct | aac | aca | gct | 336 |
| Tyr | Phe | Ser | Trp | Lys | His | Ser | His | Arg | Val | His | His | Ser | Asn | Thr | Ala | |
| | | | 100 | | | | | 105 | | | | | 110 | | | |
| tcc | ctt | gag | cga | gat | gaa | gtg | ttt | gtc | ccc | aag | aag | aaa | tct | agc | atc | 384 |
| Ser | Leu | Glu | Arg | Asp | Glu | Val | Phe | Val | Pro | Lys | Lys | Lys | Ser | Ser | Ile | |
| | | 115 | | | | | 120 | | | | | 125 | | | | |
| cgc | tgg | ttc | tct | aaa | tac | ctt | aac | aac | cca | cca | ggc | cgt | cta | ttt | aca | 432 |
| Arg | Trp | Phe | Ser | Lys | Tyr | Leu | Asn | Asn | Pro | Pro | Gly | Arg | Leu | Phe | Thr | |
| | 130 | | | | | 135 | | | | | 140 | | | | | |
| ctt | acc | atc | aca | ctt | acc | ctt | ggc | tgg | cct | cta | tac | cta | gct | ttc | aat | 480 |
| Leu | Thr | Ile | Thr | Leu | Thr | Leu | Gly | Trp | Pro | Leu | Tyr | Leu | Ala | Phe | Asn | |
| 145 | | | | | 150 | | | | | 155 | | | | | 160 | |
| gtt | tca | ggc | agg | cct | tat | gat | cgg | ttc | gcc | tgt | cac | tat | gac | cca | tat | 528 |
| Val | Ser | Gly | Arg | Pro | Tyr | Asp | Arg | Phe | Ala | Cys | His | Tyr | Asp | Pro | Tyr | |
| | | | | 165 | | | | | 170 | | | | | 175 | | |
| ggg | cct | atc | tat | act | gat | cgt | gag | cga | act | gaa | ata | tac | atc | tct | gat | 576 |

```
                                                         -continued

Gly Pro Ile Tyr Thr Asp Arg Glu Arg Thr Glu Ile Tyr Ile Ser Asp
            180                 185                 190 gct ggt gtt ctt gct gtc act ttt ggt ctc tac cgt ctt gct gca gca       624
Ala Gly Val Leu Ala Val Thr Phe Gly Leu Tyr Arg Leu Ala Ala Ala
            195                 200                 205 aag ggg ctt gct tgg gtt att tgt gtt tat gga gta cca ttg tta att       672
Lys Gly Leu Ala Trp Val Ile Cys Val Tyr Gly Val Pro Leu Leu Ile
        210                 215                 220 gtg aat gca ttt cta gtt atg ata aca tat ttg cag cat act cat cct       720
Val Asn Ala Phe Leu Val Met Ile Thr Tyr Leu Gln His Thr His Pro
225                 230                 235                 240 tca ata cca cat tat gat tct tcc gag tgg gac tgg ctc cgt gga           765
Ser Ile Pro His Tyr Asp Ser Ser Glu Trp Asp Trp Leu Arg Gly
                245                 250                 255

<210> SEQ ID NO 28
<211> LENGTH: 255
<212> TYPE: PRT
<213> ORGANISM: Aleurites fordii

<400> SEQUENCE: 28

Lys Ala Ile Pro Pro His Cys Phe Gln Arg Ser Val Leu Arg Ser Phe
  1               5                  10                  15

Ser Tyr Val Val Tyr Asp Leu Thr Val Ala Phe Ile Phe Tyr Tyr Ile
             20                  25                  30

Ala Thr Asn Tyr Phe His Leu Leu Pro Gln Pro Leu Ser Tyr Val Ala
         35                  40                  45

Trp Pro Ile Tyr Trp Ala Leu Gln Gly Cys Val Leu Thr Gly Val Trp
     50                  55                  60

Val Ile Ala His Glu Cys Gly His His Ala Phe Ser Asp Tyr Gln Leu
 65                  70                  75                  80

Leu Asp Asp Ile Val Gly Leu Val Leu His Ser Cys Leu Leu Val Pro
                 85                  90                  95

Tyr Phe Ser Trp Lys His Ser His Arg Arg His Ser Asn Thr Ala
            100                 105                 110

Ser Leu Glu Arg Asp Glu Val Phe Val Pro Lys Lys Ser Ser Ile
        115                 120                 125

Arg Trp Phe Ser Lys Tyr Leu Asn Asn Pro Pro Gly Arg Leu Phe Thr
130                 135                 140

Leu Thr Ile Thr Leu Thr Leu Gly Trp Pro Leu Tyr Leu Ala Phe Asn
145                 150                 155                 160

Val Ser Gly Arg Pro Tyr Asp Arg Phe Ala Cys His Tyr Asp Pro Tyr
                165                 170                 175

Gly Pro Ile Tyr Thr Asp Arg Glu Arg Thr Glu Ile Tyr Ile Ser Asp
            180                 185                 190

Ala Gly Val Leu Ala Val Thr Phe Gly Leu Tyr Arg Leu Ala Ala Ala
        195                 200                 205

Lys Gly Leu Ala Trp Val Ile Cys Val Tyr Gly Val Pro Leu Leu Ile
    210                 215                 220

Val Asn Ala Phe Leu Val Met Ile Thr Tyr Leu Gln His Thr His Pro
225                 230                 235                 240

Ser Ile Pro His Tyr Asp Ser Ser Glu Trp Asp Trp Leu Arg Gly
                245                 250                 255

<210> SEQ ID NO 29
<211> LENGTH: 765
<212> TYPE: DNA
```

<213> ORGANISM: Aleurites fordii
<220> FEATURE:
<221> NAME/KEY: CDS
<222> LOCATION: (1)..(765)

<400> SEQUENCE: 29

```
aag gcg ata cca cct cat tgt ttt aaa cgc tcc ctt ctt cgc tcc ttc       48
Lys Ala Ile Pro Pro His Cys Phe Lys Arg Ser Leu Leu Arg Ser Phe
  1               5                  10                  15 tct tat gtt gtt tat gac ctt tct tta agt ttt att ttc tac tcc att       96
Ser Tyr Val Val Tyr Asp Leu Ser Leu Ser Phe Ile Phe Tyr Ser Ile
             20                  25                  30 gcc acc acc tac ttc cat ctc ctc cct tct ccg ata acc tac atc gct      144
Ala Thr Thr Tyr Phe His Leu Leu Pro Ser Pro Ile Thr Tyr Ile Ala
         35                  40                  45 tgg cct gtc tac tgg gct ttc caa ggc tgc att ctc act agt gtt tgg      192
Trp Pro Val Tyr Trp Ala Phe Gln Gly Cys Ile Leu Thr Ser Val Trp
     50                  55                  60 gtg ctc ggc cat gaa tgt ggt cac cat gct ttt agc gaa tat aat tgg      240
Val Leu Gly His Glu Cys Gly His His Ala Phe Ser Glu Tyr Asn Trp
 65                  70                  75                  80 ctt gat gac act att ggc cta att ctc cac tct tca ctt cta gtt cca      288
Leu Asp Asp Thr Ile Gly Leu Ile Leu His Ser Ser Leu Leu Val Pro
                 85                  90                  95 tac ttt tca ttt aaa att agc cat cgt cgc cat cac tct aac att gca      336
Tyr Phe Ser Phe Lys Ile Ser His Arg Arg His His Ser Asn Ile Ala
            100                 105                 110 tca ctt gaa cgc gac gag gtg ttt gtc cct agg ctc aag tct gca att      384
Ser Leu Glu Arg Asp Glu Val Phe Val Pro Arg Leu Lys Ser Ala Ile
        115                 120                 125 cca tgg tat tcc aag tac ctc aac aac cca cca ggc cga gct tta acc      432
Pro Trp Tyr Ser Lys Tyr Leu Asn Asn Pro Pro Gly Arg Ala Leu Thr
    130                 135                 140 ctt gta gct aca ctc ttc att ggc tgg cct tta tat tta gcc ttc aat      480
Leu Val Ala Thr Leu Phe Ile Gly Trp Pro Leu Tyr Leu Ala Phe Asn
145                 150                 155                 160 gtt tcg ggc cga tac tat gat cgc ttt gcc tgc cat tat gat cct tat      528
Val Ser Gly Arg Tyr Tyr Asp Arg Phe Ala Cys His Tyr Asp Pro Tyr
                165                 170                 175 agt cct ata tat tct gat aga gaa agg ctt cag att tac att tct gat      576
Ser Pro Ile Tyr Ser Asp Arg Glu Arg Leu Gln Ile Tyr Ile Ser Asp
            180                 185                 190 gct atg att ttc gtt gca gct tat gtg ttg tat aag att gcc atg gca      624
Ala Met Ile Phe Val Ala Ala Tyr Val Leu Tyr Lys Ile Ala Met Ala
        195                 200                 205 aaa ggg cta gca tgg ctg gta tgt atc tat ggg gta cca ttg ctt att      672
Lys Gly Leu Ala Trp Leu Val Cys Ile Tyr Gly Val Pro Leu Leu Ile
    210                 215                 220 gtt aat gct ctt gtt gtg act atc aca tcc ttg cag cac acc cac gtt      720
Val Asn Ala Leu Val Val Thr Ile Thr Ser Leu Gln His Thr His Val
225                 230                 235                 240 gca ttg cca cat tat gac tcc tca gag tgg gac tgg ctc cgc gga           765
Ala Leu Pro His Tyr Asp Ser Ser Glu Trp Asp Trp Leu Arg Gly
                245                 250                 255
```

<210> SEQ ID NO 30
<211> LENGTH: 255
<212> TYPE: PRT
<213> ORGANISM: Aleurites fordii

<400> SEQUENCE: 30

-continued

```
Lys Ala Ile Pro Pro His Cys Phe Lys Arg Ser Leu Arg Ser Phe
 1               5                  10                  15

Ser Tyr Val Val Tyr Asp Leu Ser Leu Ser Phe Ile Phe Tyr Ser Ile
                 20                  25                  30

Ala Thr Thr Tyr Phe His Leu Leu Pro Ser Pro Ile Thr Tyr Ile Ala
             35                  40                  45

Trp Pro Val Tyr Trp Ala Phe Gln Gly Cys Ile Leu Thr Ser Val Trp
 50                  55                      60

Val Leu Gly His Glu Cys Gly His His Ala Phe Ser Glu Tyr Asn Trp
 65              70                  75                      80

Leu Asp Asp Thr Ile Gly Leu Ile Leu His Ser Ser Leu Leu Val Pro
                 85                  90                  95

Tyr Phe Ser Phe Lys Ile Ser Arg Arg His His Ser Asn Ile Ala
                100              105                 110

Ser Leu Glu Arg Asp Glu Val Phe Val Pro Arg Leu Lys Ser Ala Ile
             115                 120                 125

Pro Trp Tyr Ser Lys Tyr Leu Asn Asn Pro Pro Gly Arg Ala Leu Thr
             130                 135                 140

Leu Val Ala Thr Leu Phe Ile Gly Trp Pro Leu Tyr Leu Ala Phe Asn
145                 150                 155                 160

Val Ser Gly Arg Tyr Tyr Asp Arg Phe Ala Cys His Tyr Asp Pro Tyr
                 165                 170                 175

Ser Pro Ile Tyr Ser Asp Arg Glu Arg Leu Gln Ile Tyr Ile Ser Asp
             180                 185                 190

Ala Met Ile Phe Val Ala Ala Tyr Val Leu Tyr Lys Ile Ala Met Ala
             195                 200                 205

Lys Gly Leu Ala Trp Leu Val Cys Ile Tyr Gly Val Pro Leu Leu Ile
 210                 215                 220

Val Asn Ala Leu Val Val Thr Ile Thr Ser Leu Gln His Thr His Val
225                 230                 235                 240

Ala Leu Pro His Tyr Asp Ser Ser Glu Trp Asp Trp Leu Arg Gly
                 245                 250                 255
```

<210> SEQ ID NO 31
<211> LENGTH: 38
<212> TYPE: DNA
<213> ORGANISM: Artificial Sequence
<220> FEATURE:
<223> OTHER INFORMATION: Definition of Artificial Sequence: PCR primer
      for KKAIPPHCF
<220> FEATURE:
<221> NAME/KEY: modified base
<222> LOCATION: (15)
<223> OTHER INFORMATION: inosine
<220> FEATURE:
<221> NAME/KEY: unsure
<222> LOCATION: (21)
<223> OTHER INFORMATION: this nucleotide can be A, C, G, or T
<220> FEATURE:
<221> NAME/KEY: unsure
<222> LOCATION: (27)
<223> OTHER INFORMATION: this nucleotide can be A, C, G, or T
<220> FEATURE:
<221> NAME/KEY: unsure
<222> LOCATION: (30)
<223> OTHER INFORMATION: this nucleotide can be A, C, G, or T

<400> SEQUENCE: 31
tatctagagc tcaanaargc nathccnccn caytgytt         38

<210> SEQ ID NO 32

```
<211> LENGTH: 33
<212> TYPE: DNA
<213> ORGANISM: Artificial Sequence
<220> FEATURE:
<223> OTHER INFORMATION: Definition of Sequence: antisense PCR primer
      for WREAKEC
<220> FEATURE:
<221> NAME/KEY: unsure
<222> LOCATION: (24)
<223> OTHER INFORMATION: this nucleotide can be A, C, G, or T
<220> FEATURE:
<221> NAME/KEY: unsure
<222> LOCATION: (30)
<223> OTHER INFORMATION: this nucleotide can be A, C, G, or T

<400> SEQUENCE: 32
taagatctgt atacrcaytc yttngcytcn ckc                              33

<210> SEQ ID NO 33
<211> LENGTH: 25
<212> TYPE: DNA
<213> ORGANISM: Artificial Sequence
<220> FEATURE:
<223> OTHER INFORMATION: Definition of Artificial Sequence: Licania
      michauxii PCR primer

<400> SEQUENCE: 33
tttccatgga gcaggtggcc aaaag                                       25

<210> SEQ ID NO 34
<211> LENGTH: 29
<212> TYPE: DNA
<213> ORGANISM: Artificial Sequence
<220> FEATURE:
<223> OTHER INFORMATION: Definition of Artificial Sequence: Licania
      michauxii PCR primer

<400> SEQUENCE: 34
tttagatctg cactcaaaac ttgtcgaac                                   29
```

US 7,244,563 B2

GENES FOR PLANT FATTY ACID MODIFYING ENZYMES ASSOCIATED WITH CONJUGATED DOUBLE BOND FORMATION

FIELD OF THE INVENTION

This invention relates to fatty acid biosynthesis and, in particular, to the preparation and use of nucleic acid fragments encoding plant fatty acid modifying enzymes associated with conjugated double bond formation. Chimeric genes incorporating such nucleic acid fragments or functionally equivalent subfragments thereof and suitable regulatory sequences can be used to create transgenic plants having altered lipid profiles.

BACKGROUND OF THE INVENTION

Fatty acids bearing chemical modifications in addition to the common double bonds are found in the storage lipids of many oilseeds (Harwood, J. L. (1980) In The Biochemistry of Plants, T. S. Moore Jr., ed. CRC Press, New York, pp 91–116). Some of these modifications functionalize the fatty acid to produce products that are useful in industrial applications; this is opposed to the more common usage of plant-derived lipids as foods. Examples are the use of the hydroxylated fatty acid ricinoleic acid in lubricants, and the short- or medium-carbon chain length fatty acids from palm oil in detergents. In some cases, fatty acid composition of the storage lipids of oilseeds produced in temperate climates can be modified by the addition of genes from exotic sources so that large amounts of unique fatty acids are produced (Ohlrogge, J. B. (1994) Plant Physiol. 104, 821–826).

Fatty acids containing conjugated double bonds are major components of the seed oil of a limited number of plant species. For example, α-parinaric acid (9-cis, 11-trans, 13-trans, 15-cis-octadecatetraenoic acid) and β-parinaric acid (9-trans, 11-trans, 13-trans, 15-cis-octadecatetraenoic acid) compose more than 25% of the total fatty acids of the seed oil of Impatiens species (Bagby, M. O., Smith, C. R. and Wolff, I. A. (1966) Lipids 1, 263–267). In addition, α-eleostearic acid (9-cis, 11-trans, 13-trans-octadecatrienoic acid) and β-eleostearic acid (9-trans, 11-trans, 13-trans-octadecatrienoic acid) compose >55% of the total fatty acids of the seed oil of Momordica charantia (Chisolm, M. J. and Hopkins, C. Y. (1964) Can. J. Biochem. 42, 560–564; Liu, L., Hammond, E. G. and Nikolau, B. J. (1997) Plant Physiol. 113, 1343–1349).

The presence of conjugated double bonds in fatty acids provides the functional basis for drying oils such as tung oil that are enriched in isomers of eleostearic acid. This is due largely to the fact that fatty acids with conjugated double bonds display high rates of oxidation, particularly when compared to polyunsaturated fatty acids with methylene interrupted double bonds. Drying oils, such as tung oil, are used as components of paints, varnishes, and inks.

Conjugated fatty acids can also be used as an animal feed additive. Conjugated linoleic acids (CLAs, 18:2) have been used to improve fat composition in feed animals.

U.S. Pat. No. 5,581,572, issued to Cook et al. on Dec. 22, 1998, describes a method of increasing fat firmness and improving meat quality in animals using conjugated linoleic acds.

U.S. Pat. No. 5,554,646, issued to Cook et al. on Sep. 10, 1996, describes a method of reducing body fat in animals using conjugated linoleic acids.

U.S. Pat. No. 5,519,451, issued to Cook et al. on Jul. 6, 1999, describes a method of improving the growth or the efficiency of feed conversion of an animal which involves animal feed particles having an inner core of nutrients and an outer layer containing a conjugated fatty acid or an antibody that can protect the animal from contacting diseases that can adversely affect the animal's ability to grow or efficiently convert its feed into body tissue.

U.S. Pat. No. 5,428,072, issued to Cook et al. on Jun. 27, 1995, describes a method of enhancing weight gain and feed efficienty in animal which involves the use of conjugated linoleic acid.

The mechanism by which these effects are realized is not known. It is believed that no one heretofore has discussed the use of conjugated 18:3 fatty acids (conjugated linolenic acids or ClnAs), for improving animal carcass characteristics.

The biosynthesis of fatty acids with conjugated double bonds is not well understood. Several reports have indicated that conjugated double bonds are formed by modification of an existing double bond (Crombie, L. and Holloway, S. J. (1985) J. Chem. Soc. Perkins Trans. I 1985, 2425–2434; Liu, L., Hammond, E. G. and Nikolau, B. J. (1997) Plant Physiol. 113, 1343–1349). For example, the double bonds at the 11 and 13 carbon atoms in eleostearic acid have been shown to arise from the modification of the $\Delta^{12}$ double bond of linoleic acid (18:2$\Delta^{9,12}$) (Liu, L., Hammond, E. G. and Nikolau, B. J. (1997) Plant Physiol. 113, 1343–1349). The exact mechanism involved in conjugated double formation in fatty acids, however, has not yet been determined. Thus, while candidate enzyme classes have been suggested, no gene sequences have been isolated from those candidate classes and from tissues that are known to produce fatty acids with conjugated double bonds.

SUMMARY OF THE INVENTION

This invention concerns an isolated nucleic acid fragment encoding a plant fatty acid modifying enzyme associated with conjugated double bond formation wherein said fragment or a functionally equivalent subfragment thereof (a) hybridizes to any of the nucleotide sequences set forth in SEQ ID NOS:1, 3, 19, 23, or 29 under conditions of moderate stringency or (b) is at least 45% identical to a polypeptide encoded by any of the nucleotide sequences set forth in SEQ ID NOS:1, 3, 19, 23, or 29 or a functionally equivalent subfragment thereof as determined by a comparison method designed to detect homologous sequences.

In a second aspect, this invention concerns an isolated nucleic acid fragment encoding a plant fatty acid modifying enzyme associated with conjugated double bond formation wherein said fragment or a functionally equivalent subfragment thereof encodes a protein comprising any one of the amino acid sequences set forth in SEQ ID NOS:2, 4, 20, 24, or 30.

In a third aspect, this invention concerns a chimeric gene comprising such isolated nucleic acid fragments or a functionally equivalent subfragment thereof or a complement thereof operably linked to suitable regulatory sequences.

In a fourth aspect, this invention concerns a transformed host cell comprising such a chimeric gene.

In a fifth aspect, this invention concerns a method of altering the level of fatty acids with conjugated double bonds which comprises:

(a) transforming a host cell with a chimeric gene as discussed above;

(b) growing the transformed host cell under conditions suitable for the expression of the chimeric gene; and (c) selecting those transformed host cells having altered levels of fatty acids with double bonds.

In a sixth aspect, this invention concerns a method for producing seed oil containing fatty acids with conjugated double bonds in the seeds of plants which comprises:
(a) transforming a plant cell with such a chimeric gene;
(b) growing a fertile mature plant from the transformed plant cell of step (a);
(c) screening progeny seeds from the fertile plants of step (b) for altered levels of fatty acids with conjugated double bonds; and
(d) processing the progeny seed of step (c) to obtain seed oil containing altered levels of plant fatty acids with conjugated double bonds.

In a seventh aspect, this invention concerns a method for producing plant fatty acid modifying enzymes associated with conjugated double bond formation which comprises:
(a) transforming a microbial host cell with the claimed chimeric genes;
(b) growing the transformed host cell under conditions suitable for the expression of the chimeric gene; and
(c) selecting those transformed host cells containing altered levels of protein encoded by the chimeric gene.

In an eighth aspect, this invention concerns an isolated nucleic acid fragment encoding a plant fatty acid modifying enzyme associated with conjugated double bond formation.

In a ninth aspect, this invention concerns a method to isolate nucleic acid fragments and functionally equivalent subfragments thereof encoding a plant fatty acid modifying enzyme associated with conjugated double bond formation comprising:
(a) comparing SEQ ID NOS:2, 4, 20, 24, or 30 and other plant fatty acid modifying enzyme polypeptide sequences;
(b) identifying conserved sequences of 4 or more amino acids obtained in step (a);
(c) designing degenerate oligomers based on the conserved sequences identified in step (b); and
(d) using the degenerate oligomers of step (s) to isolate sequences encoding a plant fatty acid modifying enzyme or a portion thereof associated with conjugated double bond formation by sequence dependent protocols.

In an tenth aspect, this invention concerns animal feed comprising an ingredient derived from the processing of any of the seeds obtained from plants transformed with the chimeric genes discussed herein as well as animal feed comprising at least one conjugated linolenic acid derived from oil extracted from a natural source selected from the group consisting of tung, bittermelon, pot marigold, jacaranda, catalpa, and pomegranate.

In an eleventh aspect, this invention concerns a method of improving the carcass quality of an animal by supplementing the diet of the animal with such animal feeds.

BRIEF DESCRIPTION OF THE FIGURES AND SEQUENCE DESCRIPTIONS

The invention can be more fully understood from the following detailed description and the Figure and Sequence Descriptions which form a part of this application.

The sequence descriptions summarize the Sequences Listing attached hereto. The Sequence Listing contains one letter codes for nucleotide sequence characters and the three letter codes for amino acids as defined in the IUPAC-IUB standards described in *Nucleic Acids Research* 13:3021–3030 (1985) and in the *Biochemical Journal* 219 (No. 2):345–373 (1984), and the symbols and format used for all nucleotide and amino acid sequence data further comply with the rules governing nucleotide and/or amino acid sequence disclosures in patent applications as set forth in 37 C.F.R. §1.821–1.825 and WIPO Standard St. 25.

FIG. 1 shows a comparison of the amino acid sequences of the instant fatty acid modifying enzymes associated with conjugated double bond formation from seeds of *Impatiens balsamina* (ImpH8Fad2, SEQ ID NO:2), *Momordica charantia* (MomFad2, SEQ ID NO:4), *Chrysobalanus icaco* (ChrFad2, SEQ ID NO:20), *Licania michauxi* (LinFad2, SEQ ID NO:24), and *Aleurites fordii* Class I (AleC1, SEQ ID NO:28), and *Aleurites fordii* Class II (AleC2, SEQ ID NO:30). The tung Class I gene is not believed to encode an enzyme associated with conjugated double bond formation. The amino acid sequences of these enzymes are compared with a soybean omega-6 oleate desaturase (Soy omega-6) and a castor bean fatty acid hydroxylase (Hydroxylase). The position of the glycine substitution for alanine, mentioned in Example 13, is highlighted with a *.

FIG. 2 shows the fatty acid profile of transgenic soybean embryos expressing the *Impatiens* fatty acid-modifying enzyme associated with conjugated double bond formation. Shown are gas chromatograms of fatty acid methyl esters prepared from wild-type soybean embryos (A), transgenic soybean embryos expressing the *Impatiens* polypeptide (B), and seeds of *Impatiens balsamina* (C). The wild-type fatty acids palmitic, stearic, oleic, linoleic, and linolenic: 16:0, 18:0, 18:1, 18:2, and 18:3, respectively, are labeled. The peaks corresponding to α-eleostearic acid and α-parinaric acid are also noted.

Figure 3:
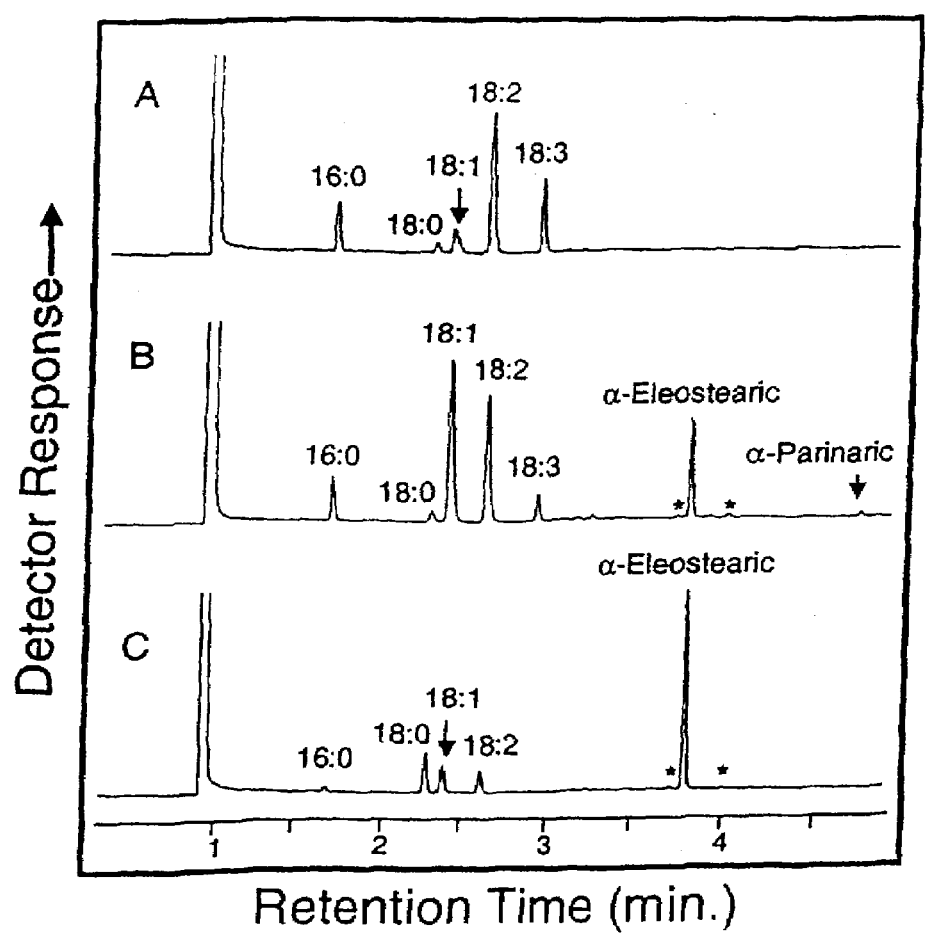

FIG. 3 shows the fatty acid profile of transgenic soybean embryos expressing the *Momordica* fatty acid-modifying enzyme associated with conjugated double bond formation. Shown are gas chromatograms of fatty acid methyl esters prepared from wild-type soybean embryos (A), transgenic soybean embryos expressing the *Momordica* polypeptide (B), and seeds of *Momordica charantia* (C). The asterisks (*) indicate cis-trans isomers of methyl α-eleostearic acid.

Figure 4:
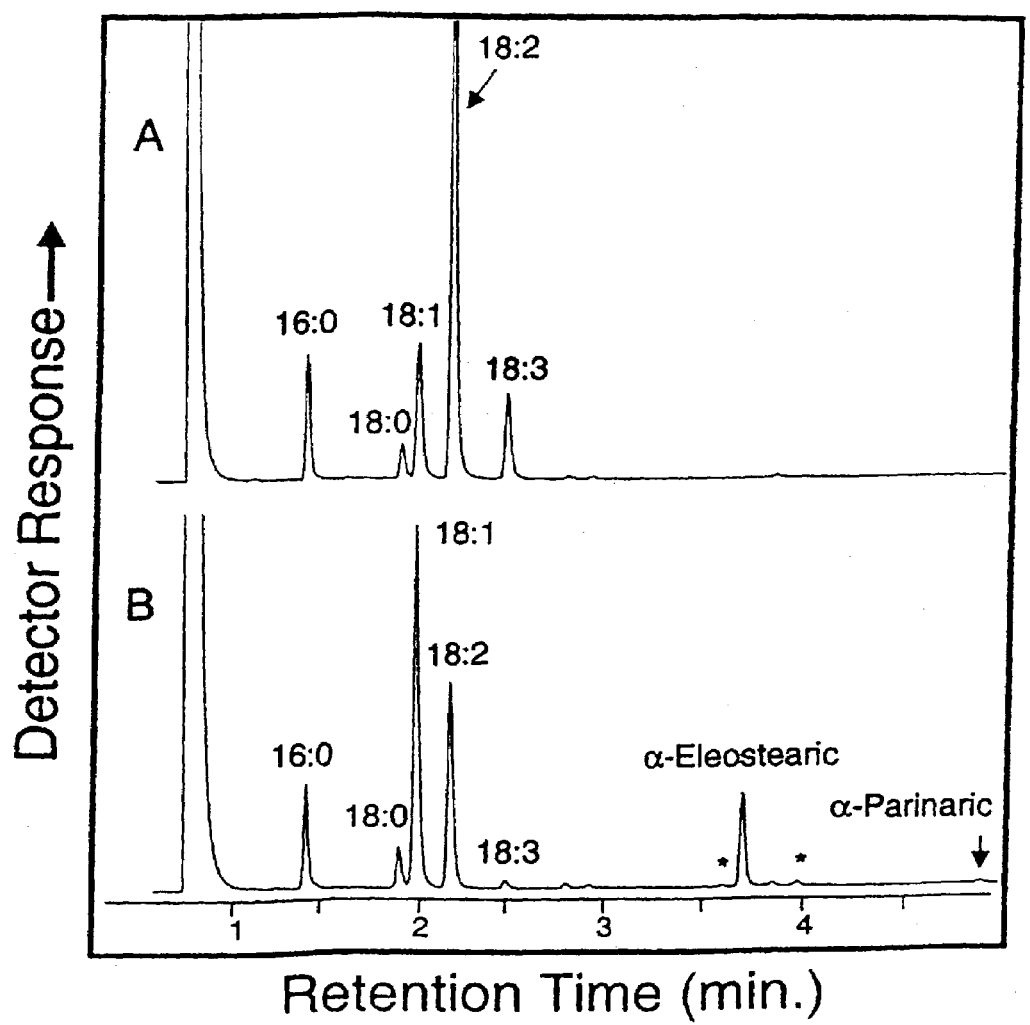

FIG. 4 shows the fatty acid profile of transgenic soybean seeds expressing the *Momordica* fatty acid-modifying enzyme associated with conjugated double bond formation. Shown are gas chromatograms of fatty acid methyl esters prepared from wild-type soybean seeds (A) and transgenic soybean seeds expressing the Momordica polypeptide (B). The asterisks (*) indicate cis-trans isomers of methyl α-eleostearic acid.

Figure 5:
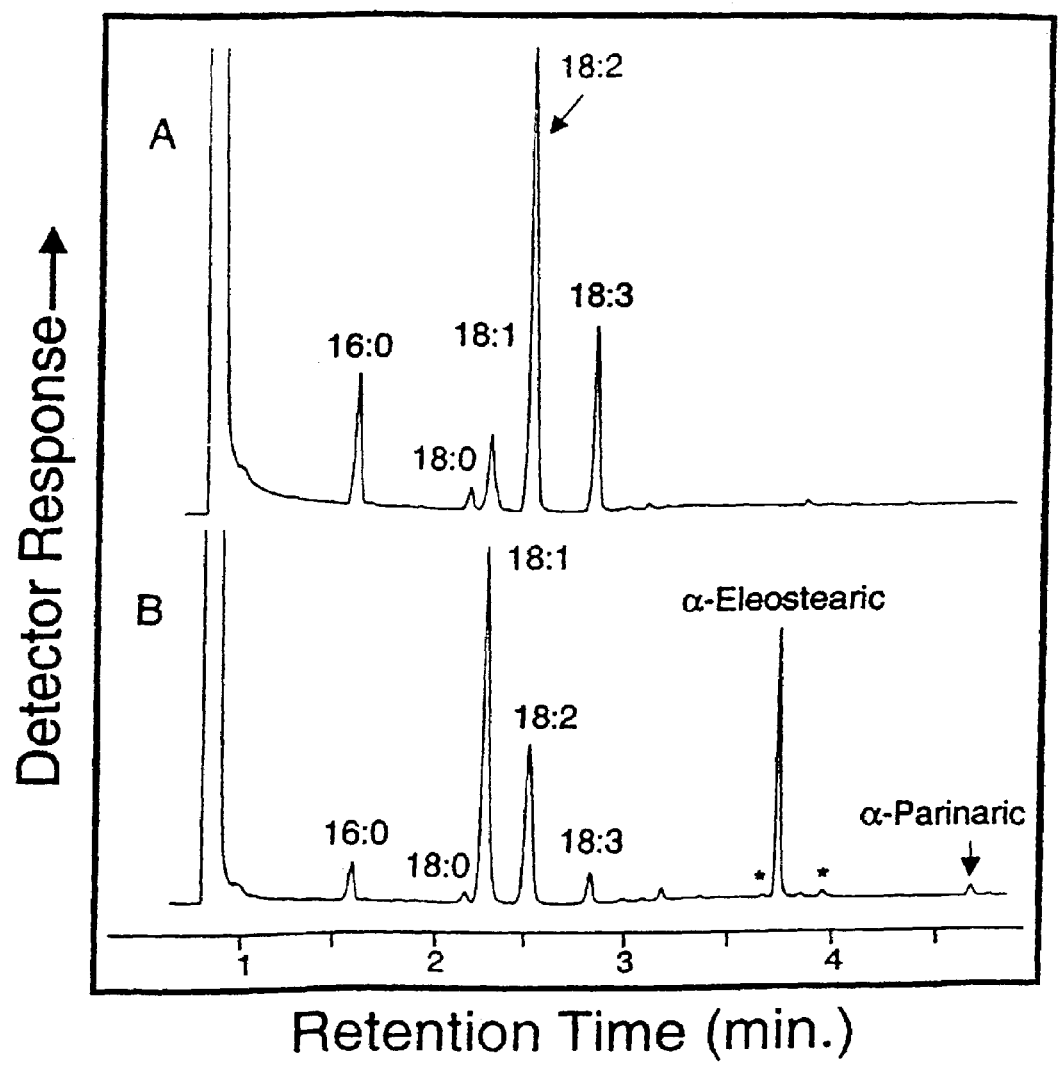

FIG. 5 shows the fatty acid profile of transgenic soybean embryos expressing the *Chrysobalanus icaco* fatty acid-modifying enzyme associated with conjugated double bond formation. Shown are gas chromatograms of fatty acid methyl esters prepared from wild-type soybean embryos (A) and transgenic soybean embryos expressing the *Chrysobalanus* polypeptide (B). The asterisks (*) indicate cis-trans isomers of methyl α-eleostearic acid.

SEQ ID NO:1 is the nucleotide sequence comprising the cDNA insert in clone ImpH8Fad2 encoding an fatty acid modifying enzymes associated with conjugated double bond formation from seeds of *Impatiens balsamina*.

SEQ ID NO:2 is the deduced amino acid sequence of the nucleotide sequence comprising the cDNA insert in clone ImpH8Fad2.

SEQ ID NO:3 is the nucleotide sequence comprising the cDNA insert in clone MomFad2 encoding fatty acid modifying enzymes associated with conjugated double bond formation from seeds of *Momordica charantia*.

SEQ ID NO:4 is the deduced amino acid sequence of the nucleotide sequence comprising the cDNA insert in clone MomFad2.

SEQ ID NO:5 is the amino acid sequence encoding the soybean (*Glycine max*) fatty acid desaturase enzyme depicted in FIG. 1.

SEQ ID NO:6 is the amino acid sequence encoding the castor bean (*Ricinus communis*) fatty acid hydroxylase enzyme depicted in FIG. 1.

SEQ ID NO:7 is the NcoI-containing 5'-end "sense" primer used to amplify the *Impatiens balsamina* coding region for cloning into the tobacco expression vector pML63.

SEQ ID NO:8 is the EcoRI-containing 3'-end "anti-sense" primer used to amplify the *Impatiens balsamina* coding region for cloning into the tobacco expression vector pML63.

SEQ ID NO:9 is the NcoI-containing 5'-end "sense" primer used to amplify the *Momordica charantia* coding region for cloning into the tobacco expression vector pML63.

SEQ ID NO:10 is the EcoRI-containing 3'-end "anti-sense" primer used to amplify the *Momordica charantia* coding region for cloning into the tobacco expression vector pML63.

SEQ ID NO:11 is the NotI-containing 5'-end "sense" primer used to amplify the *Impatiens balsamina* coding region for a fatty acid modifying enzyme associated with conjugated double bond formation from seeds, and its cloning into pKS67.

SEQ ID NO:12 is the NotI-containing 3'-end "anti-sense" primer used to amplify the *Impatiens balsamina* coding region for a fatty acid modifying enzyme associated with conjugated double bond formation from seeds, and its cloning into pKS67.

SEQ ID NO:13 is the NotI-containing 5'-end "sense" primer used to amplify the *Momordica charantia* coding region for a fatty acid modifying enzyme associated with conjugated double bond formation from seeds, and its cloning into pKS67.

SEQ ID NO:14 is the NotI-containing 5'-end "sense" primer used to amplify the *Momordica charantia* coding region for a fatty acid modifying enzyme associated with conjugated double bond formation from seeds, and its cloning into pKS67.

SEQ ID NO:15 is the BamHI-containing "antisense" primer used to amplify the 5'-end of the *Chrysobalanus icaco* cDNA encoding a fatty acid modifying enzyme associated with conjugated double bond formation from seeds.

SEQ ID NO:16 is the EcoRI-containing "sense" primer used to amplify the 3'-end of the *Chrysobalanus icaco* cDNA encoding a fatty acid modifying enzyme associated with conjugated double bond formation from seeds.

SEQ ID NO:17 is the BamHI-containing 5'-end "sense" primer used to amplify the coding region of the *Chrysobalanus icaco* cDNA encoding a fatty acid modifying enzyme associated with conjugated double bond formation from seeds.

SEQ ID NO:18 is the EcoRI-containing 3'-end "anti-sense" primer used to amplify the coding region of the *Chrysobalanus icaco* cDNA encoding a fatty acid modifying enzyme associated with conjugated double bond formation from seeds.

SEQ ID NO:19 is the nucleotide sequence comprising the cDNA insert in a cDNA clone encoding a fatty acid modifying enzymes associated with conjugated double bond formation from seeds of *Chrysobalanus icaco*.

SEQ ID NO:20 is the deduced amino acid sequence of the nucleotide sequence comprising the cDNA insert in the clone from SEQ ID NO:19.

SEQ ID NO:21 is the NotI-containing 5'-end "sense" primer used to amplify the coding region of the *Chrysobalanus icaco* cDNA encoding a fatty acid modifying enzyme associated with conjugated double bond formation from seeds.

SEQ ID NO:22 is the NotI-containing 3'-end "antisense" primer used to amplify the coding region of the *Chrysobalanus icaco* cDNA encoding a fatty acid modifying enzyme associated with conjugated double bond formation from seeds.

SEQ ID NO:23 is the nucleotide sequence comprising the cDNA insert in a cDNA clone encoding a fatty acid modifying enzymes associated with conjugated double bond formation from seeds of *Licania michauxi*.

SEQ ID NO:24 is the deduced amino acid sequence of the nucleotide sequence comprising the cDNA insert in the clone from SEQ ID NO:23.

SEQ ID NO:25 is the EcoRI-containing 5'-end "sense" primer used to amplify the coding region of the *Aleurites fordii* cDNA encoding a fatty acid modifying enzyme associated with conjugated double bond formation from genomic DNA.

SEQ ID NO:26 is the EcoRI-containing 3'-end "antisense" primer used to amplify the coding region of the *Aleurites fordii* cDNA encoding a fatty acid modifying enzyme associated with conjugated double bond formation from genomic DNA.

SEQ ID NO:27 is the nucleotide sequence comprising the cDNA insert in a cDNA clone encoding a Class I fatty acid modifying enzymes associated with conjugated double bond formation from PCR amplified genomic DNA of *Aleurites fordii*.

SEQ ID NO:28 is the deduced amino acid sequence of the nucleotide sequence comprising the cDNA insert in the clone from SEQ ID NO:27.

SEQ ID NO:29 is the nucleotide sequence comprising the cDNA insert in a cDNA clone encoding a Class II fatty acid modifying enzymes associated with conjugated double bond formation from PCR amplified genomic DNA of *Aleurites fordii*.

SEQ ID NO:30 is the deduced amino acid sequence of the nucleotide sequence comprising the cDNA insert in the clone from SEQ ID NO:29.

SEQ ID NO:31 is the XbaI-containing 5'-end "sense" primer used to amplify the coding region between the conserved amino acid repeats KKAIPPHCF and WREAKEC of the *Chrysobalanus icaco* cDNA encoding a fatty acid modifying enzyme associated with conjugated double bond formation from genomic DNA.

SEQ ID NO:32 is the BglII-containing 3'-end "antisense" primer used to amplify the coding region between the conserved amino acid repeats KKAIPPHCF and WREAKEC of the *Chrysobalanus icaco* cDNA encoding a fatty acid modifying enzyme associated with conjugated double bond formation from genomic DNA.

SEQ ID NO:33 is the NcoI-containing 5'-end "sense" primer used to amplify the coding region of the *Licania michauxi* cDNA encoding a fatty acid modifying enzyme associated with conjugated double bond formation from genomic DNA.

SEQ ID NO:34 is the BglII-containing 3'-end "antisense" primer used to amplify the coding region of the *Licania*

*michauxi* cDNA encoding a fatty acid modifying enzyme associated with conjugated double bond formation from genomic DNA.

DETAILED DESCRIPTION OF THE INVENTION

In the context of this disclosure, a number of terms shall be utilized.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides are referred to by their single letter designation as follows: "A" for adenosine, "C" for cytidine, "G" for guanosine, "T" for thymidine, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Preferred substantially similar nucleic acid sequences encompassed by this invention are those sequences that are 45% identical to the nucleic acid fragments reported herein or which are 45% identical to any portion of the nucleotide sequences reported herein. More preferred are nucleic acid fragments which are 50% identical to the nucleic acid sequences reported herein, or which are 50% identical to any portion of the nucleotide sequences reported herein. Most preferred are nucleic acid fragments which are 60% identical to the nucleic acid sequences reported herein, or which are 60% identical to any portion of the nucleotide sequences reported herein. Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151–153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402); see also www.ncbi.nlm.nih.gov/BLAST/).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the klenow fragment of DNA polymerase I. "Sense" RNA refers to RNA transcript that includes the mRNA and so can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed.

"Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence that is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature (London)* 327:70–73; U.S. Pat. No. 4,945,050), or an Agrobacterium-mediated method using an appropriate Ti plasmid containing the transgene (Ishida Y. et al., 1996, Nature Biotech. 14:745–750).

Standard recombinant DNA and molecular cloning techniques used herein are well known in the art and are described more fully in Sambrook, J., Fritsch, E. F. and Maniatis, T. *Molecular Cloning: A Laboratory Manual*;

Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

An "expression construct" as used herein comprises any of the isolated nucleic acid fragments of the invention used either alone or in combination with each other as discussed herein and further may be used in conjunction with a vector or a subfragment thereof. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411–2418; De Almeida et al., (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. The terms "expression construct" and "recombinant expression construct" are used interchangeably herein.

The term "$\omega^6$-oleic acid desaturase" refers to a cytosolic enzyme that catalyzes the insertion of a double bond into oleic acid between the twelfth and thirteenth carbon atoms relative to the carboxyl end of the acyl chain. Double bonds are referred to as "cis" or "trans" because they are chiral units that can assume the following non-equivalent structures:

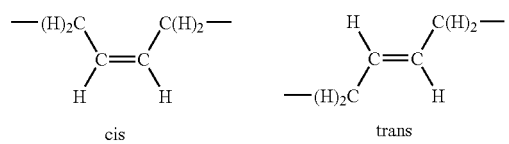

cis                    trans

The oleic acid substrate for this enzyme may be bound to a glycerolipid such as phosphatidylcholine. The term "$\omega^6$-oleic acid desaturase" is used interchangeably with the terms "$\omega^6$-desaturase", "$\Delta^2$-oleic acid desaturase", "$\Delta^{12}$-desaturase", and "Fad2". The $\omega^6$ and $\Delta^2$ positions are equivalent in oleic acid (C18) because $\omega$-carbons are counted from the methyl-end, while $\Delta$-carbons are counted from the carboxyl-end of the fatty acid chain. The enzymes of the present invention comprise activities involving desaturation of fatty acids resulting in conjugated double bond formation. The term "conjugated double bond" is defined as two double bonds in the relative positions indicated by the formula —CH=CH—CH=CH— (Grant & Hackh's Chemical Dictionary, Fifth Ed., R. Grant and C. Grant eds., McGraw-Hill, New York). The $\pi$-orbital electrons are shared between conjugated double bonds, but remain relatively independent in unconjugated double bonds. This explains the greater reactivity of conjugated double bonds to oxidation. The modifying enzymes, associated with conjugated double bond formation described herein, are also referred to as "$\omega^6$-oleic acid desaturase-related", "$\Delta^{12}$-oleic acid desaturase-related", "$\omega^6$-oleic acid desaturase-like", or "$\Delta^{12}$-oleic acid desaturase-like. The terms "-related" and "-like" reflect the conservation and differences in nucleic acid sequence homology between the genes encoding Fad2 enzymes versus the genes of the present invention.

This invention concerns an isolated nucleic acid fragment encoding a plant fatty acid modifying enzyme associated with conjugated double bond formation wherein said fragment or a functionally equivalent subfragment thereof (a) hybridizes to any of the nucleotide sequences set forth in SEQ ID NOS:1, 3, 19, 23, or 29 under conditions of moderate stringency or (b) is at least 45% identical to a polypeptide encoded by any of the nucleotide sequences set forth in SEQ ID NOS:1, 3, 19, 23, or 29 or a functionally equivalent subfragment thereof as determined by a comparison method designed to detect homologous sequences.

Such enzymes are normally expressed in developing seeds of Impatiens balsamina, Momordica charantia and Chrysobalanus icaco that are similar in sequence to plant, membrane-bound fatty acid desaturases. However, these fatty acid modifying enzymes differ from membrane-bound fatty acid desaturases in their functionality. Specifically, these enzymes are associated with the formation of fatty acids having conjugated double bonds and, more particularly, with the formation of conjugated linolenic acids. Examples of fatty acids having conjugated double bonds include, but are not limited to, eleostearic acid and/or parinaric acid. Naturally occuring plant oils containing eleostearic acid include tung oil from Aleurites fordii or montana, which contains up to 69% $\alpha$-eleostearic acid in the oil extracted from the seeds, or oils from valarian species (Centranthus microsiphon). There can also be mentioned jacaric acid (from the jacaranda tree, Jacaranda mimosifolia and Jacaranda chelonia, $18:3\Delta^{8cis,10trans,12cis}$), calendic acid (from marigold or African daisy, Calendula officinalis, and Osteospermum spinescens and Osteospermum hyoseroides, $18:3\Delta^{8trans,10trans,12cis}$), catalpic acid (from the trumpet creeper, Catalpa ovata, or speciosa, or bigninioides, $18:3\Delta^{9trans,11trans,13cis}$), and punicic acid (from bitter melon and pomegranate, or Tricosanthes species, Cucurbita, and Punica granatum, Tricosanthes cucumeroides, $18:3\Delta^{9cis,11trans,13cis}$). These and other examples of fatty acids having conjugated double bonds may be found in "The Lipid Handbook" (Second Edition, Gunstone, F. D., et al., eds., Chapman and Hall, London, 1994), Crombie and Holloway (J. Chem. Soc. Perkins Trans. 1985:2425–2434), and Liu, et al. (Plant. Physiol. [1997] 113:1343–1349). These conjugated fatty acids are also referred to as ClnAs (conjugated linolenic acids) because they are all 18:3 in composition. This is in contrast to CLAs (conjugated linoleic acids) which have an 18:2 configuration.

The nomenclature "18:3" denotes the number of carbons in the fatty acid chain (in this case "18" or stearic acid length), and the number of unsaturating double bonds (in this case "3" specifying this fatty acid as linolenic). Although 18:2 and 18:3 denote linoleic acid and linolenic acid, respectively, the positions of the double bonds are not specified (i.e., they may be unconjugated or conjugated, cis or trans).

The term "eleostearic acid" as used herein refers to a mixture of cis-trans isomers of $\Delta^{9,11,13}$-octadecatrienoic acid ($18:3\Delta^{9,11,13}$). This mixture comprises principally $\alpha$-eleostearic acid ($18:3\Delta^{9cis,11trans,13trans}$) but may contain other isomers including β-eleostearic acid ($18:3\Delta^{9trans,11trans,13trans}$). The term "parinaric acid" as used herein refers to a mixture of cis-trans isomers of $\Delta^{9,11,13,15}$-octadecatetraenoic acid ($18:4\Delta^{9,11,13,15}$). This mixture comprises principally α-parinaric acid ($18:3\Delta^{9cis,11trans,13trans,15cis}$) but may contain other isomers including β-parinaric acid ($18:3\Delta^{9trans,11trans,13trans,15trans}$). As those skilled in the will appreciate, eleostearic acid and parinaric acids are separated easily by gas chromatography-mass spectrometry (GC-MS, see FIG. 3) and the alpha forms can be distinguished from the beta forms (marked by * in FIG. 3). More details on GC-MS analyses are found in Examples 4, 5, 7, and 8.

Examples of comparison methods which detect sequence homology include but are not limited to the BLAST computational method (Basic Local Alignment Search Tool; Altschul et al. (1993) *J. Mol. Biol.* 215:403–410; see also www.ncbi.nlm.nih.gov/BLAST/) which includes BLASTN (nucleotide, both strands), BLASTX (nucleotide, six-frame translation), BLASTP (protein), TBLASTN (protein, from six-frame translation), TBLASTX (nucleotide, six-frame translation), (for more information on BLAST, see "help" or "blast manuals" located at blast@ncbi.nlm.nih.gov/BLAST/), Megalign program of the LASARGENE bioinformatics computing suite (DNASTAR Inc., Madison, Wis., used for calculating percent identity), and the Clustal method of multiple sequence alignment (Higgins and Sharp (1989) *CABIOS.* 5:151–153). The default parameters were used for all comparisons and for all methods. The BLAST suite at NCBI has a detailed discussion of their algorithms at their web site, the Megalign program uses a Clustal program that shares default parameters with Clustal, namely, for multiple sequence alignments of nucleic acids or polypeptides (GAP PENALTY=10, GAP LENGTH PENALTY=10), for pairwise alignments of nucleic acids (KTUPLE=2, GAP PENALTY=5, WINDOW=4, DIAGONALS SAVED=4), and for pairwise alignments of polypeptides (KTUPLE=1, GAP PENALTY=3, WINDOW=5, DIAGONALS SAVED=5).

Surprisingly and unexpectedly, it has been found that the fatty acid modifying enzymes associated with conjugated double bond formation do not appear to have strict substrate specificity. For example, the enzymes obtained from either *Impatiens, Momordica, Chrysolbalanus, Licania,* or *Aleurites* are believed to be capable of converting linoleic acid ($18:2\Delta^{9,12}$) to eleostearic acid ($18:3\Delta^{9,11,13}$) and linolenic acid ($18:3\Delta^{9,12,15}$) to parinaric acid ($18:4\Delta^{9,11,13,15}$) based on the availability of these two substrates in the background of choice. Thus, it appears that different ratios of eleostearic and parinaric acids can be produced in transgenic seed oils by choosing backgrounds with differing contents of linoleic and linolenic acids.

Accordingly, the present invention concerns an isolated nucleic acid fragment encoding a plant fatty acid modifying enzyme associated with conjugated double bond formation.

This invention also relates to an isolated nucleic acid fragment encoding a plant fatty acid modifying enzyme associated with conjugated double bond formation wherein said fragment or a functionally equivalent subfragment thereof encodes a protein comprising any one of the amino acid sequences set forth in SEQ ID NOS:2, 4, 20, 24, or 30.

In another aspect, this invention concerns an isolated nucleic acid fragment encoding a plant fatty acid modifying enzyme associated with conjugated double bond formation wherein said fragment or a functionally equivalent subfragment thereof hybridizes to any of the isolated nucleic acid fragments or functionally equivalent subfragments thereof encoding a plant fatty acid modifying enzyme associated with conjugated double bond formation wherein said fragment or subfragment encodes a protein comprising any one of the amino acid sequences set forth in SEQ ID NOS:2, 4, 20, 24, or 30 and further wherein said fragment or subfragment (a) hybridizes to this isolated nucleic acid fragment or functionally equivalent subfragment under conditions of moderate stringency or (b) is at least 45% identical to a polypeptide encoded by any of the foregoing isolated nucleic acid fragments or a functionally equivalent subfragment thereof as determined by a comparison method designed to detect homologous sequences. Examples of suitable comparison methods which detect homologous sequences are discussed above.

Also of interest is a chimeric gene comprising any of the instant isolated nucleic acid fragments or functionally equivalent subfragments thereof or a complement thereof operably linked to suitable regulatory sequences wherein expression of the chimeric gene results in production of altered levels of the desired enzyme in a transformed host cell.

The invention also relates to methods of using such isolated nucleic acid fragments or functionally equivalent subfragments thereof or the complement thereof to alter the level of fatty acids with conjugated double bond formation in a host cell which comprises:

(a) transforming a host cell with any of the instant chimeric genes;

(b) growing the transformed host cell under conditions suitable for the expression of the chimeric gene; and (c) selecting those transformed host cells having altered levels of fatty acids with conjugated double bonds.

In still another aspect, this invention concerns a method for producing seed oil containing fatty acids with conjugated double bonds in the seeds of plants which comprises:

(a) transforming a plant cell with any of the instant chimeric genes;

(b) growing a fertile mature plant from the transformed plant cell of step (a);

(c) screening progeny seeds from the fertile plants of step (b) for altered levels of fatty acids with conjugated double bonds; and (d) processing the progeny seed of step (c) to obtain seed oil containing altered levels plant fatty acids with conjugated double bonds.

In still a further aspect, this invention concerns a method for producing plant fatty acid modifying enzymes associated with conjugated double bond formation which comprises:

(a) transforming a microbial host cell with any of the instant chimeric genes;

(b) growing the transformed host cell under conditions suitable for the expression of the chimeric gene; and (c) selecting those transformed host cells containing altered levels of protein encoded by the chimeric gene.

The isolated nucleic acid fragments encoding fatty acid modifying enzymes associated with conjugated double bond formation in seeds of *Impatiens balsamina, Momordica charantia, Chrysobalanus icaco, Licania michauxii,* and *Aleurites fordii* is provided in SEQ ID NO:1, 3,19, 23, and 29 respectively, and the corresponding deduced amino acid sequences are provided in SEQ ID NO:2, 4, 20, 24, and 30. Fatty acid modifying enzymes associated with conjugated double bond formation from other plants can now be identified by when nucleotide sequence hybridizes to any of the nucleotide sequences set forth in SEQ ID NOS:1, 3, 19, 23, and 29 under conditions of moderate stringency, as set forth above or (b) is at least 45% identical to a polypeptide encoded by any of the nucleotide sequences set forth in SEQ ID NOS:1, 3, 19, 23, and 29 or a functionally equivalent subfragment thereof as determined by a comparison method designed to detect homologous sequences.

The amino acid sequences encoded by these nucleotide sequences disclosed herein are compared in FIG. 1 to the fatty acid desaturase from soybean which inserts the second double bond between carbon atoms 12 and 13 into monounsaturated fatty acid, oleic acid to produce linoleic acid.

The isolated nucleic acid fragments of the instant invention or functionally equivalent subfragments thereof or the complement thereof can be used to create chimeric genes to transform host cells. Examples of host cells which can be transformed include prokaryotic and eukaryotic cells. There can be mentioned microorganisms such as the bacterium *E. coli* and yeast *Saccharomyces cerevisiae*. Examples of plant cells include but are not limited to those obtained from soybean, oilseed Brassica species, corn, peanut, rice, wheat, sunflower, safflower, cotton, and cocoa.

Thus, the chimeric genes of the instant invention can be used to create transgenic plants in which the fatty acid modifying enzymes associated with conjugated double bond formation in seeds of *Impatiens balsamina, Momordica charantia, Chrysobalanus icaco, Licania michauxii*, and *Aleurites fordii* are present at higher levels than normal or in cell types or developmental stages in which it is not normally found. Also of interest, are seeds obtained from such plants and oil obtained from these seeds.

Transgenic plants can be made in which fatty acid modifying enzyme associated with conjugated double bond formation is present at higher or lower levels than normal or in cell types or developmental stages in which it is not normally found. This would have the effect of altering the level of such fatty acids with conjugated double bonds in those cells. It may be desirable to reduce or eliminate expression of a gene encoding such enzymes in plants for some applications. In order to accomplish this, a chimeric gene designed for co-suppression of the endogenous enzyme can be constructed by linking a gene or gene fragment encoding a fatty acid modifying enzyme associated with conjugated double bond formation to plant promoter sequences. Alternatively, a chimeric gene designed to express antisense RNA for all or part of the instant nucleic acid fragment can be constructed by linking the isolated nucleic acid fragment or a functionally equivalent subfragment thereof in reverse orientation to plant promoter sequences. Either the co-suppression or antisense chimeric genes could be introduced into plants via transformation wherein expression of the corresponding endogenous genes are reduced or eliminated.

When over-expressed in plant cells, the fatty acid modifying enzymes associated with conjugated double bond formation in seeds of *Impatiens balsamina, Momordica charantia*, and *Chrysobalanus icaco* can be useful for causing the biosynthesis and accumulation of fatty acids with conjugated double bonds, such as eleostearic acid and/or parinaric acid, in those cells. It is particularly useful to use fatty acid modifying enzymes associated with conjugated double bond formation in seeds of *Impatiens balsamina, Momordica charantia*, and *Chrysobalanus icaco* to produce fatty acids containing conjugated double bonds in the cells of the seeds of oilseed crop plants.

Overexpression of fatty acid modifying enzymes associated with conjugated double bond formation in seeds of *Impatiens balsamina, Momordica charantia*, and *Chrysobalanus icaco* may be accomplished by first constructing a chimeric gene in which the coding region of cDNAs for fatty acid modifying enzymes associated with conjugated double bond formation in seeds of *Impatiens balsamina, Momordica charantia*, and *Chrysobalanus icaco* is operably linked to a promoter capable of directing expression of a gene in the desired tissues at the desired stage of development. For reasons of convenience, the chimeric gene may comprise a promoter sequence and translation leader sequence derived from the same gene. 3' non-coding sequences encoding transcription termination signals must also be provided. The instant chimeric genes may also comprise one or more introns in order to facilitate gene expression.

Vectors such as plasmid vectors comprising the instant chimeric genes can then constructed. The choice of vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant fatty acid modifying enzymes associated with conjugated double bond formation in seeds of *Impatiens balsamina, Momordica charantia*, and *Chrysobalanus icaco* to different cellular compartments, or to facilitate its secretion from the cell. It is thus envisioned that the chimeric genes described above may be further supplemented by altering the coding sequences to encode fatty acid modifying enzymes associated with conjugated double bond formation in seeds of *Impatiens balsamina, Momordica charantia*, and *Chrysobalanus icaco* disclosed herein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

The nucleic acid fragments of the instant invention or functionally equivalent subfragment thereof may be used to isolate cDNAs and other nucleic acid fragments encoding homologous fatty acid modifying enzymes from the same or other plant species. Isolation of homologous nucleotide sequences using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction). The term "conserved sequence(s)" as used herein encompasses both strict conservation as well as conservation of a majority of the sequences used in an alignment, for example, conservation with respect to a consensus sequence.

Thus, in still a further aspect this invention concerns a method to isolate nucleic acid fragments and functionally equivalent subfragments thereof encoding a plant fatty acid modifying enzyme associated with conjugated double bond formation comprising:

(a) comparing SEQ ID NOS:2, 4, 20, 24, or 30 and other plant fatty acid modifying enzyme polypeptide sequences;
(b) identifying conserved sequences of 4 or more amino acids obtained in step (a);
(c) designing degenerate oligomers based on the conserved sequences identified in step (b); and
(d) using the degenerate oligomers of step (s) to isolate sequences encoding a plant fatty acid modifying enzyme or a portion thereof associated with conjugated double bond formation by sequence dependent protocols.

For example, nucleic acid fragments encoding homologous fatty acid modifying enzymes, either as cDNAs or genomic DNAs, could be isolated directly by using all or a portion of the instant nucleic acid fragments or functionally equivalent subfragments thereof as DNA hybridization probes to screen libraries from any desired plant employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Thus, other nucleic acid fragments encoding enzymes associated with conjugated double bond formation can be identified using any of the general methodologies described above. For example, a general group of fatty acid desaturase (FAD) related cDNAs, can be identified and a specific subset of those cDNAs encoding enzymes involved in conjugated double bond formation can be detected or screened by transformation. A group of cDNA sequences encoding fatty acid desaturase-like enzymes can be identified using low-stringency hybridization (for example 2×SSC, 0.1% SDS, 60° C.) with a probe corresponding to any known FAD sequence, and/or all- or -part of the sequences presented in any of SEQ ID NOS:1, 3, 19, 23, 27, or 29. Alternatively, randomly sequenced cDNAs can be analyzed by a computer program designed to detect homologous sequences, such as, but not limited to, BLAST or gappedBLAST (using standard default parameters). BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). Test sequences are analyzed for similarity to all publicly available DNA sequences contained in the "nr" database using the BLASTN algorithm provided by the National Center for Biotechnology Information (NCBI). The DNA sequences are translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability), or "pLog" (the negative of the logarithm of the P-value), is given as a measure of similarity between the two sequences. A test sequence and a sequence contained in the searched databases are compared, and the probability that the two sequences are related only by chance is calculated by BLAST and reported as a "pLog" value. Accordingly, the greater the pLog value, the greater the likelihood that the cDNA sequence and the BLAST "hit" represent homologous proteins. Sequences with pLogs greater than 5, or preferrably greater than 10, or more preferrably greater than 15, and most preferrably greater than 20, that are defined as FADs or lipid desaturases are candidates. cDNAs encoding enzymes associated with conjugated double bond formation can be identified from the candidate pools using transformation screening. Individual cDNAs are inserted into expression vectors and transformed into yeast or plant host cells using methods well known to those skilled in the art (see Examples 3, 4, 5, 7, 9, and 10). Production of fatty acids containing conjugated double bonds is confirmed by GC-MS analyses as described in the Examples 4, 5, 7, and 8. Yeast or plant tissue culture cells are preferred for initial screening due to speed and the ease with which they can be handled when dealing with large numbers of transformants and the appropriate cell biology and eucaryotic cell physiology.

The instant fatty acid modifying enzymes associated with conjugated double bond formation in seeds of *Impatiens balsamina*, *Momordica charantia*, and *Chrysobalanus icaco* produced in heterologous host cells, particularly in the cells of microbial hosts, can be used to prepare antibodies to the fatty acid modifying enzymes associated with conjugated double bond formation in seeds of *Impatiens balsamina*, *Momordica charantia*, and *Chrysobalanus icaco* by methods well known to those skilled in the art. The antibodies are useful for detecting the instant fatty acid modifying enzymes associated with conjugated double bond formation in seeds of *Impatiens balsamina*, *Momordica charantia*, and *Chrysobalanus icaco* in situ in cells or in vitro in cell extracts. Preferred heterologous host cells for production of the instant fatty acid modifying enzymes associated with conjugated double bond formation in seeds of *Impatiens bal-* samina, *Momordica charantia*, and *Chrysobalanus icaco* are microbial hosts. Microbial expression systems and expression vectors containing regulatory sequences that direct high level expression of foreign proteins are well known to those skilled in the art. Any of these could be used to construct chimeric genes for production of the instant fatty acid modifying enzymes associated with conjugated double bond formation in seeds of *Impatiens balsamina, Momordica charantia*, and *Chrysobalanus icaco*. These chimeric genes could then be introduced into appropriate microorganisms via transformation to provide high level expression of the encoded fatty acid modifying enzymes associated with conjugated double bond synthesis in seeds of *Impatiens balsamina, Momordica charantia*, and *Chrysobalanus icaco*. An example of the use of the *Impatiens balsamina* fatty acid modifying enzyme in *Saccharomyces cerevisiae* for the production of parinaric acid from linolenic acid is discussed below in Example 5. An example of a vector for high level expression of the instant fatty acid modifying enzymes associated with conjugated double bond formation in seeds of *Impatiens balsamina, Momordica charantia*, and *Chrysobalanus icaco* in a bacterial host is discussed below in Example 9.

In still another aspect, it has been found that conjugated fatty acids, more specifically, conjugated linolenic acids can also be used as an animal feed additive. The quality of meat grown for consumption is dependent upon many variables that ultimately influence market demand for the product. For instance, pork quality improvement is a primary focus of the pork industry. Quality variables include pork color, water holding capacity, size, chemical composition and firmness of lean and fat tissue. Experiments have shown that the fat firmness of pork can be influenced by the addition of conjugated linoleic acid ($18:2\Delta^{9cis, 11trans}$ or $\Delta^{10trans, 12cis}$) to swine diets (Eggert, J. M., et al. (1999) *J. Anim. Sci.* 77(*Suppl*):53; Thiel, R. C., et al. (1998) *J. Anim. Sci.* 76(*Suppl*):13; Wiegand, B. R., F. C. Parrrish Jr. and J. C. Sparks (1999) *J. Anim. Sci.* 77(*Suppl*): 19; U.S. Pat. No. 5,554,646; and U.S. Pat. No. 5,851,572). Some experiments have also reported improved carcass leanness and the efficiency of feed utilization when conjugated linoleic acid (CLA) is added as a supplement to the diet. It is not known whether feeding of different conjugated fatty acids would have similar effects. The present invention describes the production of conjugated double bonds in 18:3 and 18:4 fatty acids which are derived from 18:3 fatty acids in transgenic seeds that can be used as feed additives.

Thus, the instant invention concerns animal feed comprising an ingredient derived from the processing of any of the seeds obtained plants or plant cells transformed with any of the chimeric genes discussed herein or the animal feed can comprise at least one conjugated linolenic acid derived from oil extracted from a natural source selected from the group consisting of tung, bittermelon, pot marigold, jacaranda, catalpa, and pomegranate. The ingredient or conjugated linolenic acid should be present in a carcass quality improving amount. A "carcass quality improving amount" is that amount needed to improve the carcass quality of an animal. The ingredient can be a mixture of fatty acids obtained from such seeds. This mixture can be in any form suitable for use as a feed additive. For example, the mixture can be in the form of an oil whether or not it is saponified.

Also of interest is animal feed comprising oil obtained from any of the foregoing seeds. This invention also includes a method of improving the carcass quality of an animal by supplementing a diet of the animal with any of the animal feeds discussed above.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from developing seeds of *Impatiens balsamina, Momordica charantia, Chrysobalanus icaco* and *Licania michauxii* were prepared. The seeds chosen were actively accumulating fatty acids with conjugated double bonds. The libraries were prepared using a Uni-ZAP™ XR kit according to the manufacturer's protocol (Stratagene Cloning Systems,La Jolla, Calif.), except that cDNAs were cloned into the EcoRI and XhoI sites of the bacterial vector pBluescript SK(−) rather than into a phage vector. Libraries were maintained in *E. coli* DH10B cells (Life Technologies, Gaithersburg, Md.). cDNA inserts from randomly picked bacterial colonies containing recombinant pBluescript plasmids were grown up and plasmid purified. cDNAs were sequenced using primers specific for vector sequences flanking the inserted cDNA sequences. Insert DNAs were sequenced in dye-primer sequencing reactions to generate partial cDNA sequences (expressed sequence tags or "ESTs"; see Adams, M. D. et al., (1991) *Science* 252:1651) using a Perkin Elmer Model 377 fluorescent sequencer. The resulting ESTs were analyzed using computational methods as described below.

Example 2

Identification and Characterization of cDNA Clones

ESTs encoding *Impatiens balsamina* and *Momordica charantia* fatty acid modifying enzymes were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank coding sequence ["CDS"] translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using sequence information derived from *Impatiens balsamina* clone ids.pk001.h8 revealed strong similarity of the proteins encoded by cDNAs for a cotton omega-6 fatty acid desaturase (EMBL Accession No. Y10112; pLog=49.25) and for a tomato "lipid desaturase-like protein" (EMBL Accession No. X94944; pLog=48.68). The sequence of the entire cDNA insert in clone ids.pk001.h8 was determined and reevaluated by BLASTP, yielding even higher pLog values when compared to the sequences of potato fatty acid desaturase enzyme (X92847; pLog=152.0) and pLogs of 150.00 when compared to the omega-6 fatty acid desaturases of both *Arabidopsis* (Swiss Prot Accession No. P46313) and cotton (EMBL Accession No. Y10112). SEQ ID NO:1 shows the nucleotide sequence of the entire *Impatiens balsamina* cDNA in clone ids.pk001.h8; the deduced amino acid sequence is shown in SEQ ID NO:2. Sequence alignments and BLAST scores and probabilities indicate that the instant nucleic acid fragment encodes an *Impatiens balsamina* protein that is structurally related to the omega-6 class of fatty acid desaturases. The clone for this protein was designated ImpH8Fad2.

A similar BLASTX search using sequence information derived from *Momordica charantia* clone fds.pk0009.h10 revealed similarity of the proteins encoded by cDNAs omega-6 fatty acid desaturases from soybean (Accession No. L43920; pLog=13.92) and from *Arabidopsis* (EMBL Accession No. L26296; pLog=9.96). The sequence of the entire cDNA insert in clone fds.pk0009.h10 was determined and reevaluated by BLASTP 2.0.4, yielding even higher pLog values when compared to the sequences of potato fatty acid desaturase enzyme (X92847; pLog=152.0) and pLogs of 151.00 and 147.00 when compared to the omega-6 fatty acid desaturases of peanut (Accession No. AF030319) and cotton (EMBL Accession No. Y10112), respectively. SEQ ID NO:3 shows the nucleotide sequence of the entire *Momordica charantia* cDNA in clone fds.pk0009.h10; the deduced amino acid sequence is shown in SEQ ID NO:4. Sequence alignments and the BLAST scores and probabilities indicate that the instant nucleic acid fragment encodes a *Momordica charantia* protein that is structurally related to the omega-6 class of fatty acid desaturases. The clone for this protein was designated MomFad2.

Example 3

Expression of Chimeric Genes in Tobacco Cells

The cDNAs encoding fatty acid modifying enzymes associated with conjugated double bond synthesis in seeds of *Impatiens balsamina* and *Momordica charantia* were introduced into a plant expression vector designated pML63. Vector pML63 contains the uidA gene (which encodes the GUS enzyme) operably linked to the CaMV35S promoter and 3' NOS sequence. pML63 is modified from pMH40 to produce a minimal 3' NOS terminator fragment. pMH 40 is described in WO 98/16650 which was published on Apr. 23, 1998, the disclosure of which are hereby incorporated by reference. Using standard techniques familiar to those skilled in the art, the 770 base pair terminator sequence contained in pMH40 was replaced with a new 3' NOS terminator sequence comprising nucleotides 1277 to 1556 of the sequence published by Depicker et al. (1982, J. Appl. Genet. 1:561–574). A chimeric gene was constructed comprising cDNAs encoding fatty acid modifying enzymes associated with conjugated double bond synthesis in seeds of *Impatiens balsamina* and *Momordica charantia* in sense orientation with respect to the cauliflower mosaic virus 35S promoter that is located 5' to the cDNA fragment and termination sequences from the nopaline synthase (NOS) that are located 3' to the cDNA fragment. The cDNAs for the *Impatiens* polypeptide was introduced in the NcoI and EcoRI sites of the vector pML63. The cDNA for the *Momordica* polypeptide was introduced into the NcoI and SmaI sites of the vector pML63. The NcoI and EcoRI sites flanking the *Impatiens* cDNA were generated by PCR amplification of the cDNAs using oligonucleotide primers that contained these restriction sites (SEQ ID NO:7 and SEQ ID NO:8, for the sense and antisense oligonucleotides, respectively). PCR amplification was conducted using the Pfu DNA polymerase. The NcoI site flanking the 5' end of the Momordica cDNA was generated by PCR amplification in a similar manner (SEQ ID NO:9 and SEQ ID NO:10). The 3' end of the PCR-generated Momordica cDNA was blunt-ended which allowed for cloning into the SmaI site of the vector pML63. The resulting fusions of the cauliflower mosaic virus 35S promoter with the cDNAs encoding fatty acid modifying enzymes associated with conjugated double bond synthesis in seeds of *Impatiens balsamina* or *Momordica charantia* and NOS termination sequences were released from the vector pML63 by digestion with XbaI. The resulting XbaI fragment was ligated into the corresponding site of the binary vector pZS199 The vector pZS199 contains the following elements: (1) the chimeric gene nopaline synthase/neomycin phosphotransferase as a selectable marker for transformed plant cells (Brevan et al. (1984) Nature 304:184–186), (2) the left and right borders of the T-DNA of the Ti plasmid (Brevan et al. (1984) Nucl. Acids Res. 12:8711–8720), (3) the *E. coli* lacZ-complementing segment (Vieria and Messing (1982) Gene 19:259–267) with unique restriction endonuclease sites for EcoRI, KpnI, BamHI, XbaI and SalI, (4) the bacterial replication origin from the *Pseudomonas* plasmid pVS1 (Itoh et al. (1984) Plasmid 11:206–220), and (5) the bacterial neomycin phosphotransferase gene from Tn5 (Berg et al. (1975) *Proc. Natl. Acad. Sci. U.S.A.* 72:3628–3632) as a selectable marker for transformed *A. tumefaciens*. The nopaline synthase promoter in the plant selectable marker was replaced by the 35S promoter (Odell et al. (1985) Nature, 313:810–813) by a standard restriction endonuclease digestion and ligation strategy.

Gene fusions of the *Impatiens balsamina* or *Momordica charantia* cDNAs with the cauliflower mosaic virus 35S promoter and the NOS termination sequences in vector pZS199 were introduced into *Agrobacterium tumefaciens* strain LBA4404. Tobacco (*Nicotiana tabacum* L. cv Xanthi) was transformed with *A. tumefaciens* harboring the *Impatiens* or *Momordica* gene constructs by infection of leaf disks (Horsch, R. B., Fry, J. E., Hoffman, N. E., Eicholtz, D., Rogers, S. G., and Fraley, R. T. (1985) Science 227: 1229–1231; Rogers, S. G., Horsch, R. B., and Fraley, R. T. (1986) Methods Enzymol. 118: 627–648). Stably transformed tobacco was selected by the ability of cells to grow on media containing kanamycin. The fatty acid composition of callus samples of transformed tobacco was examined for the production eleostearic and parinaric acids by gas chromatographic analysis of fatty acid methyl esters derived from the callus.

Example 4

Analysis of Eleostearic and Parinaric Acids in Transgenic Plant Tissues

Fatty acids in callus samples from tobacco transformed with gene constructs described in Example 6 were directly transesterified in methanol containing 1% sodium methoxide. The fatty acid methyl esters were extracted into heptane and a portion of the heptane extract was analyzed by gas liquid chromatography as described in Hitz et al. [Plant Physiol 105:635–641 (1994)]. In callus samples of tobacco transformed with gene constructs containing the *Impatiens* cDNA or the *Momordica* cDNA fatty acids were detected that had retention times equivalent to those of α-eleostearic and α-parinaric acids from extracts of *Impatiens balsamina* and *Momordica charantia* seed oil. Neither fatty acid was detected in extracts of tobacco callus transformed with only the expression vector lacking the *Impatiens* and *Momordica* cDNAs. In addition, fatty acid methyl esters were prepared from callus samples of tobacco transformed with gene constructs containing the *Impatiens* cDNA or the *Momordica* cDNA and were analyzed by GC-MS (gas chromatography-mass spectrometry) to confirm the identity of novel fatty acids that may have been produced. Fatty acid methyl esters were analyzed by GC-MS using a Hewlett Packard 6890 gas chromatograph interfaced with a Hewlett Packard 5973 mass selective detector (MSD). Samples were separated with a 30-m×0.25-mm (inner diameter) INNO-Wax column (Hewlett Packard). The oven temperature was programmed from 185° C. (3.5 min hold) to 215° C. (5 min hold) at a rate of 2° C./min and then to 230° at a rate of 5° C./min. The ionization potential of the MSD was 70 eV. In fatty acid methyl esters from callus expressing either cDNA, both eleostearic and parinaric acids were detected. The mass spectra of the methyl esters of these fatty acids are distinguished by abundant molecular ions, particularly when compared to polyunsaturated fatty acids such as α-linolenic acid that contain methylene interrupted (i.e., non-conjugated) double bonds. The distinguishing molecular ions detected in mass spectra of methyl esters of eleostearic acid and parinaric acid from the transgenic tobacco callus are 292 m/z and 290 m/z, respectively. In addition, the mass spectra of methyl eleostearic acid and parinaric in tobacco callus samples were identical to those of the corresponding fatty acid acid methyl esters in extracts of *Momordica* and *Impatiens* seeds. Transgenic tobacco callus expressing the *Impatiens* cDNA accumulated eleostearic acid and parinaric acid to amounts of 3.4% and 1.7%, respectively, relative to total fatty acid. Transgenic tobacco callus expressing the *Momordica* cDNA accumulated eleostearic acid and parinaric acid to amounts 1.7% and 1.1%, respectively.

Example 5

Expression of *Impatiens balsamina* Clone ImpH8Fad2 in *Saccharomyces cerevisiae*

The *Impatiens balsamina* clone ImpH8Fad2 was partially digested with the restriction enzymes EcoRI and XhoI. A resulting 1.5 kb DNA fragment containing the entire cDNA insert was purified by agarose gel electrophoresis. The cDNA insert was obtained from agarose gel by digestion with GELase™ (Epicentre Technologies) according to the manufacturer's instructions, ethanol precipitated, dried and resuspended in 20 μL of water. The purified cDNA was ligated into the EcoRI and XhoI sites of the *Saccharomyces cerevisiae* expression vector pYES2 (Invitrogen) using T4 DNA ligase (New England Biolabs). The resulting plasmid pYes2/ImpH8Fad2 was introduced into *Saccharomyces cerevisiae* INVSc1 (=Invitrogen)cells by lithium acetate-mediated transformation [Sherman F, Fink G R, Hicks J B, *Methods in Yeast Genetics: A Laboratory Course Manual*, Cold Spring Harbor Lab. Press, Plainview, N.Y. (1987)]. Transformed cells were selected by their ability to grow in the absence of uracil. Individual colonies of transformed cells were then grown for 2 days at 30° in growth media lacking uracil [0.17% (w/v) yeast nitrogen base without amino acids (Difco), 0.5% (w/v) ammonium sulfate, and 0.18% SC-URA (Bio101)] supplemented with glycerol and glucose to a final concentration of 5% (v/v) and 0.5% (w/v), respectively. Cells were then washed twice in the growth media described above that was supplemented instead with galactose to a final concentration of 2% (w/v). The washed cells were then diluted to $O.D._{600} \approx 0.2$ in the galactose-containing growth media that also contained Tergitol NP-40 (Sigma) at a concentration of 0.2% (w/v). Aliquots of these cells were grown without exogenous fatty acids or with the addition of either linoleic acid ($18:2\Delta^{9cis,12cis}$) or α-linolenic acid ($18:3\Delta^{9cis,12cis,15cis}$) at a final concentration of 2 mM. Following 4 days of growth at 16°, the *S. cerevisiae* cells were harvested and examined for the accumulation of fatty acids containing conjugated double bonds as described in Example 4. In cells grown in media containing linoleic acid, α-eleostearic acid was detected in amounts of up to 0.6% (w/w) of the total fatty acids. However, no α-parinaric acid was detected in extracts of these cultures. Conversely, in extracts of cultures grown in media containing α-linolenic acid, α-parinaric acid accumulated to amounts of up to 0.9% (w/w) of the total fatty acids, but no α-eleostearic acid was detected. These data suggest that linoleic acid is the substrate for α-eleostearic acid synthesis and that α-linolenic acid is the substrate for parinaric acid synthesis via the activity of the *Impatiens balsamina* fatty acid modifying enzyme associated with conjugated double bond formation.

Taken together, the results from tobacco transformations and yeast expression described in the preceding Examples prove that the enzyme products encoded by SEQ ID NO:1 and SEQ ID NO:3 are capable of catalyzing the production of fatty acids containing conjugated double bonds when transgenically introduced into a plant or yeast cultures that do not normally produce or accumulate fatty acids containing conjugated double bonds.

Example 6

Comparison of the Sequences of Proteins from ImpH8Fad2 and MomFad2 with Members of the Omega-6 Desaturase Class of Enzymes The deduced amino acid sequences from cDNA clones ImpH8Fad2 and MomFad2 were compared to the deduced amino acid sequences encoding (i) a known fatty acid desaturase from soybean (World Patent Publication No. WO94/11516) and (ii) a fatty acid hydroxylase from castor bean (van de Loo, F. J. et al. (1995) Proc. Natl. Acad. Sci. U.S.A. 92 (15):6743–6747) using the multiple sequence comparison program Megalign (v3.1.7) from the Lasargene™ software package (DNASTAR Inc., Madison, Wis.) and the Clustal method of alignment (default program parameters). The aligned sequences are shown in FIG. 1. All four sequences, including those of the proteins from *Impatiens balsamina* and *Momordica charantia* are related by eight very highly conserved histidine residues that are apparently part of the binding site for the two iron cluster that is required in the active site of enzymes in this class (Shanklin, J. et al. (1994) Biochemistry 33:12787–12793). These conserved residues are identified as boxed elements in FIG. 1. The amino acid sequence encoded by the *Impatiens balsamina* cDNA clone ImpH8Fad2 is 57.0% identical to the soybean sequence and 55.2% identical to the castor sequence. The amino acid sequence encoded by the *Momordica charantia* cDNA clone MomFad2 is 56.7% identical to the soybean sequence and 53.5% identical to the castor sequence. Overall, the sequence similarity shared by the *Impatiens balsamina* and *Momordica charantia* proteins is 52.6%.

Thus, changes in a comparatively small number of amino acid residues in conserved regions of the protein are sufficient to alter the activity in this class of enzymes from one of introducing a double bond (i.e., a desaturase) to one of introducing an hydroxyl group (i.e., a hydroxylase) or to one that is active in converting polyunsaturated fatty acids to fatty acids containing multiple conjugated double bonds.

Example 7

Production of Fatty Acids with Conjugated Double Bonds in Soybean Embryos and Seeds Fatty acid modifying enzymes associated with conjugated double bond synthesis in seeds of *Impatiens balsamina* and *Momordica charantia* can be expressed in cells of dicots that normally produce storage lipid by the construction of appropriate chimeric genes followed by stable introduction of those genes into the host plant. As an example of this method, *Impatiens* and *Momordica* fatty acid modifying enzymes associated with conjugated double bond synthesis were expressed in transgenic soybean embryos using a seed-specific promoter.

A plasmid pZBL100 containing chimeric genes to allow expression of hygromycin B phosphotransferase in certain bacteria and in plant cells was constructed from the following genetic elements: a.) T7 promoter+Shine-Delgamo/hygromycin B phosphotransferase (HPT)/T7 terminator sequence, b.) 35S promoter from cauliflower mosaic virus (CaMV)/hygromycin B phosphotransferase (HPT)/nopaline synthase (NOS3' from *Agrobacterium tumefaciens* T-DNA, and c.) pSP72 plasmid vector (Promega) with β-lactamase coding region (ampicillin resistance gene) removed.

The hygromycin B phosphotransferase gene was amplified by PCR from *E. coli* strain W677 (Gritz, L. and Davies, J (1983) Gene 25:179–188 which contained a Klebsiella derived plasmid pJR225 (Gritz, L. and Davies, J (1983) Gene 25:179–188. Starting with the pSP72 vector (Promega) the elements were assembled into a single plasmid using standard cloning methods (Maniatis).

Plasmid pZBL100 thus contains the T7 promoter/HPT/T7 terminator cassette for expression of the HPT enzyme in certain strains of *E. coli*, such as NovaBlue (DE3) (Novagen), that are lysogenic for lambda DE3 (which carries the T7 RNA Polymerase gene under lacUV5 control). Plasmid pZBL100 also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems.

PZBL100 also contains three unique restriction endonuclease sites suitable for the cloning of other chimeric genes into this vector.

A plasmid for expression of the cDNA encoding fatty acid modifying enzymes associated with conjugated double bond synthesis in seeds of *Impatiens balsamina* and *Momordica charantia* under control of the soybean β-conglycinin promoter (Beachy et al., (1985) EMBO J. 4:3047–3053) can be constructed. The construction of this vector was facilitated by the use of plasmids pCW109 and pML18, both of which have been described (see World Patent Publication No. WO 94/11516).

A unique NotI site was introduced into the cloning region between the β-conglycinin promoter and the phaseolin 3' end in pCW109 by digestion with NcoI and XbaI followed by removal of the single stranded DNA ends with mung bean exonuclease. NotI linkers (New England Biochemical) were ligated into the linearized plasmid to produce plasmid pAW35. The single NotI site in pML 18 was destroyed by digestion with NotI, filling in the single stranded ends with dNTPs and Klenow fragment followed by re-ligation of the linearized plasmid. The modified pML18 was then digested with HindIII and treated with calf intestinal phosphatase.

The β-conglycinin:NotI:phaseolin expression cassette in pAW35 was removed by digestion with Hind III and the 1.8 kB fragment was isolated by agarose gel electrophoresis. The isolated fragment was ligated into the modified and linearized pML18 construction described above. A clone with the desired orientation was identified by digestion with NotI and XbaI to release a 1.08 kB fragment indicating that the orientation of the β-conglycinin transcription unit was the same as the selectable marker transcription unit. The resulting plasmid was given the name pBS 19.

HindIII is one of the unique cloning sites available in pZBL100. To assemble the final expression cassette, pBS19 and pZBL100 were both digested with HindIII. The β-conglycinin containing fragment from pBS19 was isolated by gel electrophoresis and ligated into the digested pZBL10, which had been treated with calf alkaline phosphatase. The resulting plasmid was named pKS67.

cDNAs for the *Impatiens* and *Momordica* enzymes associated with conjugated double bond formation were amplified by PCR to generate flanking NotI sites to allow for cloning into the corresponding restriction site of plasmid pKS67. The 5' and 3' oligonucleotide primers used for the amplification of the *Impatiens* cDNA are provided in SEQ ID NO:11 and SEQ ID NO:12, respectively. The 5' primer consisted of bases 19 to 39 in SEQ ID NO:1 with extra bases at the 5' end consisting of 5'-AAG GAA AAA AGC GGC CGC-3' added to encode a NotI site and ten additional 5' flanking bases to enhance the restriction enzyme activity with the resulting PCR product. The 3' primer consisted of the reverse complement of bases 1150 to 1170 in SEQ ID NO:1 with extra bases at the 5' end consisting of 5'-AAG-GAAAAAAGCGGCCGC-3' added to provide a NotI site and ten additional bases to enhance restriction digestion. The 5' and 3' oligonucleotide primers used for the amplification of the *Momordica* cDNA are provided in SEQ ID NO:13 and SEQ ID NO:14, respectively. The 5' primer consisted of bases 74 to 94 in SEQ ID NO:3 with extra bases 5"-AAG GAA AAA AGC GGC CGC-3' added to encode a NotI site and ten additional 5' flanking bases to enhance the restriction enzyme activity with the resulting PCR product. The 3' primer consisted of the reverse complement of bases 1253 to 1273 in SEQ ID NO:3 with extra bases 5'-AAG-GAAAAAAGCGGCCGC-3' added to provide a Not I site and ten additional bases to enhance restriction digestion.

PCR reactions were conducted using Pfu polymerase (Stratagene) and plasmids containing the *Impatiens* and *Momordica* cDNA sequences shown in SEQ ID NO:1 and 3, respectively, as templates. Products from amplification reactions were purified using Wizard PCR DNA purification system (Promega) and cloned into the intermediate vector pGEM-t (Promega). To facilitate ligation into this vector, a single adenine base was added to the 3' end of each strand by incubation of purified PCR products for 20 minutes at 72° with 200 μM dATP, 2.5 units Amplitaq DNA polymerase (Perkin-Elmer) and 1.5 mM MgCl$_2$ in a final volume of 100 μL. Ligation products containing the amplified Impatiens and Momordica cDNAs were digested with NotI, and the released inserts were purified by agarose gel electrophoresis. The isolated NotI fragments, which contained the coding sequences for the *Impatiens* and *Momordica* fatty acid modifying enzymes associated with conjugated double bond synthesis, were ligated into the NotI site of vector pKS67. The resulting plasmids contained chimeric genes consisting of the 5' β-conglycinin promoter and 3'phaseolin termination sequences flanking the coding sequences of either the Impatiens or the Momordica fatty acid modifying enzyme associated with conjugated double bond synthesis.

Gene fusions of the *Impatiens balsamina* or *Momordica charantia* cDNAs with the conglycinin promoter and phaseolin termination sequences in vector pKS67 were introduced into soybean embryos using the particle bombardment method of transformation. To induce somatic embryos, cotyledons, 3–5 mm in length dissected from surface sterilized, immature seeds of a soybean cultivar A2872 or JACK-910 were cultured in the light or dark at 26° C. on an appropriate agar medium for 6–10 weeks. Somatic embryos that produce secondary embryos were then excised and placed into a suitable liquid medium. After repeated selection for clusters of somatic embryos that multiplied as early, globular staged embryos, the suspensions were maintained as described below.

Soybean embryogenic suspension cultures were maintained in 35 mL liquid media on a rotary shaker, 150 rpm, at 26° C. with florescent lights on a 16:8 hour day/night schedule. Cultures were subcultured every two weeks by inoculating approximately 35 mg of tissue into 35 mL of liquid medium.

Soybean embryogenic suspension cultures were then transformed with the vector pKS67 containing the Impatiens or Momordica cDNA for fatty acid modifying enzymes associated with conjugated double synthesis by the method of particle gun bombardment (Klein et al. (1987) Nature (London) 327:70, U.S. Pat. No. 4,945,050). A DuPont Biolistic™ PDS1000/HE instrument (helium retrofit) was used for these transformations.

To 50 mL of a 60 mg/mL 1 mm gold particle suspension were added (in order): 5 mL DNA (1 mg/mL), 20 ml spermidine (0.1 M), and 50 mL CaCl$_2$ (2.5 M). The particle preparation was then agitated for three minutes, spun in a microfuge for 10 seconds and the supernatant removed. The DNA-coated particles were then washed once in 400 mL 70% ethanol and resuspended in 40 mL of anhydrous ethanol. The DNA/particle suspension was sonicated three times for one second each. Five mL of the DNA-coated gold particles was then loaded on each macro carrier disk.

Approximately 300–400 mg of a two-week-old suspension culture was placed in an empty 60×15-mm petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post bombardment with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos.

Transgenic soybean embryos selected and maintained in this manner were analyzed for eleostearic acid and parinaric acid content using methods described in Example 4 (Table 1). Individual embryos expressing either the Impatiens or Momordica fatty acid modifying enzyme for conjugated double bond synthesis were homogenized in 1% (w/v) sodium methoxide in methanol. Fatty acid methyl esters resulting from this transesterification step were analyzed by both GC and GC-MS as described in Example 4. Methyl esters of eleostearic and parinaric acids were identified in transgenic soybean extracts by comparison of retention times and mass spectra with those of fatty acid methyl esters prepared from seeds of *Impatiens balsamina* and *Momordica charantia*. The total fatty acids of soybean embryos expressing the Impatiens fatty acid modifying enzyme associated with conjugated double bond synthesis were found to contain as much as 3% α-eleostearic acid and 2% α-parinaric acid (FIG. 2 and Table 1). In addition, the total fatty acids of soybean embryos expressing the *Momordica* fatty acid modifying enzyme associated with conjugated double bond synthesis were found to contain as much as 16.5% eleostearic acid and 1.5% α-parinaric acid (FIG. 3 and Table 1). In soybean embryos expressing the *Momordica* enzyme, eleostearic acid was detected principally as α-eleostearic acid with lesser amounts of at least two other cis-trans isomers of eleostearic acid.

TABLE 1

Embryo Fatty Acid Compositions of Soybean Transgenic Lines Expressing the Impatiens and Momordica Enzymes (Fad 2) Associated With Conjugated Double Bond Formation

| Fatty Acid | Wild-type | ImpFad2 | | | MomFad2 | | |
|---|---|---|---|---|---|---|---|
| Weight %[1]: | (n = 3)[2] | 1[3] | 2 | 3 | 1 | 2 | 3 |
| 16:0 | 15.1 ± 0.3 | 13.3 | 13.2 | 13.5 | 6.9 | 7.9 | 8.4 |
| 18:0 | 3.1 ± 0.2 | 4.2 | 2.5 | 3.1 | 2.4 | 2.1 | 2.3 |
| 18:1 | 9.7 ± 0.5 | 20.8 | 12.2 | 11.1 | 43.1 | 36.8 | 41.9 |
| 18:2 | 48.7 ± 1.6 | 46.3 | 53.8 | 53.0 | 24.1 | 29.4 | 25.1 |
| 18:3 | 22.8 ± 2.0 | 9.2 | 12.5 | 17.3 | 3.1 | 5.1 | 6.1 |
| Eleostearic[4] | N.D.[5] | 3.0 | 2.8 | 0.6 | 17.4 | 15.9 | 12.4 |
| α-Parinaric | N.D. | 2.2 | 2.0 | 1.0 | 1.0 | 1.0 | 1.8 |
| Other[6] | <1.0 | <1.0 | <1.0 | <1.0 | <2.0 | <2.0 | <2.0 |

[1]The fatty acid compositions are given as a percentage of total oil weight
[2]Wild-type values were obtained from three separate measurements (± standard deviation) of single embryos.
[3]Analyses were conducted on single embryos from three independent transgenic lines.
[4]Values include tentatively identified cis-trans isomers of α-eleostearic acid, which account for <1.0 wt % of the total fatty acids (see FIG. 2B and 3B). The remainder is composed of α-eleostearic acid.
[5]N.D. = not detected.
[6]Includes primarily 20:0, 20:1, 22:0, and 22:1.

To examine the ability of the *Momordica* fatty acid modifying enzyme associated with conjugated double bond synthesis to function in seeds of crop plants, transgenic soybean embryos expressing this enzyme were regenerated into plants. The fatty acid compositions of segregating seeds from these plants were examined by GC and GC-MS as described in Example 4

As indicated in FIG. 4 and Table 2, seeds expressing the Momordica enzyme accumulated α-eleostearic acid to amounts of more than 13% of the total fatty acids and also accumulated α-parinaric acid to approximately 0.5% of the total fatty acids. Accompanying the accumulation of α-eleostearic acid was a large rise in the oleic acid (18:1) content of transgenic seeds, which increased from about 18 wt % in wild-type seeds to nearly 50 wt % of the total fatty acids. In addition, the linolenic acid (18:3) content declined from nearly 9 wt % in wild-type seeds to about 1 wt % of the total fatty acids of transgenic seeds. These results demonstrate the ability to produce α-eleostearic and α-parinaric acids in seeds of a crop species by the transgenic expression of a fatty acid modifying enzyme associated with conjugated double bond synthesis.

TABLE 2

Seed Fatty Acid Compositions From
Soybean Transgenic Lines Expressing the Momordica
Enzyme Associated With Conjugated Double Bond Formation

| Fatty Acid | Wild-type | MomFad2 | | |
|---|---|---|---|---|
| Weight %[1]: | (n = 3)[2] | Line 1[3] | Line2 | Line 3 |
| 16:0 | 11.3 ± 1.2 | 8.8 | 8.4 | 9.7 |
| 18:0 | 3.7 ± 0.2 | 3.6 | 3.5 | 3.8 |
| 18:1 | 17.9 ± 2.3 | 44.5 | 48.9 | 47.2 |
| 18:2 | 57.7 ± 0.9 | 25.7 | 22.3 | 24.7 |
| 18:3 | 8.6 ± 0.5 | 1.0 | 0.7 | 1.0 |
| Eleostearic[4] | N.D.[5] | 13.9 | 13.4 | 11.6 |
| α-Parinaric | N.D. | 0.5 | 0.4 | 0.5 |
| Other[6] | <1.0 | <2.0 | <2.2 | <1.5 |

[1]The fatty acid compositions are given as a percentage of total oil weight
[2]Wild-type values were obtained from three separate measurements (± standard deviation) of single seeds.
[3]Analyses were conducted on single seeds from three independent transgenic lines.
[4]Values include tentatively identified cis-trans isomers of α-eleostearic acid, which account for <1.5 wt % of the total fatty acids (see FIG. 4B). The remainder is composed of α-eleostearic acid.
[5]N.D. = not detected.
[6]Includes primarily 20:0, 20:1, 22:0, and 22:1.

Example 8

Identification of a cDNA From Seeds of *Chrysobalanus icaco* for a Fatty Acid Modifying Enzyme Associated With Conjugated Double Bond Synthesis Results from *Impatiens balsamina* and *Momordica charantia* described in Examples 4, 5, 7 demonstrated that enzymes related to the ω[6]-oleic acid desaturase are involved in the synthesis of the conjugated double bonds found in α-eleostearic and α-parinaric acids. Based on this knowledge, attempts were made to identify additional cDNAs encoding fatty acid modifying enzymes associated with conjugated double bond synthesis from plants unrelated to *Impatiens balsamina* and *Momordica charantia*. In this regard, seeds of *Chrysobalanus icaco* (a member of the Chrysobalanaceae family) accumulate large amounts of α-eleostearic and α-paranaric acids as well as 4-keto derivatives of these fatty acids (Badami, R. C. and Batil, K. B. (1981) *Prog. Lipid Res.* 19:119–153). As an initial step in identifying a fatty acid modifying enzyme associated with conjugated double bond synthesis from *Chrysobalanus icaco*, first strand cDNA was synthesized from 10 μg of total RNA isolated from developing seeds of this plant using SuperScript II reverse transcriptase (Gibco BRL) according to the manufacturer's protocol. Oligo-dT was used as the primer for this reaction. The resulting first-strand cDNA was used a template for PCR amplification of coding sequences for the ω[6]-oleic acid desaturase and related polypeptides. The oligonucleotide primers for these reactions were based on partially conserved amino sequences in ω[6]-oleic acid desaturases. The conserved amino acid sequences that were used for the design of degenerate oligonucleotide primers were: KKAIPPHCF and WREAKEC. The corresponding oligonucleotides used in PCR reactions were: 5'ta tct aga gct cAA IAA RGC NAT HCC NCC NCA YTG YTT3' (sense, SEQ ID NO:31) and 5'taa gat ctg tat acR CAY TCY TTN GCY TCN CKC3' (antisense, SEQ ID NO:32) (Note: restriction sites for cloning and additional sequences to facilitate restriction digests are shown in lower case). Forty cycles of PCR amplification using Taq polymerase (Gibco-BRL) were conducted with the degenerate oligonucleotides and an aliquot of the first strand cDNA synthesis reaction. PCR products were then subcloned into pPCR-Script AMP (Stragene) according to the manufacturer's protocol and transformed into *E. coli* DH10B cells (Gibco-BRL). Nucleotide sequence was then obtained from the cDNA inserts from plasmids of six of the resulting colonies. These sequences revealed the occurrence of two distinct classes of cDNAs for ω[6]-oleic acid desaturase or related polypeptides in the *Chrysobalanus icaco* cDNA library. The two classes were designated Class 1 and Class 2. The partial polypetide encoded by the Class 2 cDNAs was more diverged from known ω[6]-oleic acid desaturases than the partial polypeptide encoded by Class 1 cDNAs. In addition, the Class 2 polypeptide contained a glutamic acid to aspartic acid substitution in the first histidine box relative to known ω[6]-oleic acid desaturases (see FIG. 1). This amino acid substitution was also present in the Momordica fatty acid modifying enzyme associated with conjugated double bond synthesis (amino acid number 115 in the *Momordica* enzyme) (see FIG. 1). This information suggested that the Class 2 cDNAs may encode a portion of a fatty acid modifying enzyme associated with conjugated double bond synthesis in *Chrysobalanus icaco* seeds.

To determine the activity of the *Chrysobalanus icaco* enzyme required the isolation of a cDNA encoding the entire polypeptide. As a first step, a cDNA library was constructed from polyA[+] RNA isolated from developing seeds of *Chrysobalanus icaco* seeds using methods described in Example 1. Plasmid was then isolated from an aliquot of *E. coli* DH10B cells harboring the library using a Qiagen Plasmid Mini Kit according to the manufacturer's protocol. The isolated plasmid was subsequently used as template for PCR reactions aimed at amplifying the entire 5' and 3' ends of the open-reading frame for the *Chrysobalanus icaco* Class 2 polypeptide. Based on the partial sequence of the Class 2 cDNAs (as described above), two oligonucleotide primers were designed that would allow for the amplification of the 5' and 3' ends of the open-reading frame when used in combination with primers specific to the library cloning vector pBluescript SK(−). In one PCR reaction, the T3 primer (5'AATTAACCCTCACTAAAGGG 3') was used in combination with Class 2-specific primer (5'ttt gga tcc GTG GAC GTA ATG CGT ATC AG 3', SEQ ID NO:15) for amplification of the complete 5' end of the open-reading frame. In a second reaction, the T7 primer (5'GTAATAC-GACTCACTATAGGGC 3') was used in combination with the Class 2-specific primer (5' ttt gaa ttc GCC ACC ACG CCT TTA GTG AC 3', SEQ ID NO:16) for amplification of the complete 3' end of the open-reading frame. In both reactions, approximately 200 ng of plasmid from the *Chrysobalanus icaco* cDNA library was used as template in a final reaction volume of 100 μl, and 40 cycles of amplification were conducted using Taq polymerase (Gibco BRL). The major product from each reaction was purified by agarose gel electrophoresis and subcloned into pPCR-Script AMP (Stratagene) according to the instructions supplied with the kit. Nucleotide sequence information was then obtained from subcloned products of the two reactions. From these sequences and from comparisons with those of other $\omega^6$-oleic acid desaturase and related polypeptides, it was determined that the complete 5' and 3' sequences for the open-reading frame of the *Chrysobalanus icaco* Class 2 polypeptide were contained in the products of the two PCR reactions.

Using these sequences, oligonucleotide primers were designed that flanked the 5' and 3' ends of the open-reading frame and would thus allow for the amplification of the full-length coding sequence for the *Chrysobalanus icaco* Class 2 polypeptide. The oligonucleotide primers that were used for the amplification of the open-reading frame of the *Chrysobalanus icaco* Class 2 polypeptide were: 5'ttt gga tcc GAA ATG GGA GCA GGT GGC $C_3$' (sense, SEQ ID NO:17) and 5'ttt gag ctc GCA CTC AAA ACT TGT CGA AC 3' (antisense, SEQ ID NO:18). Thirty cycles of PCR amplification were conducted using Pfu polymerase and approximately 200 ng of plasmid from the *Chrysobalanus icaco* cDNA library as template in a 100 μl reaction. The product from this reaction was subcloned into pPCR-Script AMP and sequenced in both strands. This sequence is shown in SEQ ID NO:19. Following restriction digestion with BamHI and SacI, the PCR product was moved from pPCR-Script AMP into the corresponding sites of the plant expression vector pBI121 (Clontech). The vector pBI121 is used for constitutive expression of transgenes mediated by the cauliflower mosaic virus 35S promoter. The full-length *Chrysobalanus icaco* Class 2 cDNA in pBI121 was then introduced into tobacco (*Nicotiana tabacum* cv. Xanthi) by *Agrobacterium tumefaciens*-mediated transformation using the methods described in Example 3. The resulting callus was selected on media containing kanamycin. Analysis of this callus by gas chromatography and gas chromatography-mass spectrometry as described in Examples 3 and 4 revealed the presence of α-eleostearic and α-paranaric acids. Amounts of α-eleostearic acid and α-paranaric acid accounted for as much as 4.7 wt % and 0.4 wt %, respectively, of the total fatty acids of callus samples. Neither fatty acid was detected in vector control samples. This result indicates that the *Chrysobalanus icaco* polypeptide shown in SEQ ID NO:20 and encoded by the cDNA shown in SEQ ID NO:19 is a fatty acid modifying enzyme associated with conjugated double bond synthesis. The identification of the *Chrysobalanus icaco* enzyme extends the results obtained from *Momordica charantia* and *Impatiens balsamina*.

To further characterize its functional properties, the *Chrysobalanus icaco* Class 2 polypeptide was expressed in soybean somatic embryos. Using information from SEQ ID NO: 19, oligonucleotide primers were designed that flanked the 5' and 3' ends of the open-reading frame and would thus allow for the amplification of the full-length coding sequence for the *Chrysobalanus icaco* Class 2 polypeptide. Also included in the oligonucleotide primers were flanking restriction sites that would allow for the cDNA to be cloned into the plant expression vector. The oligonucleotide primers that were used for the amplification of the open-reading frame of the *Chrysobalanus icaco* Class 2 polypeptide were: 5'tat gcg gcc gcG AAA TGG GAG CAG GTG GCC $C_3$' (sense, SEQ ID NO:21) and 5'tat gcg gcc gcG CAC TCA AAA CTT GTC GAA $C_3$' (antisense, SEQ ID NO:22). Thirty cycles of PCR amplification were conducted using Pfu polymerase and approximately 200 ng of plasmid from the *Chrysobalanus icaco* cDNA library as template in a 100 μl reaction. The product from this reaction was subcloned into pPCR-Script AMP (Stratagene) according to the manufacturer's protocol. Following restriction enzyme digestion with NotI, the cDNA insert encoding the open-reading frame of the *Chrysobalanus icaco* Class 2 polypeptide was ligated into the soybean expression vector pKS67, which was described in Example 7. The resulting construct containing a chimeric gene consisting of the soybean β-conglycinin promoter fused with the open-reading frame *Chrysobalanus icaco* Class 2 polypeptide was stably transformed into soybean somatic embryos as described in Example 7. Hygromycin-resistant embryos resulting from the transformation were examined for the presence of fatty acids containing conjugated double bonds using GC and GC-MS as described in Example 4. As indicated in FIG. 5 and Table 3, amounts of α-eleostearic acid detected in somatic embryos expressing the *Chrysobalanus icaco* Class 2 polypeptide were as high as 21 wt % of the total fatty acids, and α-paranaric acid accounted for approximately 1 wt % of the total fatty acids of transgenic embryos. Neither fatty acid was detected in wild-type soybean embryos.

TABLE 3

Embryo Fatty Acid Compositions From Soybean Transgenic Lines Expressing the Chrysobalanus Enzyme Associated With Conjugated Double Bond Formation

| Fatty Acid Weight %[1]: | W'ild-type (n = 5)[2] | ChrFad2 (n = 6)[3] |
| --- | --- | --- |
| 16:0 | 13.7 ± 0.7 | 7.0 ± 1.4 |
| 18:0 | 2.7 ± 0.5 | 1.9 ± 0.6 |
| 18:1 | 9.7 ± 1.9 | 37.6 ± 6.2 |
| 18:2 | 55.0 ± 3.2 | 28.1 ± 3.8 |
| 18:3 | 17.1 ± 1.4 | 6.0 ± 2.5 |
| Eleostearic[4] | N.D.[5] | 16.4 ± 2.4 |
| α-Parinaric | N.D. | 0.9 ± 0.3 |
| Other[6] | <2.0 | <2.1 |

[1]The fatty acid compositions are given as a percentage of total oil weight
[2]Wild-type values were obtained from five separate measurements (± standard deviation) of single seeds.
[3]Analyses were conducted on single embyos from six independent transgenic lines.
[4]Values include tentatively identified cis-trans isomers of α-eleostearic acid, which account for <1.0 wt % of the total fatty acids (see FIG. 5B). The remainder is composed of α-eleostearic acid.
[5]N.D. = not detected.
[6]Includes primarily 20:0, 20:1, 22:0, and 22:1.

Example 9

Expression of Chimeric Genes in Monocot Cells

The oil storing tissues of most grass seeds are the embryo and its attending tissues the scutellum and to some extent the aleurone. Promoter sequences such as those controlling expression of the storage proteins Globulin 1 (Belanger, S. C. and Kriz, A. L (1989) Plant Physiol. 91:636–643) and Globulin 2 (Walace, N. H. and Kriz, A. L. (1991) Plant Physiol. 95:973–975) are appropriate for the expression of chimeric genes in these tissues.

A chimeric gene comprising a cDNA encoding fatty acid modifying enzymes associated with conjugated double bond synthesis in seeds of *Impatiens balsamina, Momordica charantia,* and *Chrysobalanus icaco* in sense orientation with respect to the maize Globulin 2 promoter that is located 5' to the cDNA fragment, and the Globulin 2, 3' end that is located 3' to the cDNA fragment, can be constructed. The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the correctly designed expression vector.

Such expression vectors should include genetic sequences elements conferring an origin of replication for the plasmid in its host, a gene capable of conferring a selectable trait such as autotrophy or antibiotic tolerance to the host cell carrying the plasmid and the promoter sequences for expression of desired genes in host plant cells. Further design features may include unique restriction endonuclease recognition sites between the elements of the plant gene promoter elements to allow convenient introduction genes to be controlled by those elements. Plants that can serve as suitable hosts include, but are not limited to, corn, rice, wheat, and palm.

The chimeric genes constructed as above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27°. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton® flying disc (Bio-Rad Labs). The particles are then accelerated into the corn tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 10

Expression of Chimeric Genes in Dicot Cells

Fatty acid modifying enzymes associated with conjugated double bond synthesis in seeds of *Impatiens balsamina, Momordica charantia,* and *Chrysobalanus icaco* can be expressed in cells of dicots that normally produce storage lipid by the construction of appropriate chimeric genes followed by stable introduction of those genes into the host plant. An example of this method is the seed specific expression in soybean of fatty acid modifying enzymes associated with conjugated double bond synthesis in seeds of *Impatiens balsamina* and *Momordica charantia,* and *Chrysobalanus icaco*. Other plants that can be used include, but are not limited to, oilseed Brassica species, peanut, sunflower, safflower, cotton, flax, and cocoa.

A plasmid pKS18HH chimeric genes to allow expression of Hygromycin B Phosphotransferase in certain bacteria and in plant cells can be constructed from the following genetic elements: a) T7 Promoter+Shine-Delgarno/Hygromycin B Phosphotransferase (HPT)/T7 Terminator Sequence, b) 35S Promoter from cauliflower mosaic virus (CaMV)/Hygromycin B Phosphotransferase (HPT)/Nopaline Synthase (NOS3' from *Agrobacterium tumefaciens* T-DNA, and c) pSP72 plasmid vector (Promega) with β-lactamase coding region (ampicillin resistance gene) removed.

The Hygromycin B Phosphotransferase gene can be amplified by PCR from *E. coli* strain W677, which contains a Klebsiella derived plasmid pJR225. Starting with the pSP72 vector the elements are assembled into a single plasmid using standard cloning methods (Maniatis).

Plasmid pKS18HH thus contains the T7 promoter/HPT/T7 terminator cassette for expression of the HPT enzyme in certain strains of *E. coli*, such as NovaBlue(DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restriction endonuclease sites suitable for the cloning of other chimeric genes into this vector.

A plasmid for expression of the cDNA encoding fatty acid modifying enzymes associated with conjugated double bond synthesis in seeds of *Impatiens balsamina, Momordica charantia*, and *Chrysobalanus icaco* is made to be under the control of a soybean β-conglycinin promoter (Beachy et al., (1985) EMBO J. 4:3047–3053), or any dicot promoter that allows for high-level expression in seeds, such as, but not limited to, seed storage proteins. The seed storage proteins are strictly regulated, being expressed almost exclusively in seeds in a highly organ-specific and stage specific manner (Higgins et al., Ann. Rev. Plant Physiol., 35:191–221 (1984); Goldberg et al., Cell, 56:149–160 (1989); Thompson et al., BioEssays, 10:108–113 (1989)). Moreover, different seed storage proteins may be expressed at different stages of seed development. The construction of this vector is facilitated by the use of plasmids pCW109 and pML18, both of which have been described (see World Patent Publication No. WO94/11516).

A unique NotI site is introduced into the cloning region between the β-conglycinin promoter and the phaseolin 3' end in pCW109 by digestion with Nco I and Xba I followed by removal of the single stranded DNA ends with mung bean exonuclease. Not I linkers (New England Biochemical catalog number NEB 1125) are ligated into the linearized plasmid to produce plasmid pAW35. The single NotI site in pML18 is destroyed by digestion with NotI, filling in the single stranded ends with dNTPs and Klenow fragment followed by re-ligation of the linearized plasmid. The modified pML18 is then digested with HindIII and treated with calf intestinal phosphatase.

The β-conglycinin:Not I:phaseolin expression cassette in pAW35 is removed by digestion with Hind III and the 1.79 kB fragment is isolated by agarose gel electrophoresis. The isolated fragment is ligated into the modified and linearized pML18 construction described above. A clone with the desired orientation was identified by digestion with NotI and XbaI to release a 1.08 kB fragment indicating that the orientation of the β-conglycinin transcription unit is the same as the selectable marker transcription unit. The resulting plasmid is given the name pBS19.

HindIII is one of the unique cloning sites available in pKS18HH. To assemble the final expression cassette pBS19 and pKS18HH are both digested with HindIII. The β-conglycinin containing fragment from pBS19 is isolated by gel electrophoresis and ligated into the digested pKS18HH which had been treated with calf alkaline phosphatase. The resulting plasmid is named pRB20.

The PCR products amplified from clones for the *Impatiens, Momordica*, and *Chrysobalanus* polypeptides (described in Example 3 above) are digested with restriction enzymes to cleave the sites designed into the PCR primers. Plasmid pRB20 is also digested in a manner compatible with conventional cloning sites for the introduction of the PCR fragments. After phosphatase treatment of the linearized pRB20, PCR products are ligated into pRB20 and the ligation mixtures are used to transform *E. coli* strain DH10B. Colonies are selected and grown in liquid media for preparation of plasmid DNA. Digestion of the plasmid DNAs with an enzyme diagnostic for correct orientation of the coding sequences relative to the β-conglycinin promoter identifies clones for use in soybean transformation, or transformation into any suitable dicot host.

Soybean embryos are then transformed with the expression vector comprising sequences encoding an I*mpatiens, Momordica, Chrysobalanus* polypeptides described above. Subsequent culturing and selection of transformed plants is essentially the same as outlined in Example 7.

Using methods described in this Example, transformed dicot embryos with detectable levels of conjugated polyunsaturated fatty acids may be identified and propagated.

Example 11

Expression of Chimeric Genes in Microbial Cells

The cDNAs encoding the instant fatty acid modifying enzymes associated with conjugated double bond synthesis in seeds of *Impatiens balsamina, Momordica charantia*, and *Chrysobalanus icaco* can be inserted into the T7 *E. coli* expression vector pET24d (Novagen). For example, plasmid DNA containing a cDNA may be appropriately digested to release a nucleic acid fragment encoding the fatty acid modifying enzymes associated with conjugated double bond synthesis in seeds of *Impatiens balsamina, Momordica charantia*, and *Chrysobalanus icaco*. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pET24d is digested, dephosphorylated with alkaline phosphatase (NEB) and deproteinized with phenol/chloroform as decribed above. The prepared vector pET24d and fragment can then be ligated at 16° for 15 hours followed by transformation into DH5 electrocompetent cells (GIBCO BRL). Transformants can be selected on agar plates containing 2×YT media and 50 μg/mL kanamycin. Transformants containing the gene are then screened for the correct orientation with respect to pET24d T7 promoter by restriction enzyme analysis.

Clones in the correct orientation with respect to the T7 promoter can be transformed into BL21(DE3) competent cells (Novagen) and selected on 2×YT agar plates containing 50 μg/ml kanamycin. A colony arising from this transformation construct can be grown overnight at 30° C. in 2×YT media with 50 μg/mL kanamycin. The culture is then diluted two fold with fresh media, allowed to re-grow for 1 h, and induced by adding isopropyl-thiogalacto-pyranoside to 1 mM final concentration. Cells are then harvested by centrifugation after 3 h and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 12

Identification of a Diverged $\omega^6$-Oleic Acid Desaturase from Developing Seeds of *Licania michauxi*

*Licania michauxii*, like *Chrysobalanus icaco* described in Example 8, is a member of the Chrysobalanaceae family and accumulates large amounts of α-eleostearic and α-parinaric acids in its seed oil (Badami, R. C. and Batil, K. B. (1981) *Prog. Lipid Res.* 19:119–153). As demonstrated in Example 8, it is expected that the conjugated double bonds of α-eleostearic and α-parinaric acids in *Licania michauxi* seeds arise from the activity of a diverged form of the $\omega^6$-oleic acid desaturase. To identify cDNAs for this enzyme from *Licania michauxi*, PCR amplification was conducted using degenerate sense and antisense oligonucleotides designed from conserved amino acid sequences found in $\omega^6$-oleic acid desaturases and related enzymes. The template for these reactions was first strand cDNA synthesized from RNA isolated from developing *Licania michauxi* seeds. The methods and oligonucleotides used were the same as described in Example 8. The sequences of the resulting PCR products from *Licania michauxi* were found to encode portions of two distinct classes of $\omega^6$-oleic acid desaturase-type polypeptides. One of the classes shared 98% amino acid sequence identity with the corresponding portion of the Class 2 polypeptide from *Chrysobalanus icaco* described in Example 8. Given this close relation, sense and antisense oligonucleotides designed from sequences flanking the complete open-reading frame of the *Chrysobalanus icaco* Class 2 cDNA were used to amplify the corresponding full-length cDNA from *Licania michauxi*. The template for these PCR amplification reactions was a cDNA library prepared from developing seeds of *Licania michauxi* using methods described in Example 1. The sequence of the sense oligonucleotide was 5' tttccatggAGCAGGTGGCCAAAAG3' (SEQ ID NO:33) and the sequence of the antisense oligonucleotide was 5'tttagatctGCACTCAAAACTTGTC-GAAC3' (SEQ ID NO:34). PCR reactions were conducted using Pfu polymerase (Stratagene). The resulting product was subcloned into the vector pCR-Script AMP SK (+) (Stratagene) using the manufacturer's protocol. Nucleotide sequence was subsequently obtained from both strands of the subcloned PCR product. This sequence is shown in SEQ ID NO:23, and the amino acid sequence of the deduced polypeptide is shown in SEQ ID NO:24. The full-length cDNA sequence amplified from the *Licania michauxi* cDNA library was found to encompass the partial sequence obtained from PCR reactions using degenerate oligonucleotides that are described in Example 8.

The amino acid sequence of the *Licania michauxi* polypeptide shown in SEQ ID NO:24 shares 97% identity with sequence of the *Chrysobalanus icaco* Class 2 polypeptide described in Example 8. Expression of the *Chrysobalanus icaco* Class 2 polypeptide was shown to direct the formation of fatty acids with conjugated double bonds in transgenic soybean somatic embryos and tobacco callus as described in Example 8. Given the close relation with the *Chrysobalanus icaco* Class 2 polypeptide, it is expected that the *Licania michauxii* polypeptide also catalyzes the synthesis of fatty acids with conjugated double bonds. This can be tested by expression of the *Licania michauxi* cDNA (SEQ ID NO:23) in transgenic plants or microbial cells as described in Examples 9,10, and 11 and by subsequent analyses of fatty acid compositions of the transgenic plants or microbial cells as described in Example 4.

Example 13

Identification of $\omega^6$-Oleic Acid Desaturase-Related Sequences from Tung (*Aleurites fordii*)

Eleostearic acid composes >65% of the seed oil of tung (*Aleurites fordii*) (Badami, R. C. and Batil, K. B. (1981) *Prog. Lipid Res.* 19:119–153). This species thus represents an additional source of cDNAs or genes encoding c)$^6$-oleic acid desaturase-related enzymes associated with conjugated double bond formation. As described in Example 8, the coding sequences for these enzymes can be identified using PCR amplification with degenerate oligonucleotides designed from conserved amino acid sequences in $\omega^6$-oleic acid desaturases and related enzymes. The template for PCR amplification can be first-strand cDNA or cDNA libraries prepared from tissues that accumulate fatty acids with conjugated double bonds (as described in Example 8). In addition, genes for $\omega^6$-oleic acid desaturases do not contain introns within their open-reading frames (Okuley, J. et al. (1994) *Plant Cell* 6:147–158). Therefore, genomic DNA isolated from species such as tung can be used as template to amplify the coding sequences of $\omega^6$-oleic acid desaturase-related enzymes associated with conjugated double bond formation. As a demonstration of this, genomic DNA was isolated from tung leaves using the method described by Shure et al. (1983) *Cell* 35: 225–233. The resulting DNA was used as template for PCR reactions with degenerate oligonucleotide primers designed from conserved amino acid sequences in $\omega^6$-oleic acid desaturases and related enzymes. The sense oligonucleotide was 5'tt gaattcAARGCNATHCCNCCNCAYTGYTT3' (SEQ ID NO:25) which corresponds to the amino acid sequence KAIPPHCF, and the antisense oligonucleotide was 5'tt gaatTCCNCKNARCCARTCCCAYTC3' (SEQ ID NO:26) which corresponds to the amino acid sequence EWDW(L/F)RG. (Note: The base pairs in lower case were added for restriction digestion to facilitate cloning of PCR amplification products and flanking EcoRI recognition sequence is underlined.) Forty cycles of PCR amplification were conducted using Taq polymerase in a 100 μl reaction volume that contained 150 ng of tung genomic DNA. The annealing temperature used was 45° C. The resulting products of approximately 775 bp were subcloned into pGEM-T (Promega) according to the manufacturer's protocol and transformed into *E. coli* DH10B cells (Gibco-BRL). Nucleotide sequence was then obtained for cDNA inserts from plasmids of eleven of the resulting colonies. Homology comparisons indicated that these sequences encode 255 amino acid portions of $\omega^6$-oleic acid desaturase-type enzymes. In addition, the sequences corresponded to two distinct classes of genes, which were designated Class 1 (SEQ ID NO:27) and 2 (SEQ ID NO:29, see FIG. 1). The Class 1 and 2 gene products share 75% amino acid sequence identity (FIG. 1). Of these, the Class 2 gene product is more diverged relative to known $\omega^6$-oleic acid desaturases. For example, the 255 amino acid sequences encoded by the Class 1 and 2 PCR products share 76% and 72% identity, respectively, with the corresponding portion of the soybean $\omega^6$-oleic acid desaturase (FIG. 1). In addition, the residue immediately adjacent to the first histidine box in the Class 2 polypeptide is a glycine (as indicated by an asterisk in FIG. 1). A glycine in this position is only observed in $\omega^6$-oleic acid desaturase-related enzymes that have diverged functionality, such as the castor oleic acid hydroxylase (van de Loo, F. J. et al. (1995) *Proc. Natl. Acad. Sci. U.S.A.* 92:6743–6747) and the *Crepis palaestina* epoxidase (Lee, M. et al. (1998) *Science* 280:915–918). Given this feature of its primary structure and its more distant relation to known $\omega^6$-oleic acid desaturases, it is believed that the polypeptide encoded by the Class 2 gene is the enzyme associated with conjugated double bond formation from tung. There are two other amino acid changes that are believed to be useful in identifying enzymes involved in conjugated bond formation. The amino acid immediately following the first histidine, in the first histidine box mentioned above, is a conserved aspartate. The Chrysobalanus, Momordica, and Licania sequences have a glutamate substitution at this position that is not found in any other published Fad2 gene. The tung and Impatiens enzymes do not have this substitution, but they both have the glycine substitution two amino acids upstream of this position. Another amino acid difference that is believed to be useful is at position 312 of the Momordica sequence. Momordica, Chrysobalanus, and Licania all contain a proline substitution at this position. None of the other published Fad2 enzymes have this substitution.

The remaining portion of the tung gene is obtained using one of two methods. First a cDNA library is made from mRNA isolated from tung seeds or developing seedlings as outlined in Example 1. The library clones are randomly sequenced and analyzed as outlined in Example 2. Alternatively, PCR amplification of clones is accomplished using primers selected from the sequence presented in SEQ ID NO:29 such that a antisense primer is used to amplify the amino terminal portion of the gene and a sense primer amplifies the carboxy-terminal portion. The paired primers in the reaction are made to the plasmid vector sequence that resides upstream and downstream of the inserted cDNA, respectively. A second method to obtain the tung sequences involves using "inverse PCR" on the tung genomic DNA. Briefly, tung genomic DNA is fragmented using a restriction enzyme that gives a small (2–3 Kb) fragment that hybridizes to the sequence presented in SEQ ID NO:29. The digested genomic DNA is diluted and ligated in a reaction designed to favor intramolecular ligation. PCR primers are used that diverge from a sequence found in SEQ ID NO:29. The PCR fragment obtained in this reaction has the genomic sequences flanking SEQ ID NO:29 and is used to construct primers that allow for the PCR amplification of the complete tung gene responsible for conjugated bond formation in the fatty acids.

Example 14

Conjugated 18:3 Fatty Acids Can Improve Carcass Quality When Added to Animal Feed Experiments were conducted to evaluate the effects of feeding eleostearic (18:3) conjugated fatty acids on pig growth, carcass characteristics, and fat firmness. Twenty-four pigs (barrows, castrated males, from PIC genetics) with a capacity for high rates of daily lean growth and reduced back fat were randomly assigned by litter mates, weight, and block to three dietary treatments. Group one was fed normal corn feed, group two received normal corn feed supplemented with CLA, and the third group received normal corn feed supplemented with conjugated linolenic acids, i.e., ClnAs (18:3 conjugated fatty acids). Pigs were penned individually and identified by ear tattoo. The average initial weight of the barrows was 125 pounds. Pigs were placed on their respective test diets at 150 lb, after being fed a common diet.

Diets were fed in two phases: Phase 1 (150 to 200 lb), and Phase 2 (200 to 250 lb). Ingredient and nutrient compositions of the treatment diets are shown in Table 4 and Table 5, respectively. The diets were formulated to be isocaloric.

TABLE 4

Ingredient Composition of Diets

| Ingredient, % | NC[1] | NC + CLA | NC + ClnA |
|---|---|---|---|
| Grower Diets | | | |
| NC[1] | 69.826 | 69.826 | 69.826 |
| Soybean Meal, 48%[2] | 25.283 | 25.283 | 25.283 |
| A-V Fat[3] | 2.498 | 2.498 | 2.498 |
| L-Lysine-HCl[4] | 0.073 | 0.073 | 0.073 |
| Limestone[5] | 0.838 | 0.838 | 0.838 |
| Dical 21[6] | 0.761 | 0.761 | 0.761 |
| Choline CH, 60%[7] | 0.096 | 0.096 | 0.096 |
| TM & Vitamin Premix[8] | 0.250 | 0.250 | 0.250 |
| Salt[9] | 0.300 | 0.300 | 0.300 |
| Copper Sulfate[10] | 0.075 | 0.075 | 0.075 |
| Finisher Diets | | | |
| NC | 75.142 | 75.142 | 75.142 |
| Soybean Meal, 48% | 20.340 | 20.340 | 20.340 |
| A-V Fat | 2.564 | 2.564 | 2.564 |
| Limestone | 0.740 | 0.740 | 0.740 |
| Dical 21 | 0.525 | 0.525 | 0.525 |
| Choline CH, 60% | 0.065 | 0.065 | 0.065 |
| TM & Vitamin Premix | 0.250 | 0.250 | 0.250 |
| Salt | 0.300 | 0.300 | 0.300 |
| Copper Sulfate | 0.075 | 0.075 | 0.075 |

[1]normal hybrid corn, W677, from Wyffels, Atkinson.IL
[2]Perdue Farms, Inc., Greenville, NC
[3]Moyer Packing Co., Souderton, PA
[4]Archer Daniels Midland Co., Decatur, IL
[5]Akey, Inc. Lewisburg, OH
[6]Potash Company of Saskatchewan, Davenport, IA
[7]Akey, Inc. Lewisburg, OH
[8]Trace Minerals and Vitamin Premix, Young's, Greensboro, MD
[9]Akey, Inc. Lewisburg, OH
[10]Akey, Inc. Lewisburg, OH

TABLE 5

Calculated nutrient composition of treatment diets.

| Nutrient | Phase 1 (150–200 lb) | Phase 2 (200–250 lb) |
|---|---|---|
| Energy, kcal/lb | 1734 | 1756 |
| Energy, kcal/kg | 3823 | 3871 |
| Protein, mcal % | 18.00 | 16.00 |
| Lysine, mcal % | 1.05 | 0.86 |
| Methionine + Cysteine, mcal % | 0.64 | 0.61 |
| Calcium, % | 0.60 | 0.50 |
| Total Phosphorus | 0.55 | 0.49 |

The mixer used to prepare the diets was flushed with 300 lb corn prior to mixing and between each mix to prevent cross-contamination. Conjugated linoleic acid (CLA) was purchased from Conlinco, Inc. (Detroit Lakes, Minn.) as "Clareen™". Conjugated linolenic acid (ClnA) was from a commercial source of tung oil (Industrial Oil Products, Woodbury, N.Y.) that was approximately 65% α-eleostearic acid. To achieve a final conjugated fatty acid concentration of 0.50%, 0.83 lb CLA preparation/100 lb diet and 0.73 lb CLnA preparation/100 lb diet were added. To minimize oxidation of the conjugated fatty acid, diets were prepared each 14-days and refrigerated until use. Feed was added to feeders in minimal amounts daily. The antibiotic bacitracin methylene disalicylate (BMD, Alpharma, Inc., Fort Lee, N.J.) was included in all diets (50 g/ton). Feed samples were collected for amino acid and fatty acid analysis.

Live weights were recorded to determine average daily gains Phase 1 (150 to 200 lbs), and Phase 2 (200 to 250 lbs). Feed weight data were also collected to determine feed efficiency. Animals were observed 2–3 times daily for access to feeders and waterers, house temperatures, and any abnormal health conditions. Pigs were not replaced during the trial. Any animals that died were necropsied to determine the cause of death. Dead animal body weights were used to correct feed efficiency.

When pigs reached 250 pounds body weight they were slaughtered, processed and standard carcass measurements were collected. Because of limitations on conjugated fatty acid, pigs fed CLA and CLnA were fed a common diet four days prior to slaughter. Bellies from the eight pigs in each study group were evaluated for fat firmness evaluated by measuring belly thickness before and after compression. Fat compression was achieved by placing a 50 lb weight on the fresh belly for one hour. Fat compression was quantified by subtracting the compressed belly thickness from the initial belly thickness. Belly thickness was measured using a micrometer. The results of the belly compression evaluation are shown in Table 6. Data were analyzed as a randomized complete block design using the GLM (General Linear Model) procedure of SAS (Statistical Analysis Systems). Table values represent the difference between compressed and uncompressed pork belly thickness. A smaller number indicates reduced compression (i.e., greater firmness) of pork bellies. Because a pork belly is greater than 50% fat, the belly compression test is an indicator of relative firmness of pork belly fat. Addition of either CLA or CLnA to NC diets resulted in greater fat firmness in pigs. The improved pork fat firmness resulting from dietary addition of CLA is consistent with results reported by others (Eggert, J. M., et al. (1999) *J. Anim. Sci.* 77(*Suppl*):53; Thiel, R. C., et al. (1998) *J. Anim. Sci.* 76 (*Supp*): 13; Wiegand, B. R., F. C. Parrrish Jr., and J. C. Sparks (1999) *J. Anim. Sci.* 77 (*Suppl*):19; U.S. Pat. No. 5,554,646; and U.S. Pat. No. 5,851,572). Improved fat firmness resulting from dietary CLnA inclusion has not been previously reported. Based on the results of this experiment, addition of conjugated linoleic acid (CLA) or conjugated linolenic acid (ClnA) to pig diets results in improved fat firmness.

TABLE 6

Results of Fat Compression Test

| Measurement | NC | NC + CLA | NC + CLnA | SEM[1] |
|---|---|---|---|---|
| Pork Belly Compression, mm | 33.2[2] | 28.0 | 30.8 | 0.68 |

[1]Standard Error of the Mean
[2]All three test sample means were statistically different (P < 0.05),

---

What is claimed is:

1. A method of improving the carcass quality of an animal by supplementing a diet of the animal with animal feed comprising an oil obtained from a seed, wherein the seed is obtained from a plant cell transformed with a chimeric gene comprising an isolated nucleic acid fragment or functionally equivalent subfragment thereof of operably linked to at least one regulatory sequence, further wherein said isolated nucleic acid fragment encodes a plant fatty acid modifying enzyme associated with conjugated double bond formation further wherein said fragment or a functionally equivalent subfragment thereof (a) hybridizes to the nucleotide sequence set forth in SEQ ID NO: 3 under conditions of moderate stringency; or (b) encodes a polypeptide that has at least 45% sequence identity based on the Clustal method of alignment with a polypeptide set forth in SEQ ID NO: 4 or a functionally equivalent subfragment thereof.

2. The method of claim 1 wherein the isolated nucleic acid fragment is isolated from *Impatiens balsamina, Momordica charantia, Chrysobalanus icaco, Licania michauxii,* and *Aleurites fordii.*

3. The method of claim 1 or 2 wherein the plant fatty acid modifying enzyme is associated with the formation of at least one fatty acid selected from the group consisting of eleostearic acid and parinaric acid.

4. A method of improving the carcass quality of an animal by supplementing a diet of the animal with animal feed comprising an oil obtained from a seed, wherein the seed is obtained from a plant cell transformed with a chimeric gene comprising an isolated nucleic acid fragment or functionally equivalent subfragment thereof or a complement of the isolated nucleic acid fragment or functionally equivalent subfragment operably linked to at least one regulatory sequence, further wherein said isolated nucleic acid fragment encodes a plant fatty acid modifying enzyme associated with conjugated double bond formation further wherein said fragment or a functionally equivalent subfragment thereof (a) hybridizes to the nucleotide sequences set forth in SEQ ID NO: 3 under conditions of moderate stringency, or (b) encodes a polypeptide that has at least 45% sequence identity with a polypeptide as set forth in SEQ ID NO: 4 or a functionally equivalent subfragment thereof based on the Clustal method of alignment, and wherein the polypeptide is capable of catalyzing the production of at least one fatty acid selected from the group consisting of eleostearic acid and parinaric acid when expressed in a plant cell or yeast transformed with the isolated nucleic acid fragment and said fatty acids are not produced and/or accumulated in the untransformed plant cell or yeast.

5. The method of claim 4, wherein the plant cell comprises a cell from a crop, selected from the group consisting of soybean, Brassica species, corn, peanut, rice, wheat, sunflower, safflower, cotton, and cocoa.

* * * * *